(12) United States Patent
Stubbs et al.

(10) Patent No.: US 11,781,147 B2
(45) Date of Patent: Oct. 10, 2023

(54) **PROMOTER SEQUENCES AND METHODS THEREOF FOR ENHANCED PROTEIN PRODUCTION IN *BACILLUS* CELLS**

(71) Applicant: DANISCO US INC, Palo Alto, CA (US)

(72) Inventors: Stacey Irene Robida Stubbs, Woolwich Township, NJ (US); Cristina Bongiorni, Palo Alto, CA (US); Ryan L. Frisch, Newark, DE (US); Chris Leeflang, Oegstgeest (NL)

(73) Assignee: Danisco US Inc., Palo Alto, CA (US)

( * ) Notice: Subject to any disclaimer, the term of this patent is extended or adjusted under 35 U.S.C. 154(b) by 313 days.

(21) Appl. No.: 17/293,644

(22) PCT Filed: Nov. 25, 2019

(86) PCT No.: PCT/US2019/062955
§ 371 (c)(1),
(2) Date: May 13, 2021

(87) PCT Pub. No.: WO2020/112609
PCT Pub. Date: Jun. 4, 2020

(65) Prior Publication Data
US 2022/0010319 A1 Jan. 13, 2022

Related U.S. Application Data

(60) Provisional application No. 62/772,363, filed on Nov. 28, 2018.

(51) Int. Cl.
*C12N 15/75* (2006.01)
*C07K 14/32* (2006.01)
*C12N 9/14* (2006.01)

(52) U.S. Cl.
CPC .............. *C12N 15/75* (2013.01); *C07K 14/32* (2013.01); *C12N 9/14* (2013.01)

(58) Field of Classification Search
CPC ..................................................... C12N 15/75
See application file for complete search history.

(56) References Cited

FOREIGN PATENT DOCUMENTS

| WO | 2016134213 A2 | 8/2016 |
|---|---|---|
| WO | 2017112733 A1 | 6/2017 |
| WO | 2017152169 A1 | 9/2017 |
| WO | 2018118950 A1 | 6/2018 |
| WO | 2018136459 A1 | 7/2018 |
| WO | 2018156705 A1 | 8/2018 |

OTHER PUBLICATIONS

International Search Report from PCT App. No. PCT/US2019/062955 dated Feb. 7, 2020, 19 pages.
Coelho et al., "Bacillus subtilis promoter sequences data set for promoter prediction in Gram-positive bacteria", Data in Brief, vol. 19, May 13, 2018, pp. 264-270.
Guan et al., "Development of an efficient autoinducible expression system by promoter engineering in Bacillus subtilis", Microbial Cell Factories, vol. 15, No. 1, Apr. 25, 2016, 12 pages.
Sammarrai et al., "Differential Response of Bacillus subtilis rRNA Promoters to Nutritional Stress", Journal of Bacteriology, vol. 193, No. 3, Nov. 19, 2010, pp. 723-733.
Song et al., "Promoter Screening from Bacillus subtilis in Various Conditions Hunting for Synthetic Biology and Industrial Applications", PLoS One, vol. 11, No. 7, Jul. 5, 2016, p. e0158447.
Song et al., "Enhancement of extracellular expression of Bacillus naganoensis pullulanase from recombinant Bacillus subtilis: Effects of promoter and host", Protein Expression and Purification Academic Press, vol. 124, Apr. 2016, pp. 23-31.
Yu et al., "Identification of a highly efficient stationary phase promoter in Bacillus subtilis", Scientific Reports, vol. 5, No. 1, Dec. 17, 2015, pp. 1-9.

*Primary Examiner* — Suzanne M Noakes

(57) ABSTRACT

The present disclosure is generally related to novel promoter sequences and methods thereof for enhanced protein production in *Bacillus* sp. (host) cells. As set forth herein, the novel promoter sequences of the disclosure, when operably linked to a gene or open reading frame encoding a protein of interest, are particularly well suited for use in large scale production of industrially relevant proteins.

9 Claims, 5 Drawing Sheets

Specification includes a Sequence Listing.

Native B. subtilis rrnIp2 Promoter Sequence (SEQ ID NO: 39) Aligned with Synthetic rrnIp2-1 Promoter Sequence (SEQ ID NO: 40)

```
                                         -35                                                -10
rrnIp2   (1) GCTGATAAACAGCTGACATCAACTAAAAGCTTCATTAAATACTTTGAAAAAAGTTGTTGACTTAAAAGAAGCTAAATGTTATAGTAATAAA  (91)
rrnIp2-1 (1) GCTGATAAACAGCTGACATCAACTAAAAGTTTCATTAAATACTTTGAAAAAAGTTGTTGACTTAAAAGAAGCTAAATGTTATAGTAATTGT  (91)
```

FIG. 1A

Native B. subtilis rrnIp2 Promoter Sequence (SEQ ID NO: 39) Aligned with Synthetic rrnIp2-2 Promoter Sequence (SEQ ID NO: 58)

```
                                         -35                                                -10
rrnIp2   (1) GCTGATAAACAGCTGACATCAACTAAAAGCTTCATTAAATACTTTGAAAAAAGTTGTTGACTTAAAAGAAGCTAAATGTTATAGTAATAAA  (91)
rrnIp2-2 (1) GCTGATAAACAGCTGACATCAACTAAAAGCTTCATTAAATACTTTGAAAAAAGTTGTTGACTTAAAAGAAGCTAAATGTTATAGTAATTGT  (91)
```

FIG. 1B

Native B. subtilis rrnIp2 Promoter Sequence (SEQ ID NO: 39) Aligned with Synthetic rrnIp2-3 Promoter Sequence (SEQ ID NO: 59)

```
                                         -35                                                -10
rrnIp2   (1) GCTGATAAACAGCTGACATCAACTAAAAGCTTCATTAAATACTTTGAAAAAAGTTGTTGACTTAAAAGAAGCTAAATGTTATAGTAATAAA  (91)
rrnIp2-3 (1) GCTGATAAACAGCTGACATCAACTAAAAGTTTCATTAAATACTTTGAAAAAAGTTGTTGACTTAAAAGAAGCTAAATGTTATAGTAATAAA  (91)
```

Native *rrnIp2* Promoter Sequence (†) SEQ ID NO: 39 and Complementary Promoter Sequence (‡) SEQ ID NO: 60

*rrnIp2*⁺ GCTGATAAACAGCTGACATCAACTAAAAGCTTCATTAAATACTTTGAAAAAAGTTGTTGACTTAAAAGAAGCTAAATGTTATAGTAATAAAA
*rrnIp2*⁻ CGACTATTGTCGACTGTAGTTGATTTTCGAAGTAATTTATGAAACTTTTTCAACAACTGAATTTTCTTCGATTTACAATATCATTATTT

FIG. 2A

Novel *rrnIp2-1* Promoter Sequence (†) SEQ ID NO: 40 and Complementary Promoter Sequence (‡) SEQ ID NO: 61

*rrnIp2-1*⁺ GCTGATAAACAGCTGACATCAACTAAAAGTTCATTAAATACTTTGAAAAAAGTTGTTGACTTAAAGAAGCTAAATGTTATAGTAATTGT
*rrnIp2-1*⁻ CGACTATTTGTCGACTGTAGTTGATTTCAAAGTAATTTATGAAACTTTTTCAACAACTGAATTTCTTCGATTTACAATATCATTAACA

FIG. 2B

Novel *rrnIp2-2* Promoter Sequence (†) SEQ ID NO: 58 and Complementary Promoter Sequence (‡) SEQ ID NO: 62

*rrnIp2-2*⁺ GCTGATAAACAGCTGACATCAACTAAAAGCTTCATTAAATACTTTGAAAAAAGTTGTTGACTTAAAAGAAGCTAAATGTTATAGTAATTGT
*rrnIp2-2*⁻ CGACTATTTGTCGACTGTAGTTGATTTTCGAAGTAATTTATGAAACTTTTTTCAACAACTGAATTTTCTTCGATTTACAATATCATTAACA

FIG. 2C

Novel *rrnIp2-3* Promoter Sequence (†) SEQ ID NO: 59 and Complementary Promoter Sequence (‡) SEQ ID NO: 63

*rrnIp2-3*⁺ GCTGATAAACAGCTGACATCAACTAAAAGTTCATTAAATACTTTGAAAAAAGTTGTTGACTTAAAAGAAGCTAAATGTTATAGTAATAAA
*rrnIp2-3*⁻ CGACTATTTGTCGACTGTAGTTGATTTCAAAGTAATTTATGAAACTTTTTCAACAACTGAATTTTCTTCGATTTACAATATCATTATTT

Native *B. licheniformis amyL* Promoter Region (*PamyL-1*; SEQ ID NO: 64)
Aligned with Synthetic *amyL* Promoter Region (*PamyL-2*; SEQ ID NO: 65)

*PamyL-1* (SEQ ID NO: 64)

-35                                              -10
GCTTTTCTTTTGGAAGAAAATATAGGGAAAATGGTACTTGTTAAAAATTCGGAATATATTTATACAATATCATTAATGTTTCACATTGAAAGGGGAGGAGAATC

GCTTTTCTTTTGGAAGAAAATATAGGGAAAATGGTACTTGTTAAAAATTCGGAATATATTTATACAATATCATTATGTTTTCACATTGAAAGGGGAGGAGAATC

*PamyL-2* (SEQ ID NO: 65)

FIG. 3

Native *B. licheniformis amyL* Promoter Sequence (SEQ ID NO: 82)
Aligned with Synthetic *amyL* Promoter Sequence (SEQ ID NO: 83)

*PamyL*-1 (SEQ ID NO: 82)

(1) GCTTTTCTTTTGGAAGAAAATATAGGGAAAATGGTACTTGTTAAAAATTCGGAATATTTATACAATATCATAATG (74)

(1) GCTTTTCTTTTGGAAGAAAATATAGGGAAAATGGTACTTGTTAAAAATTCGGAATATTTATACAATATCATTGT (74)

*PamyL*-2 (SEQ ID NO: 83)

FIG. 4

Synthetic *amyL* Promoter Region Sequence (*PamyL-3*; SEQ ID NO: 66) Aligned
with Synthetic Promoter Region Sequence (*PamyL-4*; SEQ ID NO: 67)

*PamyL-3* (SEQ ID NO: 66)

(1) GCTTTTCTTTGGAAGAAAATATAGGGAAAATGGTACTTGTTAAAAATTCGGAATATTTATACAATATCATATGACAGAATAGTCTTTTAAGTAA

*PamyL-4* (SEQ ID NO: 67)

(1) GCTTTTCTTTGGAAGAAAATATAGGGAAAATGGTACTTGTTAAAAATTCGGAATATTTATACAATATCATTGTACAGAATAGTCTTTTAAGTAA

*PamyL-3* (SEQ ID NO: 66)

GTCTACTCTGAATTTTTTTAAAAGGAGAGGGTAAAGA (132)

*PamyL-4* (SEQ ID NO: 67)

GTCTACTCTGAATTTTTTTAAAAGGAGAGGGTAAAGA (132)

FIG. 5

SEQUENCE LISTING

```
<160> NUMBER OF SEQ ID NOS: 85

<210> SEQ ID NO 1
<211> LENGTH: 4188
<212> TYPE: DNA
<213> ORGANISM: Artificial Sequence
<220> FEATURE:
<223> OTHER INFORMATION: synthetic

<400> SEQUENCE: 1
gtggccccaa aaagaaacg  caaggttatg gataaaaaat acagcattgg tctggatatc      60
ggaaccaaca gcgttgggtg ggcagtaata acagatgaat acaaagtgcc gtcaaaaaaa     120
tttaaggttc tggggaatac agatcgccac agcataaaaa agaatctgat tgggcattg     180
```

-continued

```
ctgtttgatt cgggtgagac agctgaggcc acgcgtctga aacgtacagc aagaagacgt      240
tacacacgtc gtaaaaatcg tatttgctac ttacaggaaa ttttttctaa cgaaatggcc      300
aaggtagatg atagtttctt ccatcgtctc gaagaatctt ttctggttga ggaagataaa      360
aaacacgaac gtcaccctat ctttggcaat atcgtggatg aagtggccta tcatgaaaaa      420
taccctacga tttatcatct tcgcaagaag ttggttgata gtacggacaa agcggatctg      480
cgtttaatct atcttgcgtt agcgcacatg atcaaatttc gtggtcattt cttaattgaa      540
ggtgatctga atcctgataa ctctgatgtg gacaaattgt ttatacaatt agtgcaaacc      600
tataatcagc tgttcgagga aaaccccatt aatgcctctg gagttgatgc caaagcgatt      660
ttaagcgcga gactttctaa gtcccggcgt ctggagaatc tgatcgccca gttaccaggg      720
gaaaagaaaa atggtctgtt tggtaatctg attgccctca gtctggggct tacccccgaac     780 ttcaaatcca attttgacct ggctgaggac gcaaagctgc agctgagcaa agatacttat      840
gatgatgacc tcgacaatct gctcgcccag attggtgacc aatatgcgga tctgtttctg      900
gcagcgaaga atctttcgga tgctatcttg ctgtcggata ttctgcgtgt taataccgaa       960
atcaccaaag cgcctctgtc tgcaagtatg atcaagagat acgacgagca ccaccaggac     1020
ctgactcttc ttaaggcact ggtacgccaa cagcttccgg agaaatacaa agaaatattc     1080
ttcgaccagt ccaagaatgg ttacgcgggc tacatcgatg gtggtgcatc acaggaagag     1140
ttctataaat ttattaaacc aatccttgag aaaatggatg gcacggaaga gttacttgtt     1200
aaacttaacc gcgaagactt gcttagaaag caacgtacat tcgacaacgg ctccatccca     1260
caccagattc atttaggtga acttcacgcc atcttgcgca gacaagaaga tttctatccc     1320
ttcttaaaag acaatcggga gaaaatcgag aagatcctga cgttccgcat tccctattat     1380
gtcggtcccc tggcacgtgg taattctcgg tttgcctgga tgacgcgcaa aagtgaggaa     1440
accatcaccc cttggaactt tgaagaagtc gtggataaag gtgctagcgc gcagtctttt     1500
atagaaagaa tgacgaactt cgataaaaac ttgcccaacg aaaaagtcct gcccaagcac     1560 tctctttttat atgagtactt tactgtgtac aacgaactga ctaaagtgaa atacgttacg     1620
gaaggtatgc gcaaacctgc cttcttagt ggcgagcaga aaaaagcaat tgtcgatctt     1680
ctctttaaaa cgaatcgcaa ggtaactgta aaacagctga aggaagatta tttcaaaaag     1740
atcgaatgct ttgattctgt cgagatctcg ggtgtcgaag atcgtttcaa cgcttccttta    1800 gggacctatc atgatttgct gaagataata aaagacaaag actttctcga caatgaagaa    1860
aatgaagata ttctggagga tattgttttg accttgacct tattcgaaga tagagagatg    1920
atcgaggagc gcttaaaaac ctatgcccac ctgtttgatg acaaagtcat gaagcaatta    1980
aagcgccgca gatatacggg gtggggccgc ttgagccgca agttgattaa cggtattaga    2040
gacaagcaga gcggaaaaac tatcctggat ttcctcaaat ctgacggatt tgcgaaccgc    2100
aattttatgc agcttataca tgatgattcg cttacattca aagaggatat tcagaaggct    2160
caggtgtctg ggcaaggtga ttcactccac gaacatatag caaatttggc cggctctcct    2220
gcgattaaga aggggatcct gcaaacagtt aaagttgtgg atgaacttgt aaaagtaatg    2280
ggccgccaca agccggagaa tatcgtgata gaaatggcgc gcgagaatca aacgacacaa    2340
aaaggtcaaa agaactcaag agagagaatg aagcgcattg aggaggggat aaaggaactt    2400
ggatctcaaa ttctgaaaga acatccagtt gaaaacactc agctgcaaaa tgaaaaattg    2460
tacctgtact acctgcagaa tggaagagac atgtacgtgg atcaggaatt ggatatcaat    2520
agactctcgg actatgacgt agatcacatt gtccctcaga gcttcctcaa ggatgattct    2580
```

-continued

```
atagataata aagtacttac gagatcggac aaaaatcgcg gtaaatcgga taacgtccca    2640
tcggaggaag tcgttaaaaa gatgaaaaac tattggcgtc aactgctgaa cgccaagctg    2700
atcacacagc gtaagtttga taatctgact aaagccgaac gcggtggtct tagtgaactc    2760
gataaagcag gatttataaa acggcagtta gtagaaacgc gccaaattac gaaacacgtg    2820
gctcagatcc tcgattctag aatgaataca agtacgatg aaaacgataa actgatccgt     2880
gaagtaaaaa tcattacctt aaaatctaaa cttgtgtccg atttccgcaa agattttcag    2940
ttttacaagg tccgggaaat caataactat caccatgcac atgatgcata tttaaatgcg    3000
gttgtaggca cggcccttat taagaaatac cctaaactcg aaagtgagtt tgtttatggg    3060
gattataaag tgtatgacgt tcgcaaaatg atcgcgaaat cagaacagga aatcggtaag    3120
gctaccgcta aatactttt ttattccaac attatgaatt tttttaagac cgaaataact     3180
ctcgcgaatg gtgaaatccg taaacggcct cttatagaaa ccaatggtga acgggagaa    3240 atcgtttggg ataaaggtcg tgactttgcc accgttcgta aagtcctctc aatgccgcaa   3300
gttaacattg tcaagaagac ggaagttcaa acaggggat tctccaaaga atctatcctg    3360
ccgaagcgta acagtgataa acttattgcc agaaaaaaag attgggatcc aaaaaaatac    3420
ggaggctttg attcccctac cgtcgcgtat agtgtgctgg tggttgctaa agtcgagaaa    3480
gggaaaagca agaaattgaa atcagttaaa gaactgctgg gtattacaat tatgggaaga    3540
tcgtcctttg agaaaaatcc gatcgacttt ttagaggcca aggggtataa ggaagtgaaa    3600
aaagatctca tcatcaaatt accgaagtat agtcttttg agctggaaaa cggcagaaaa     3660
agaatgctgg cctccgcggg cgagttacag aagggaaatg agctggcgct gccttccaaa    3720
tatgttaatt ttctgtacct tgccagtcat tatgagaaac tgaagggcag ccccgaagat    3780
aacgaacaga aacaattatt cgtggaacag cataagcact atttagatga aattatagag    3840
caaattagtg aattttctaa gcgcgttatc ctcgcggatg ctaatttaga caaagtactg    3900
tcagcttata ataaacatcg ggataagccg attagagaac aggccgaaaa tatcattcat    3960
ttgtttacct taaccaacct tggagcacca gctgccttca aatatttcga taccacaatt    4020
gatcgtaaac ggtatacaag tacaaaagaa gtcttggacg caaccctcat tcatcaatct    4080
attactggat tatatgagac acgcattgat cttttcacagc tgggcggaga caagaagaaa    4140
aaactgaaac tgcaccatca tcaccatcat catcaccatc attgataa                 4188
```

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Ala Pro Lys Lys Lys Arg Lys Val
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic

<400> SEQUENCE: 3

Lys Lys Lys Lys Leu Lys

<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

His His His His His His His His His His
1               5                   10

<210> SEQ ID NO 5
<211> LENGTH: 607
<212> TYPE: DNA
<213> ORGANISM: Bacillus subtilis

<400> SEQUENCE: 5

```
attcctccat tttcttctgc tatcaaaata acagactcgt gattttccaa acgagctttc      60
aaaaaagcct ctgccccttg caaatcggat gcctgtctat aaaattcccg atattggtta     120
aacagcggcg caatggcggc cgcatctgat gtctttgctt ggcgaatgtt catcttattt     180
cttcctccct ctcaataatt ttttcattct atccctttc tgtaaagttt attttcaga      240
atactttat catcatgctt tgaaaaaata tcacgataat atccattgtt ctcacgaag      300
cacacgcagg tcatttgaac gaatttttc gacaggaatt tgccgggact caggagcatt     360
taacctaaaa aagcatgaca tttcagcata atgaacattt actcatgtct attttcgttc     420
ttttctgtat gaaaatagtt atttcgagtc tctacggaaa tagcgagaga tgatatacct     480
aaatagagat aaaatcatct caaaaaaatg ggtctactaa aatattattc catctattac     540
aataaattca cagaatagtc ttttaagtaa gtctactctg aattttttta aaaggagagg     600
gtaacta                                                               607
```

<210> SEQ ID NO 6
<211> LENGTH: 50
<212> TYPE: DNA
<213> ORGANISM: Artificial Sequence
<220> FEATURE:
<223> OTHER INFORMATION: synthetic

<400> SEQUENCE: 6

```
atatatgagt aaacttggtc tgacagaatt cctccatttt cttctgctat                 50
```

<210> SEQ ID NO 7
<211> LENGTH: 35
<212> TYPE: DNA
<213> ORGANISM: Artificial Sequence
<220> FEATURE:
<223> OTHER INFORMATION: synthetic

<400> SEQUENCE: 7

```
tgcggccgcg aattcgatta cgaatgccgt ctccc                                 35
```

<210> SEQ ID NO 8
<211> LENGTH: 3290
<212> TYPE: DNA
<213> ORGANISM: Artificial Sequence
<220> FEATURE:
<223> OTHER INFORMATION: synthetic

<400> SEQUENCE: 8

```
gaattcgcgg ccgcacgcgt ccatggggat ccccgcgggt cgacctcgag agttacgcta      60
gggataacag ggtaatatag gagctccagt cggcttaaac cagttttcgc tggtgcgaaa     120
aaagagtgtc ttgtgacacc taaattcaaa atctatcggt cagatttata ccgatttgat     180
tttatatatt cttgaataac atacgccgag ttatcacata aaagcgggaa ccaatcataa     240
aatttaaact tcattgcata atccattaaa ctcttaaatt ctacgattcc ttgttcatca     300
ataaactcaa tcatttcttt aattaattta tatctatctg ttgttgtttt ctttaataat     360
tcattaacat ctacaccgcc ataaactatc atatcttctt tttgatattt aaatttatta     420
ggatcgtcca tgtgaagcat atatctcaca agacctttca cacttcctgc aatctgcgga     480
atagtcgcat tcaattcttc tgttaattat ttttatctgt tcataagatt tattaccctc     540
atacatcact agaatatgat aatgctcttt tttcatccta ccttctgtat cagtatccct     600
atcatgtaat ggagacacta caaattgaat gtgtaactct tttaaatact ctaaccactc     660
ggcttttgct gattctggat ataaaacaaa tgtccaatta cgtcctcttg aattttctt     720 gttttcagtt tcttttatta catttttcgct catgatataa taacggtgct aatacactta     780
acaaaattta gtcatagata ggcagcatgc cagtgctgtc tatctttttt tgtttaaaat     840
gcaccgtatt cctcctttgc atatttttt attagaatac cggttgcatc tgatttgcta     900
atattatatt tttctttgat tctatttaat atctcatttt cttctgttgt aagtcttaaa     960
gtaacagcaa cttttttctc ttcttttcta tctacaacta tcactgtacc tcccaacatc    1020 tgttttttc actttaacat aaaaaacaac cttttaacat taaaaaccca atatttattt    1080
atttgtttgg acaatggaca ctggacacct agggggggagg tcgtagtacc cccctatgtt    1140
ttctccccta aataacccca aaaatctaag aaaaaaagac ctcaaaaagg tctttaatta    1200
acatctcaaa tttcgcattt attccaattt ccttttttgcg tgtgatgcga gctcatcggc    1260
tccgtcgata ctatgttata cgccaacttt caaaacaact ttgaaaaagc tgttttctgg    1320
tatttaaggt tttagaatgc aaggaacagt gaattggagt tcgtcttgtt ataattagct    1380
tcttggggta tctttaaata ctgtagaaaa gaggaaggaa ataataaatg ctaaaatga    1440 gaatatcacc ggaattgaaa aaactgatcg aaaaataccg ctgcgtaaaa gatacggaag    1500
gaatgtctcc tgctaaggta tataagctgg tgggagaaaa tgaaaaccta tatttaaaaa    1560
tgacggacag ccggtatgaa gggaccacct atgatgtgga acgggaaaag gacatgatgc    1620
tatggctgga aggaaagctg cctgttccaa aggtcctgca ctttgaacgg catgatggct    1680
ggagcaatct gctcatgagt gaggccgatg gcgtcctttg ctcggaagag tatgaagatg    1740
aacaaagccc tgaaaagatt atcgagctgt atgcggagtg catcaggctc tttcactcca    1800
tcgacatatc ggattgtccc tatacgaata gcttagacag ccgcttagcc gaattggatt    1860
acttactgaa taacgatctg ccgatgtggg attgcgaaaa ctgggaagaa gacactccat    1920
ttaaagatcc gcgcgagctg tatgattttt taaagacgga aaagcccgaa gaggaacttg    1980
tcttttccca cggcgacctg ggagacagca acatctttgt gaaagatggc aaagtaagtg    2040
gctttattga tcttgggaga agcggcaggg cggacaagtg gtatgacatt gccttctgcg    2100
tccggtcgat cagggaggat atcggggaag aacagtatgt cgagctattt tttgacttac    2160
tggggatcaa gcctgattgg gagaaaataa aatattatat tttactggat gaattgttt    2220 agtgactgca gtgagatctg gtaatgactc tctagcttga ggcatcaaat aaaacgaaag    2280
gctcagtcga aagactgggc ctttcgtttt atctgttgtt tgtcggtgaa cgctctcctg    2340
agtaggacaa atccgccgct ctagctaagc agaaggccat cctgacggat ggcctttttg    2400
```

```
cgtttctaca aactcttgtt aactctagag ctgcctgccg cgtttcggtg atgaagatct    2460
tcccgatgat taattaattc agaacgctcg gttgccgccg ggcgtttttt atgaagcttc    2520
gttgctggcg ttttccata ggctccgccc ccctgacgag catcacaaaa atcgacgctc    2580
aagtcagagg tggcgaaacc cgacaggact ataaagatac caggcgtttc ccctggaag    2640 ctccctcgtg cgctctcctg ttccgaccct gccgcttacc ggatacctgt ccgcctttct    2700
cccttcggga agcgtggcgc tttctcatag ctcacgctgt aggtatctca gttcggtgta    2760
ggtcgttcgc tccaagctgg gctgtgtgca cgaaccccc gttcagcccg accgctgcgc     2820
cttatccggt aactatcgtc ttgagtccaa cccggtaaga cacgacttat cgccactggc    2880
agcagccact ggtaacagga ttagcagagc gaggtatgta ggcggtgcta cagagttctt    2940
gaagtggtgg cctaactacg gctacactag aaggacagta tttggtatct gcgctctgct    3000
gaagccagtt accttcggaa aaagagttgg tagctcttga tccggcaaac aaaccaccgc    3060
tggtagcggt ggtttttttg tttgcaagca gcagattacg cgcagaaaaa aaggatctca    3120
agaagatcct ttgatctttt ctacggggtc tgacgctcag tggaacgaaa actcacgtta    3180
agggattttg gtcatgagat tatcaaaaag gatcttcacc tagatccttt taaattaaaa    3240
atgaagtttt aaatcaatct aaagtatata tgagtaaact tggtctgaca                3290

<210> SEQ ID NO 9
<211> LENGTH: 4204
<212> TYPE: DNA
<213> ORGANISM: Artificial Sequence
<220> FEATURE:
<223> OTHER INFORMATION: synthetic

<400> SEQUENCE: 9
gcggccgcac gcgtccatgg ggatccccgc gggtcgacct cgagagttac gctagggata     60
acagggtaat ataggagctc cagtcggctt aaaccagttt tcgctggtgc gaaaaaagag    120
tgtcttgtga cacctaaatt caaaatctat cggtcagatt tataccgatt tgatttata    180 tattcttgaa taacatacgc cgagttatca cataaaagcg ggaaccaatc ataaaattta    240
aacttcattg cataatccat taaactctta aattctacga ttccttgttc atcaataaac    300
tcaatcattt ctttaattaa tttatatcta tctgttgttg ttttctttaa taattcatta    360
acatctacac cgccataaac tatcatatct tcttttgat atttaaattt attaggatcg    420
tccatgtgaa gcatatatct cacaagacct ttcacacttc ctgcaatctg cggaatagtc    480
gcattcaatt cttctgttaa ttatttttat ctgttcataa gatttattac cctcatacat    540
cactagaata tgataatgct cttttttcat cctaccttct gtatcagtat ccctatcatg    600
taatggagac actacaaatt gaatgtgtaa ctctttttaaa tactctaacc actcggcttt    660
tgctgattct ggatataaaa caaatgtcca attacgtcct cttgaatttt tcttgttttc    720
agtttctttt attacatttt cgctcatgat ataataacgg tgctaataca cttaacaaaa    780
tttagtcata gataggcagc atgccagtgc tgtctatctt ttttgttta aaatgcaccg    840 tattcctcct ttgcatattt ttttattaga ataccggttg catctgattt gctaatatta    900 tattttctt tgattctatt taatatctca ttttcttctg ttgtaagtct taaagtaaca    960 gcaactttt tctcttcttt tctatctaca actatcactg tacctcccaa catctgtttt    1020
tttcacttta acataaaaaa caaccttta acattaaaaa cccaatattt atttatttgt    1080
ttggacaatg gacactggac acctagggggg gaggtcgtag tacccccta tgttttctcc    1140
```

```
cctaaataac cccaaaaatc taagaaaaaa agacctcaaa aaggtctttta attaacatct    1200 caaatttcgc atttattcca atttcctttt tgcgtgtgat gcgagctcat cggctccgtc    1260
gatactatgt tatacgccaa cttcaaaac aactttgaaa aagctgtttt ctggtattta    1320
aggttttaga atgcaaggaa cagtgaattg gagttcgtct tgttataatt agcttcttgg    1380
ggtatcttta aatactgtag aaaagaggaa ggaaataata aatggctaaa atgagaatat    1440
caccggaatt gaaaaaactg atcgaaaaat accgctgcgt aaaagatacg gaaggaatgt    1500
ctcctgctaa ggtatataag ctggtgggag aaaatgaaaa cctatattta aaaatgacgg    1560
acagccggta taagggacc acctatgatg tggaacggga aaaggacatg atgctatggc    1620
tggaaggaaa gctgcctgtt ccaaaggtcc tgcactttga acggcatgat ggctggagca    1680
atctgctcat gagtgaggcc gatggcgtcc tttgctcgga agagtatgaa gatgaacaaa    1740
gccctgaaaa gattatcgag ctgtatgcgg agtgcatcag gctctttcac tccatcgaca    1800
tatcggattg tccctatacg aatagcttag acagccgctt agccgaattg gattacttac    1860
tgaataacga tctggccgat gtggattgcg aaaactggga agaagacact ccatttaaag    1920
atccgcgcga gctgtatgat tttttaaaga cggaaaagcc cgaagaggaa cttgtctttt    1980 cccacgcgcga cctgggagac agcaacatct ttgtgaaaga tggcaaagta agtggcttta    2040
ttgatcttgg gagaagcggc agggcggaca agtggtatga cattgccttc tgcgtccggt    2100
cgatcaggga ggatatcggg gaagaacagt atgtcgagct attttttgac ttactgggga    2160
tcaagcctga ttgggagaaa ataaaatatt atattttact ggatgaattg ttttagtgac    2220
tgcagtgaga tctggtaatg actctctagc ttgaggcatc aaataaaacg aaaggctcag    2280
tcgaaagact gggcctttcg ttttatctgt tgtttgtcgg tgaacgctct cctgagtagg    2340
acaaatccgc cgctctagct aagcagaagg ccatcctgac ggatggcctt tttgcgtttc    2400
tacaaactct tgttaactct agagctgcct gccgcgtttc ggtgatgaag atcttcccga    2460
tgattaatta attcagaacg ctcggttgcc gccgggcgtt ttttatgaag cttcgttgct    2520 ggcgttttc cataggctcc gcccccctga cgagcatcac aaaaatcgac gctcaagtca    2580
gaggtggcga aacccgacag gactataaag ataccaggcg tttccccctg gaagctccct    2640
cgtgcgctct cctgttccga ccctgccgct taccggatac ctgtccgcct ttctcccttc    2700
gggaagcgtg cgctttctc atagctcacg ctgtaggtat ctcagttcgg tgtaggtcgt    2760
tcgctccaag ctgggctgtg tgcacgaacc ccccgttcag cccgaccgct gcgccttatc    2820
cggtaactat cgtcttgagt ccaacccggt aagacacgac ttatcgccac tggcagcagc    2880
cactggtaac aggattagca gagcgaggta tgtaggcggt gctacagagt tcttgaagtg    2940
gtggcctaac tacggctaca ctagaaggac agtatttggt atctgcgctc tgctgaagcc    3000
agttaccttc ggaaaaagag ttggtagctc ttgatccggc aaacaaacca ccgctggtag    3060
cggtggtttt tttgtttgca agcagcagat tacgcgcaga aaaaaaggat ctcaagaaga    3120
tcctttgatc ttttctacgg ggtctgacgc tcagtggaac gaaaactcac gttaagggat    3180
tttggtcatg agattatcaa aaaggatctt cacctagatc cttttaaatt aaaaatgaag    3240
ttttaaatca atctaaagta tatatgagta aacttggtct gacagttacc aatgcttaat    3300
cagtgaggca cctatctcag cgatctgtct atttcgttca tccatagttg cctgactccc    3360
cgtcgtgtag ataactacga tacgggaggg cttaccatct ggccccagtg ctgcaatgat    3420
accgcgagac ccacgctcac cggctccaga tttatcagca ataaaccagc cagccggaag    3480
ggccgagcgc agaagtggtc ctgcaacttt atccgcctcc atccagtcta ttaattgttg    3540
```

```
ccgggaagct agagtaagta gttcgccagt taatagtttg cgcaacgttg ttgccattgc    3600
tacaggcatc gtggtgtcac gctcgtcgtt tggtatggct tcattcagct ccggttccca    3660
acgatcaagg cgagttacat gatcccccat gttgtgcaaa aaagcggtta gctccttcgg    3720
tcctccgatc gttgtcagaa gtaagttggc cgcagtgtta tcactcatgg ttatggcagc    3780
actgcataat tctcttactg tcatgccatc cgtaagatgc ttttctgtga ctggtgagta    3840
ctcaaccaag tcattctgag aatagtgtat gcggcgaccg agttgctctt gcccggcgtc    3900
aatacgggat aataccgcgc cacatagcag aactttaaaa gtgctcatca ttggaaaacg    3960
ttcttcgggg cgaaaactct caaggatctt accgctgttg agatccagtt cgatgtaacc    4020
cactcgtgca cccaactgat cttcagcatc ttttactttc accagcgttt ctgggtgagc    4080
aaaaacagga aggcaaaatg ccgcaaaaaa gggaataagg gcgacacgga aatgttgaat    4140
actcatactc ttcctttttc aatattattg aagcatttat cagggttatt gtctcatgga    4200
attc                                                                 4204
```

<210> SEQ ID NO 10
<211> LENGTH: 35
<212> TYPE: DNA
<213> ORGANISM: Artificial Sequence
<220> FEATURE:
<223> OTHER INFORMATION: synthetic

<400> SEQUENCE: 10
gggagacggc attcgtaatc gaattcgcgg ccgca                               35

<210> SEQ ID NO 11
<211> LENGTH: 50
<212> TYPE: DNA
<213> ORGANISM: Artificial Sequence
<220> FEATURE:
<223> OTHER INFORMATION: synthetic

<400> SEQUENCE: 11
atagcagaag aaaatggagg aattctgtca gaccaagttt actcatatat              50

<210> SEQ ID NO 12
<211> LENGTH: 23
<212> TYPE: DNA
<213> ORGANISM: Artificial Sequence
<220> FEATURE:
<223> OTHER INFORMATION: synthetic

<400> SEQUENCE: 12
ccgactggag ctcctatatt acc                                            23

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
gctgtggcga tctgtattcc                                                20

<210> SEQ ID NO 14
<211> LENGTH: 22
<212> TYPE: DNA
<213> ORGANISM: Artificial Sequence
<220> FEATURE:

<223> OTHER INFORMATION: synthetic

<400> SEQUENCE: 14
gtcttttaag taagtctact ct                                              22

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
ccaaagcgat tttaagcgcg                                                 20

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
cctggcacgt ggtaattctc                                                 20

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
ggatttcctc aaatctgacg                                                 20

<210> SEQ ID NO 18
<211> LENGTH: 21
<212> TYPE: DNA
<213> ORGANISM: Artificial Sequence
<220> FEATURE:
<223> OTHER INFORMATION: synthetic

<400> SEQUENCE: 18
gtagaaacgc gccaaattac g                                               21

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
gctggtggtt gctaaagtcg                                                 20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
ggacgcaacc ctcattcatc                                                 20

<210> SEQ ID NO 21
<211> LENGTH: 8347
<212> TYPE: DNA
<213> ORGANISM: Artificial Sequence
<220> FEATURE:
<223> OTHER INFORMATION: synthetic

<400> SEQUENCE: 21

| | | | | | |
|---|---|---|---|---|---|
| gaattcctcc | attttcttct | gctatcaaaa | taacagactc | gtgattttcc aaacgagctt | 60 |
| tcaaaaaagc | ctctgcccct | tgcaaatcgg | atgcctgtct | ataaaattcc cgatattggt | 120 |
| taaacagcgg | cgcaatggcg | gccgcatctg | atgtctttgc | ttggcgaatg ttcatcttat | 180 |
| ttcttcctcc | ctctcaataa | ttttttcatt | ctatccctt | tctgtaaagt ttattttca | 240 |
| gaatactttt | atcatcatgc | tttgaaaaaa | tatcacgata | atatccattg ttctcacgga | 300 |
| agcacacgca | ggtcatttga | acgaattttt | tcgacaggaa | tttgccggga ctcaggagca | 360 |
| tttaacctaa | aaaagcatga | catttcagca | taatgaacat | ttactcatgt ctattttcgt | 420 |
| tcttttctgt | atgaaaatag | ttatttcgag | tctctacgga | aatagcgaga gatgatatac | 480 |
| ctaaatagag | ataaaatcat | ctcaaaaaaa | tgggtctact | aaaatattat tccatctatt | 540 |
| acaataaatt | cacagaatag | tcttttaagt | aagtctactc | tgaatttttt taaaaggaga | 600 |
| gggtaactag | tggccccaaa | aaagaaacgc | aaggttatgg | ataaaaaata cagcattggt | 660 |
| ctggatatcg | gaaccaacag | cgttgggtgg | gcagtaataa | cagatgaata caaagtgccg | 720 |
| tcaaaaaat | ttaaggttct | ggggaataca | gatcgccaca | gcataaaaaa gaatctgatt | 780 |
| ggggcattgc | tgtttgattc | gggtgagaca | gctgaggcca | cgcgtctgaa acgtacagca | 840 |
| agaagacgtt | acacacgtcg | taaaaatcgt | atttgctact | tacaggaaat ttttctaac | 900 |
| gaaatggcca | aggtagatga | tagttttcttc | catcgtctcg | aagaatcttt tctggttgag | 960 |
| gaagataaaa | aacacgaacg | tcaccctatc | tttggcaata | tcgtggatga agtggcctat | 1020 |
| catgaaaaat | accctacgat | ttatcatctt | cgcaagaagt | tggttgatag tacggacaaa | 1080 |
| gcggatctgc | gtttaatcta | tcttgcgtta | gcgcacatga | tcaaatttcg tggtcatttc | 1140 |
| ttaattgaag | gtgatctgaa | tcctgataac | tctgatgtgg | acaaattgtt tatacaatta | 1200 |
| gtgcaaacct | ataatcagct | gttcgaggaa | aaccccatta | atgcctctgg agttgatgcc | 1260 |
| aaagcgattt | taagcgcgag | actttctaag | tcccggcgtc | tggagaatct gatcgcccag | 1320 |
| ttaccagggg | aaaagaaaaa | tggtctgttt | ggtaatctga | ttgccctcag tctgggcgctt | 1380 |
| accccgaact | tcaaatccaa | ttttgacctg | gctgaggacg | caaagctgca gctgagcaaa | 1440 |
| gatacttatg | atgatgacct | cgacaatctg | ctcgcccaga | ttggtgacca atatgcggat | 1500 |
| ctgtttctgg | cagcgaagaa | tctttcggat | gctatcttgc | tgtcggatat tctgcgtgtt | 1560 |
| aataccgaaa | tcaccaaagc | gcctctgtct | gcaagtatga | tcaagagata cgacgagcac | 1620 |
| caccaggacc | tgactcttct | taaggcactg | gtacgccaac | agcttccgga gaaatacaaa | 1680 |
| gaaatattct | tcgaccagtc | caagaatggt | tacgcgggct | acatcgatgg tggtgcatca | 1740 |
| caggaagagt | tctataaatt | tattaaacca | atccttgaga | aatggatgg cacggaagag | 1800 |
| ttacttgtta | aacttaaccg | cgaagacttg | cttagaaagc | aacgtacatt cgacaacggc | 1860 |
| tccatcccac | accagattca | tttaggtgaa | cttcacgcca | tcttgcgcag acaagaagat | 1920 |
| ttctatccct | tcttaaaaga | caatcgggag | aaaatcgaga | agatcctgac gttccgcatt | 1980 |
| ccctattatg | tcggtcccct | ggcacgtggt | aattctcggt | ttgcctggat gacgcgcaaa | 2040 |
| agtgaggaaa | ccatcacccc | ttggaacttt | gaagaagtcg | tggataaagg tgctagcgcg | 2100 |

```
cagtctttta tagaaagaat gacgaacttc gataaaaact tgcccaacga aaaagtcctg    2160
cccaagcact ctctttata tgagtacttt actgtgtaca acgaactgac taaagtgaaa    2220
tacgttacgg aaggtatgcg caaacctgcc tttcttagtg gcgagcagaa aaaagcaatt    2280
gtcgatcttc tctttaaaac gaatcgcaag gtaactgtaa aacagctgaa ggaagattat    2340
ttcaaaaaga tcgaatgctt tgattctgtc gagatctcgg gtgtcgaaga tcgtttcaac    2400
gcttccttag ggacctatca tgatttgctg aagataataa aagacaaaga ctttctcgac    2460
aatgaagaaa atgaagatat tctggaggat attgttttga ccttgacctt attcgaagat    2520
agagagatga tcgaggagcg cttaaaaacc tatgcccacc tgtttgatga caaagtcatg    2580
aagcaattaa agcgccgcag atatacgggg tggggccgct tgagccgcaa gttgattaac    2640
ggtattagag acaagcagag cggaaaaact atcctggatt tcctcaaatc tgacggattt    2700
gcgaaccgca attttatgca gcttatacat gatgattcgc ttacattcaa agaggatatt    2760
cagaaggctc aggtgtctgg gcaaggtgat tcactccacg aacatatagc aaatttggcc    2820
ggctctcctg cgattaagaa ggggatcctg caaacagtta agttgtgga tgaacttgta    2880 aaagtaatgg gccgccacaa gccggagaat atcgtgatag aaatggcgcg cgagaatcaa    2940
acgacacaaa aaggtcaaaa gaactcaaga gagaatgaa agcgcattga ggaggggata    3000
aaggaacttg gatctcaaat tctgaaagaa catccagttg aaaacactca gctgcaaaat    3060
gaaaaattgt acctgtacta cctgcagaat ggaagagaca tgtacgtgga tcaggaattg    3120
gatatcaata gactctcgga ctatgacgta gatcacattg ccctcagag cttcctcaag    3180 gatgattcta tagataataa agtacttacg agatcggaca aaaatcgcgg taaatcggat    3240
aacgtcccat cggaggaagt cgttaaaaag atgaaaaact attggcgtca actgctgaac    3300
gccaagctga tcacacagcg taagtttgat aatctgacta agccgaacg cggtggtctt    3360 agtgaactcg ataaagcagg atttataaaa cggcagttag tagaaacgcg ccaaattacg    3420
aaacacgtgg ctcagatcct cgattctaga atgaatacaa agtacgatga aaacgataaa    3480
ctgatccgtg aagtaaaagt cattacctta aaatctaaac ttgtgtccga tttccgcaaa    3540
gattttcagt tttacaaggt ccgggaaatc aataactatc accatgcaca tgatgcatat    3600
ttaaatgcgg ttgtaggcac ggcccttatt aagaaatacc ctaaactcga agtgagttt    3660 gtttatgggg attataaagt gtatgacgtt cgcaaaatga tcgcgaaatc agaacaggaa    3720
atcggtaagg ctaccgctaa atactttttt tattccaaca ttatgaattt ttttaagacc    3780
gaaataactc tcgcgaatgg tgaaatccgt aaacggcctc ttatagaaac caatggtgaa    3840
acgggagaaa tcgtttggga taaaggtcgt gactttgcca ccgttcgtaa agtcctctca    3900
atgccgcaag ttaacattgt caagaagacg gaagttcaaa caggggattt ctccaaagaa    3960
tctatcctgc cgaagcgtaa cagtgataaa cttattgcca gaaaaaaaga ttgggatcca    4020
aaaaaatacg gaggctttga ttcccctacc gtcgcgtata gtgtgctggt ggttgctaaa    4080
gtcgagaaag ggaaagcaa gaaattgaaa tcagttaaag aactgctggg tattacaatt    4140
atggaaagat cgtcctttga gaaaaatccg atcgactttt tagaggccaa ggggtataag    4200
gaagtgaaaa aagatctcat catcaaatta ccgaagtata gtcttttttga gctgaaaac    4260 ggcagaaaaa gaatgctggc ctccgcgggc gagttacaga agggaaatga gctggcgctg    4320
ccttccaaat atgttaattt tctgtacctt gccagtcatt atgagaaact gaagggcagc    4380
cccgaagata acgaacagaa acaattattc gtggaacagc ataagcacta tttagatgaa    4440
attatagagc aaaattagtga attttctaag cgcgttatcc tcgcggatgc taatttagac    4500
```

```
aaagtactgt cagcttataa taaacatcgg gataagccga ttagagaaca ggccgaaaat    4560
atcattcatt tgtttacctt aaccaacctt ggagcaccag ctgccttcaa atatttcgat    4620
accacaattg atcgtaaacg gtatacaagt acaaaagaag tcttggacgc aaccctcatt    4680
catcaatcta ttactggatt atatgagaca cgcattgatc tttcacagct gggcggagac    4740
aagaagaaaa aactgaaact gcaccatcat caccatcatc atcaccatca ttgataactc    4800
gagaaagctt acataaaaaa ccggccttgg ccccgccggt tttttattat ttttcttcct    4860
ccgcatgttc aatccgctcc ataatcgacg gatggctccc tctgaaaatt taacgagaa    4920 acggcgggtt gacccggctc agtcccgtaa cggccaagtc ctgaaacgtc tcaatcgccg    4980
cttcccggtt tccggtcagc tcaatgccgt aacggtcggc ggcgttttcc tgataccggg    5040
agacggcatt cgtaatcgaa ttcgcggccg cacgcgtcca tggggatccc cgcgggtcga    5100
cctcgagagt tacgctaggg ataacagggt aatataggag ctccagtcgg cttaaaccag    5160
ttttcgctgg tgcgaaaaaa gagtgtcttg tgacacctaa attcaaaatc tatcggtcag    5220
atttataccg atttgatttt atatattctt gaataacata cgccgagtta tcacataaaa    5280
gcgggaacca atcataaaat ttaaacttca ttgcataatc cattaaactc ttaaattcta    5340
cgattccttg ttcatcaata aactcaatca tttctttaat taatttatat ctatctgttg    5400
ttgttttctt taataattca ttaacatcta caccgccata aactatcata tcttcttttt    5460
gatatttaaa tttattagga tcgtccatgt gaagcatata tctcacaaga cctttcacac    5520
ttcctgcaat ctgcggaata gtcgcattca attcttctgt taattatttt tatctgttca    5580
taagatttat taccctcata catcactaga atatgataat gctctttttt catcctacct    5640
tctgtatcag tatccctatc atgtaatgga gacactacaa attgaatgtg taactctttt    5700
aaatactcta accactcggc ttttgctgat tctggatata aaacaaatgt ccaattacgt    5760
cctcttgaat ttttcttgtt ttcagtttct tttattacat tttcgctcat gatataataa    5820
cggtgctaat acacttaaca aaatttagtc atagataggc agcatgccag tgctgtctat    5880 cttttttgt ttaaaatgca ccgtattcct cctttgcata ttttttttatt agaataccgg    5940 ttgcatctga tttgctaata ttatattttt ctttgattct atttaatatc tcattttctt    6000
ctgttgtaag tcttaaagta acagcaactt ttttctcttc ttttctatct acaactatca    6060
ctgtacctcc caacatctgt tttttcact ttaacataaa aaacaacctt ttaacattaa    6120
aaacccaata tttatttatt tgtttggaca atggacactg gacacctagg ggggaggtcg    6180
tagtaccccc ctatgttttc tcccctaaat aaccccaaaa atctaagaaa aaagacctc    6240 aaaaaggtct ttaattaaca tctcaaattt cgcatttatt ccaatttcct ttttgcgtgt    6300
gatgcgagct catcggctcc gtcgatacta tgttatacgc caacttcaa aacaactttg    6360 aaaaagctgt tttctggtat ttaaggtttt agaatgcaag gaacagtgaa ttggagttcg    6420
tcttgttata attagcttct tggggtatct ttaaatactg tagaaaagag gaaggaaata    6480
ataaatggct aaaatgagaa tatcaccgga attgaaaaaa ctgatcgaaa aataccgctg    6540
cgtaaaagat acggaaggaa tgtctcctgc taaggtatat aagctggtgg gagaaaatga    6600
aaacctatat ttaaaaatga cggacagccg gtataaaggg accacctatg atgtggaacg    6660 ggaaaggac atgatgctat ggctggaagg aaagctgcct gttccaaagg tcctgcactt    6720
tgaacggcat gatggctgga gcaatctgct catgagtgag gccgatggcg tccttttgctc    6780 ggaagagtat gaagatgaac aaagccctga aaagattatc gagctgtatg cggagtgcat    6840
```

```
caggctcttt cactccatcg acatatcgga ttgtccctat acgaatagct tagacagccg    6900
cttagccgaa ttggattact tactgaataa cgatctggcc gatgtggatt gcgaaaactg    6960
ggaagaagac actccattta aagatccgcg cgagctgtat gatttttta agacggaaaa    7020
gcccgaagag gaacttgtct tttcccacgg cgacctggga gacagcaaca tctttgtgaa    7080
agatggcaaa gtaagtggct ttattgatct tgggagaagc ggcagggcgg acaagtggta    7140
tgacattgcc ttctgcgtcc ggtcgatcag ggaggatatc ggggaagaac agtatgtcga    7200
gctattttt gacttactgg ggatcaagcc tgattgggag aaaataaaat attatatttt    7260
actggatgaa ttgttttagt gactgcagtg agatctggta atgactctct agcttgaggc    7320
atcaaataaa acgaaaggct cagtcgaaag actgggcctt tcgttttatc tgttgtttgt    7380
cggtgaacgc tctcctgagt aggacaaatc cgccgctcta gctaagcaga aggccatcct    7440
gacggatggc cttttgcgt ttctacaaac tcttgttaac tctagagctg cctgccgcgt    7500
ttcggtgatg aagatcttcc cgatgattaa ttaattcaga acgctcggtt gccgccgggc    7560
gttttttatg aagcttcgtt gctggcgttt ttccataggc tccgcccccc tgacgagcat    7620
cacaaaaatc gacgctcaag tcagaggtgg cgaaacccga caggactata aagataccag    7680
gcgtttcccc ctggaagctc cctcgtgcgc tctcctgttc cgaccctgcc gcttaccgga    7740
tacctgtccg cctttctccc ttcgggaagc gtggcgcttt ctcatagctc acgctgtagg    7800
tatctcagtt cggtgtaggt cgttcgctcc aagctgggct gtgtgcacga accccccgtt    7860
cagcccgacc gctgcgcctt atccggtaac tatcgtcttg agtccaaccc ggtaagacac    7920
gacttatcgc cactggcagc agccactggt aacaggatta gcagagcgag gtatgtaggc    7980
ggtgctacag agttcttgaa gtggtggcct aactacggct acactagaag gacagtattt    8040
ggtatctgcg ctctgctgaa gccagttacc ttcggaaaaa gagttggtag ctcttgatcc    8100
ggcaaacaaa ccaccgctgg tagcggtggt ttttttgttt gcaagcagca gattacgcgc    8160
agaaaaaaag gatctcaaga agatcctttg atcttttcta cggggtctga cgctcagtgg    8220
aacgaaaact cacgttaagg gattttggtc atgagattat caaaaaggat cttcacctag    8280
atcctttaa attaaaaatg aagttttaaa tcaatctaaa gtatatatga gtaaacttgg    8340
tctgaca                                                              8347
```

<210> SEQ ID NO 22
<211> LENGTH: 9286
<212> TYPE: DNA
<213> ORGANISM: Artificial Sequence
<220> FEATURE:
<223> OTHER INFORMATION: synthetic

<400> SEQUENCE: 22

```
gaattcctcc atttcttct gctatcaaaa taacagactc gtgattttcc aaacgagctt      60
tcaaaaaagc ctctgcccct tgcaaatcgg atgcctgtct ataaaattcc cgatattggt     120
taaacagcgg cgcaatggcg gccgcatctg atgtctttgc ttggcgaatg ttcatcttat     180
ttcttcctcc ctctcaataa tttttttcatt ctatcccttt tctgtaaagt ttattttca    240
gaatactttt atcatcatgc tttgaaaaaa tatcacgata atatccattg ttctcacgga     300
agcacacgca ggtcatttga acgaatttt tcgacaggaa tttgccggga ctcaggagca     360
tttaacctaa aaaagcatga catttcagca taatgaacat ttactcatgt ctatttcgt    420
tcttttctgt atgaaaatag ttatttcgag tctctacgga aatagcgaga gatgatatac     480
ctaaatagag ataaaatcat ctcaaaaaaa tgggtctact aaaatattat tccatctatt     540
```

| | |
|---|---|
| acaataaatt cacagaatag tcttttaagt aagtctactc tgaatttttt taaaaggaga | 600 |
| gggtaactag tggccccaaa aaagaaacgc aaggttatgg ataaaaaata cagcattggt | 660 |
| ctggatatcg gaaccaacag cgttgggtgg gcagtaataa cagatgaata caaagtgccg | 720 |
| tcaaaaaaat ttaaggttct ggggaataca gatcgccaca gcataaaaaa gaatctgatt | 780 |
| ggggcattgc tgtttgattc gggtgagaca gctgaggcca cgcgtctgaa acgtacagca | 840 |
| agaagacgtt acacacgtcg taaaaatcgt atttgctact tacaggaaat tttttctaac | 900 |
| gaaatggcca aggtagatga tagtttcttc catcgtctcg aagaatcttt tctggttgag | 960 |
| gaagataaaa aacacgaacg tcaccctatc tttggcaata tcgtggatga agtggcctat | 1020 |
| catgaaaaat accctacgat ttatcatctt cgcaagaagt tggttgatag tacggacaaa | 1080 |
| gcggatctgc gtttaatcta tcttgcgtta gcgcacatga tcaaatttcg tggtcatttc | 1140 |
| ttaattgaag gtgatctgaa tcctgataac tctgatgtgg acaaattgtt tatacaatta | 1200 |
| gtgcaaacct ataatcagct gttcgaggaa acccccatta atgcctctgg agttgatgcc | 1260 |
| aaagcgattt taagcgcgag acttcctaag tcccggcgtc tggagaatct gatcgcccag | 1320 |
| ttaccagggg aaaagaaaaa tggtctgttt ggtaatctga ttgccctcag tctggggctt | 1380 |
| accccgaact tcaaatccaa ttttgacctg gctgaggacg caaagctgca gctgagcaaa | 1440 |
| gatacttatg atgatgacct cgacaatctg ctcgcccaga ttggtgacca atatgcggat | 1500 |
| ctgtttctgg cagcgaagaa tctttcggat gctatcttgc tgtcggatat tctgcgtgtt | 1560 |
| aataccgaaa tcaccaaagc gcctctgtct gcaagtatga tcaagagata cgacgagcac | 1620 |
| caccaggacc tgactcttct taaggcactg gtacgccaac agcttccgga gaaatacaaa | 1680 |
| gaaatattct tcgaccagtc caagaatggt tacgcgggct acatcgatgg tggtgcatca | 1740 |
| caggaagagt tctataaatt tattaaacca atccttgaga aaatggatgg cacggaagag | 1800 |
| ttacttgtta aacttaaccg cgaagacttg cttagaaagc aacgtacatt cgacaacggc | 1860 |
| tccatcccac accagattca tttaggtgaa cttcacgcca tcttgcgcag acaagaagat | 1920 |
| ttctatccct tcttaaaaga caatcgggag aaaatcgaga agatcctgac gttccgcatt | 1980 |
| ccctattatg tcggtcccct ggcacgtggt aattctcggt ttgcctggat gacgcgcaaa | 2040 |
| agtgaggaaa ccatcacccc ttggaacttt gaagaagtcg tggataaagg tgctagcgcg | 2100 |
| cagtctttta tagaaagaat gacgaacttc gataaaaact tgcccaacga aaaagtcctg | 2160 |
| cccaagcact ctcttttata tgagtacttt actgtgtaca acgaactgac taaagtgaaa | 2220 |
| tacgttacgg aaggtatgcg caaacctgcc tttcttagtg gcgagcagaa aaaagcaatt | 2280 |
| gtcgatcttc tctttaaaac gaatcgcaag gtaactgtaa aacagctgaa ggaagattat | 2340 |
| ttcaaaaaga tcgaatgctt tgattctgtc gagatctcgg gtgtcgaaga tcgtttcaac | 2400 |
| gcttccttag ggacctatca tgatttgctg aagataataa aagacaaaga ctttctcgac | 2460 |
| aatgaagaaa atgaagatat tctggaggat attgttttga ccttgacctt attcgaagat | 2520 |
| agagagatga tcgaggagcg cttaaaaacc tatgcccacc tgtttgatga caaagtcatg | 2580 |
| aagcaattaa agcgccgcag atatacgggg tggggccgct tgagccgcaa gttgattaac | 2640 |
| ggtattagag acaagcagag cggaaaaact atcctgaatt tcctcaaatc tgacggattt | 2700 |
| gcgaaccgca ttttatgca gcttatacat gatgattcgc ttacattcaa agaggatatt | 2760 |
| cagaaggctc aggtgtctgg gcaaggtgat tcactccacg aacatatagc aaatttggcc | 2820 |
| ggctctcctg cgattaagaa ggggatcctg caaacagtta agttgtgga tgaacttgta | 2880 |

```
aaagtaatgg gccgccacaa gccggagaat atcgtgatag aaatggcgcg cgagaatcaa    2940
acgacacaaa aaggtcaaaa gaactcaaga gagagaatga agcgcattga ggagggata     3000 aaggaacttg gatctcaaat tctgaaagaa catccagttg aaaacactca gctgcaaaat    3060
gaaaaattgt acctgtacta cctgcagaat ggaagagaca tgtacgtgga tcaggaattg    3120
gatatcaata gactctcgga ctatgacgta gatcacattg tccctcagag cttcctcaag    3180
gatgattcta tagataataa agtacttacg agatcggaca aaaatcgcgg taaatcggat    3240
aacgtcccat cggaggaagt cgttaaaaag atgaaaaact attggcgtca actgctgaac    3300
gccaagctga tcacacagcg taagtttgat aatctgacta aagccgaacg cggtggtctt    3360
agtgaactcg ataaagcagg atttataaaa cggcagttag tagaaacgcg ccaaattacg    3420
aaacacgtgg ctcagatcct cgattctaga atgaatacaa agtacgatga aaacgataaa    3480
ctgatccgtg aagtaaaagt cattacctta aaatctaaac ttgtgtccga tttccgcaaa    3540
gattttcagt tttacaaggt ccgggaaatc aataactatc accatgcaca tgatgcatat    3600
ttaaatgcgg ttgtaggcac ggcccttatt aagaaatacc ctaaactcga aagtgagttt    3660
gtttatgggg attataaagt gtatgacgtt cgcaaaatga tcgcgaaatc agaacaggaa    3720
atcggtaagg ctaccgctaa atactttttt tattccaaca ttatgaattt ttttaagacc    3780
gaaataactc tcgcgaatgg tgaaatccgt aaacggcctc ttatagaaac caatggtgaa    3840
acgggagaaa tcgtttggga taaaggtcgt gactttgcca ccgttcgtaa agtcctctca    3900
atgccgcaag ttaacattgt caagaagacg gaagttcaaa caggggatt ctccaaagaa     3960 tctatcctgc cgaagcgtaa cagtgataaa cttattgcca gaaaaaaaga ttgggatcca    4020
aaaaaatacg gaggctttga ttcccctacc gtcgcgtata gtgtgctggt ggttgctaaa    4080
gtcgagaaag ggaaaagcaa gaaattgaaa tcagttaaag aactgctggg tattacaatt    4140
atggaaagat cgtccttga gaaaaatccg atcgactttt tagaggccaa ggggtataag     4200
gaagtgaaaa aagatctcat catcaaatta ccgaagtata gtcttttga gctgaaaaac     4260 ggcagaaaaa gaatgctggc ctccgcgggc gagttacaga agggaaatga gctggcgctg    4320
ccttccaaat atgttaattt tctgtaccrt gccagtcatt atgagaaact gaagggcagc    4380
cccgaagata acgaacagaa acaattattc gtggaacagc ataagcacta tttagatgaa    4440
attatagagc aaaattagtga attttctaag cgcgttatcc tcgcggatgc taatttagac    4500
aaagtactgt cagcttataa taaacatcgg gataagccga ttagagaaca ggccgaaaat    4560
atcattcatt tgtttacctt aaccaaccct ggagcaccag ctgccttcaa atatttcgat    4620
accacaattg atcgtaaacg gtatacaagt acaaaagaag tcttggacgc aaccctcatt    4680
catcaatcta ttactggatt atatgagaca cgcattgatc tttcacagct gggcggagac    4740
aagaagaaaa aactgaaact gcaccatcat caccatcatc atcaccatca ttgataactc    4800
gagaaagctt acataaaaaa ccggccttgg ccccgccggt tttttattat ttttcttcct    4860
ccgcatgttc aatccgctcc ataatcgacg gatggctccc tctgaaaatt ttaacgagaa    4920
acggcgggtt gacccggctc agtcccgtaa cggccaagtc ctgaaacgtc tcaatcgccg    4980
cttcccggtt tccggtcagc tcaatgccgt aacggtcggc ggcgttttcc tgataccggg    5040
agacggcatt cgtaatcgaa ttcgcggccg cacgcgtcat ggtcgctgat aaacagctga    5100
catcaactaa aagcttcatt aaatactttg aaaaagttg ttgacttaaa agaagctaaa     5160
tgttatagta ataaaagcag gtgccaggca tcaaataaaa cgaaaggctc agtcgaaaga    5220
ctgggccttt cgttttatct gttgtttgtc ggtgaacgct ctctactaga gtcacactgg    5280
```

```
ctcaccttcg ggtgggcctt tctgcgttta taatggcggg atcgttgtat atttcttgac    5340 acctttcgg catcgcccta aattcggcgt cctcatattg tgtgaggacg ttttattacg     5400
tgtttacgaa gcaaaagcta aaaccaggag ctatttaatg gcaacagtta accagctggt    5460
acgcaaacca cgtgctcgca aagttgcgaa aagcaacgtg cctgcgctgg aagcatgccc    5520
gcaaaaacgt ggcgtatgta ctcgtgtata tactaccact cctaaaaaac cgaactccgc    5580
gctgcgtaaa gtatgccgtg ttcgtctgac taacggtttc gaagtgactt cctacatcgg    5640
tggtgaaggt cacaacctgc aggagcactc cgtgatcctg atccgtggcg gtcgtgttaa    5700
agacctcccg ggtgttcgtt accacaccgt acgtggtgcg cttgactgct ccggcgttaa    5760
agaccgtaag caggctcgtt ccaagtatgg cgtgaagcgt cctaaggctt aggttaataa    5820
caggcctgct ggtaatcgca ggcctttta ttttacacc tgcgttttag agctagaaat     5880
agcaagttaa aataaggcta gtccgttatc aacttgaaaa agtggcaccg agtcggtgcg    5940
actcctgttg atagatccag taatgacctc agaactccat ctggatttgt tcagaacgct    6000
cggttgccgc cggcgttttt ttattggtga gaatgtcgac ctcgagagtt acgctaggga    6060
taacagggta atataggagc tccagtcggc ttaaaccagt tttcgctggt gcgaaaaaag    6120
agtgtcttgt gacacctaaa ttcaaaatct atcggtcaga tttataccga tttgattta    6180 tatattcttg aataacatac gccgagttat cacataaaag cgggaaccaa tcataaaatt    6240
taaacttcat tgcataatcc attaaactct taaattctac gattccttgt tcatcaataa    6300
actcaatcat ttctttaatt aatttatatc tatctgttgt tgttttcttt aataattcat    6360
taacatctac accgccataa actatcatat cttcttttg atatttaaat ttattaggat    6420
cgtccatgtg aagcatatat ctcacaagac ctttcacact tcctgcaatc tgcggaatag    6480
tcgcattcaa ttcttctgtt aattattttt atctgttcat aagatttatt accctcatac    6540
atcactagaa tatgataatg ctctttttc atcctacctt ctgtatcagt atccctatca    6600
tgtaatggag acactacaaa ttgaatgtgt aactcttta aatactctaa ccactcggct    6660
tttgctgatt ctggatataa aacaaatgtc caattacgtc ctcttgaatt tttcttgttt    6720
tcagtttctt ttattacatt ttcgctcatg atataataac ggtgctaata cacttaacaa    6780
aatttagtca tagataggca gcatgccagt gctgtctatc ttttttttgtt taaaatgcac    6840 cgtattcctc ctttgcatat tttttatta gaataccggt tgcatctgat ttgctaatat    6900 tatattttc tttgattcta tttaatatct catttcttc tgttgtaagt cttaaagtaa     6960
cagcaacttt tttctcttct tttctatcta caactatcac tgtacctccc aacatctgtt    7020
tttttcactt taacataaaa aacaaccttt taacattaaa aacccaatat ttatttattt    7080
gtttggacaa tggacactgg acacctaggg gggaggtcgt agtaccccc tatgttttct     7140 cccctaaata accccaaaaa tctaagaaaa aaagacctca aaaggtctt taattaacat     7200 ctcaaatttc gcatttattc caatttcctt tttgcgtgtg atgcgagctc atcggctccg    7260
tcgatactat gttatacgcc aactttcaaa acaactttga aaaagctgtt ttctggtatt    7320
taaggtttta gaatgcaagg aacagtgaat tggagttcgt cttgttataa ttagcttctt    7380
ggggtatctt taaatactgt agaaaagagg aaggaaataa taaatggcta aaatgagaat    7440
atcaccggaa ttgaaaaaac tgatcgaaaa ataccgctgc gtaaaagata cggaaggaat    7500
gtctcctgct aaggtatata agctggtggg agaaaatgaa aacctatatt taaaaatgac    7560
ggacagccgg tataaaggga ccacctatga tgtggaacgg gaaaaggaca tgatgctatg    7620
```

```
gctggaagga aagctgcctg ttccaaaggt cctgcacttt gaacggcatg atggctggag    7680
caatctgctc atgagtgagg ccgatggcgt cctttgctcg gaagagtatg aagatgaaca    7740 aagcccctgaa aagattatcg agctgtatgc ggagtgcatc aggctctttc actccatcga   7800
catatcggat tgtccctata cgaatagctt agacagccgc ttagccgaat tggattactt    7860
actgaataac gatctggccg atgtggattg cgaaaactgg gaagaagaca ctccatttaa    7920
agatccgcgc gagctgtatg attttttaaa gacggaaaag cccgaagagg aacttgtctt    7980
ttcccacggc gacctgggag acagcaacat ctttgtgaaa gatggcaaag taagtggctt    8040
tattgatctt gggagaagcg gcagggcgga caagtggtat gacattgcct tctgcgtccg    8100
gtcgatcagg gaggatatcg gggaagaaca gtatgtcgag ctattttttg acttactggg    8160
gatcaagcct gattgggaga aaataaaata ttatatttta ctggatgaat tgttttagtg    8220
actgcagtga gatctggtaa tgactctcta gcttgaggca tcaaataaaa cgaaaggctc    8280
agtcgaaaga ctgggccttt cgttttatct gttgtttgtc ggtgaacgct ctcctgagta    8340
ggacaaatcc gccgctctag ctaagcagaa ggccatcctg acgatggcc tttttgcgtt    8400 tctacaaact cttgttaact ctagagctgc ctgccgcgtt tcggtgatga agatcttccc    8460
gatgattaat taattcagaa cgctcggttg ccgccgggcg ttttttatga agcttcgttg    8520
ctggcgtttt tccataggct ccgcccccct gacgagcatc acaaaaatcg acgctcaagt    8580
cagaggtggc gaaacccgac aggactataa agataccagg cgtttccccc tggaagctcc    8640
ctcgtgcgct ctcctgttcc gaccctgccg cttaccggat acctgtccgc ctttctccct    8700
tcgggaagcg tggcgctttc tcatagctca cgctgtaggt atctcagttc ggtgtaggtc    8760
gttcgctcca agctgggctg tgtgcacgaa ccccccgttc agcccgaccg ctgcgcctta    8820
tccggtaact atcgtcttga gtccaacccg gtaagacacg acttatcgcc actggcagca    8880
gccactggta acaggattag cagagcgagg tatgtaggcg gtgctacaga gttcttgaag    8940
tggtggccta actacggcta cactagaagg acagtatttg gtatctgcgc tctgctgaag    9000
ccagttacct tcggaaaaag agttggtagc tcttgatccg gcaaacaaac caccgctggt    9060
agcggtggtt tttttgtttg caagcagcag attacgcgca gaaaaaaagg atctcaagaa    9120
gatcctttga tcttttctac ggggtctgac gctcagtgga acgaaaactc acgttaaggg    9180
attttggtca tgagattatc aaaaaggatc ttcacctaga tccttttaaa ttaaaaatga    9240
agttttaaat caatctaaag tatatatgag taaacttggt ctgaca                    9286
```

<210> SEQ ID NO 23
<211> LENGTH: 129
<212> TYPE: DNA
<213> ORGANISM: Artificial Sequence
<220> FEATURE:
<223> OTHER INFORMATION: synthetic

<400> SEQUENCE: 23

```
ccaggcatca aataaaacga aaggctcagt cgaaagactg gcctttcgt tttatctgtt     60 gtttgtcggt gaacgctctc tactagagtc acactggctc accttcgggt gggcctttct   120
gcgtttata                                                            129
```

<210> SEQ ID NO 24
<211> LENGTH: 544
<212> TYPE: DNA
<213> ORGANISM: Escherichia coli

<400> SEQUENCE: 24

-continued

```
atggcgggat cgttgtatat ttcttgacac cttttcggca tcgccctaaa ttcggcgtcc      60
tcatattgtg tgaggacgtt ttattacgtg tttacgaagc aaaagctaaa accaggagct     120
atttaatggc aacagttaac cagctggtac gcaaaccacg tgctcgcaaa gttgcgaaaa     180
gcaacgtgcc tgcgctggaa gcatgccgc aaaaacgtgg cgtatgtact cgtgtatata      240
ctaccactcc taaaaaaccg aactccgcgc tgcgtaaagt atgccgtgtt cgtctgacta     300
acggtttcga agtgacttcc tacatcggtg gtgaaggtca aacctgcag gagcactccg      360 tgatcctgat ccgtggcggt cgtgttaaag acctcccggg tgttcgttac cacaccgtac     420
gtggtgcgct tgactgctcc ggcgttaaag accgtaagca ggctcgttcc aagtatggcg     480
tgaagcgtcc taaggcttag gttaataaca ggcctgctgg taatcgcagg cctttttatt     540
ttta                                                                  544
```

<210> SEQ ID NO 25
<211> LENGTH: 76
<212> TYPE: DNA
<213> ORGANISM: Artificial Sequence
<220> FEATURE:
<223> OTHER INFORMATION: synthetic

<400> SEQUENCE: 25

```
gttttagagc tagaaatagc aagttaaaat aaggctagtc cgttatcaac ttgaaaaagt      60
ggcaccgagt cggtgc                                                      76
```

<210> SEQ ID NO 26
<211> LENGTH: 95
<212> TYPE: DNA
<213> ORGANISM: Artificial Sequence
<220> FEATURE:
<223> OTHER INFORMATION: lambda phage

<400> SEQUENCE: 26

```
gactcctgtt gatagatcca gtaatgacct cagaactcca tctggatttg ttcagaacgc      60
tcggttgccg ccgggcgttt tttattggtg agaat                                 95
```

<210> SEQ ID NO 27
<211> LENGTH: 1119
<212> TYPE: DNA
<213> ORGANISM: Bacillus subtilis

<400> SEQUENCE: 27

```
atgcgcaagt ggattgcggc agcaggactt gcttacgtgc tgtacgggct gttttttttat      60 tggtattttt tcctgtcggg tgattccgca ataccggaag ccgtgaaagg gacgcaggct     120
gatccggctt ctttcatgaa gccgtctgag ttggcagtgg ccgagcagta ttcgaatgtc     180 aagaatttt tatttttat cggggtacca cttgattggt ttctgttttt tgttctgctt       240
gtcagcggtg tttcaaagaa aatcaagaaa tggatcgaag cggccgtgcc ttttcggttt     300
ttgcagaccg ttggttttgt gtttgtgctt tcgctgatta acattggt gacgctgcct       360 ttagattgga taggctatca agtatcgctt gactataaca tttccacaca gacaacggcc     420
agctgggcta aggatcaggt tatcagcttt tggatcagct ttccaatctt tacgctttgc     480
gttctcgttt tttattggct gatcaaaagg catgaaaaaa aatggtggtt atacgcctgg     540
ctgttaacag tgccgttttc gctgtttctg tttttattc agccggtcat tatcgatcct      600
ttatacaatg attttttatcc gctgaaaaac aaagagcttg aaagcaaaat tttagagctg     660
```

```
gcagatgaag ccaatattcc ggctgaccat gtatatgaag tgaacatgtc agaaaaaaca    720
aatgcgctga atgcctatgt tacaggaatt ggggccaata aacggattgt attgtgggat    780
acgacgctga acaaacttga cgattcagaa attctgttta ttatgggcca cgaaatgggc    840
cattatgtca tgaagcacgt ttacatcggt ctggctggct atttgctcgt gtcgctcgcc    900 ggatttatg tcattgataa gctttacaag cggacggttc gcctaacccg cagcatgttt    960
catttagaag gcggcatga tcttgcggca cttccgctgt tattgctttt gttttctgtt    1020
ttgagctttg cggttacgcc ttttttctaat gctgtctcgc gttatcagga gaataaggct    1080
gaccagtatg ggatcgagtt aacgcaaaca acaagctga                           1119
```

```
<210> SEQ ID NO 28
<211> LENGTH: 23
<212> TYPE: DNA
<213> ORGANISM: Bacillus subtilis

<400> SEQUENCE: 28
tcaagctctt tgtttttcag cgg                                              23

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
tcaagctctt tgtttttcag                                                  20

<210> SEQ ID NO 30
<211> LENGTH: 3
<212> TYPE: DNA
<213> ORGANISM: Bacillus subtilis

<400> SEQUENCE: 30 cgg                                                                     3

<210> SEQ ID NO 31
<211> LENGTH: 96
<212> TYPE: RNA
<213> ORGANISM: Artificial Sequence
<220> FEATURE:
<223> OTHER INFORMATION: synthetic

<400> SEQUENCE: 31
ucaagcucuu uguuuuucag guuuuagagc uagaaauagc aaguuaaaau aaggcuaguc    60
cguuaucaac uugaaaaagu ggcaccgagu cggugc                              96

<210> SEQ ID NO 32
<211> LENGTH: 96
<212> TYPE: DNA
<213> ORGANISM: Artificial Sequence
<220> FEATURE:
<223> OTHER INFORMATION: synthetic

<400> SEQUENCE: 32
tcaagctctt tgtttttcag gttttagagc tagaaatagc aagttaaaat aaggctagtc    60
cgttatcaac ttgaaaaagt ggcaccgagt cggtgc                              96

<210> SEQ ID NO 33
<211> LENGTH: 189
```

```
<212> TYPE: DNA
<213> ORGANISM: Artificial Sequence
<220> FEATURE:
<223> OTHER INFORMATION: synthetic

<400> SEQUENCE: 33
tcgctgataa acagctgaca tcaactaaaa gcttcattaa atactttgaa aaagttgtt      60 gacttaaaag aagctaaatg ttatagtaat aaatcaagct ctttgttttt caggttttag    120
agctagaaat agcaagttaa ataaggcta gtccgttatc aacttgaaaa agtggcaccg     180
agtcggtgc                                                             189

<210> SEQ ID NO 34
<211> LENGTH: 8618
<212> TYPE: DNA
<213> ORGANISM: Artificial Sequence
<220> FEATURE:
<223> OTHER INFORMATION: synthetic

<400> SEQUENCE: 34
gaattcctcc attttcttct gctatcaaaa taacagactc gtgattttcc aaacgagctt     60
tcaaaaaagc ctctgcccct tgcaaatcgg atgcctgtct ataaattcc cgatattggt    120 taaacagcgg cgcaatggcg gccgcatctg atgtctttgc ttggcgaatg ttcatcttat    180
ttcttcctcc ctctcaataa ttttttcatt ctatcccttt tctgtaaagt ttattttca    240 gaatacttt atcatcatgc tttgaaaaaa tatcacgata atatccattg ttctcacgga     300
agcacacgca ggtcatttga acgaattttt tcgacaggaa tttgccggga ctcaggagca    360
tttaacctaa aaaagcatga catttcagca taatgaacat ttactcatgt ctattttcgt    420
tcttttctgt atgaaaatag ttatttcgag tctctacgga aatagcgaga gatgatatac    480
ctaaatagag ataaaatcat ctcaaaaaaa tgggtctact aaaatattat ccatctatt    540 acaataaatt cacagaatag tcttttaagt aagtctactc tgaattttt taaaaggaga     600 gggtaactag tggccccaaa aagaaacgc aaggttatgg ataaaaata cagcattggt     660 ctggatatcg gaaccaacag cgttgggtgg gcagtaataa cagatgaata caaagtgccg    720
tcaaaaaaat ttaaggttct ggggaataca gatcgccaca gcataaaaaa gaatctgatt    780
ggggcattgc tgtttgattc gggtgagaca gctgaggcca cgcgtctgaa acgtacagca    840
agaagacgtt acacacgtcg taaaaatcgt atttgctact tacaggaaat ttttttctaac   900 gaaatggcca aggtagatga tagtttcttc catcgtctcg aagaatcttt tctggttgag    960
gaagataaaa aacacgaacg tcaccctatc tttggcaata tcgtggatga agtggcctat   1020
catgaaaaat accctacgat ttatcatctt cgcaagaagt tggttgatag tacggacaaa   1080
gcggatctgc gtttaatcta tcttgcgtta gcgcacatga tcaaatttcg tggtcatttc   1140
ttaattgaag gtgatctgaa tcctgataac tctgatgtgg acaaattgtt tatacaatta   1200
gtgcaaacct ataatcagct gttcgaggaa accccatta atgcctctgg agttgatgcc    1260
aaagcgattt taagcgcgag actttctaag tcccggcgtc tggagaatct gatcgcccag   1320
ttaccagggg aaaagaaaaa tggtctgttt ggtaatctga ttgccctcag tctggggctt   1380
accccgaact caaatccaa ttttgacctg gctgaggacg caaagctgca gctgagcaaa    1440
gatacttatg atgatgacct cgacaatctg ctcgcccaga ttggtgacca atatgcggat   1500
ctgtttctgg cagcgaagaa tctttcggat gctatcttgc tgtcggatat tctgcgtgtt   1560
aataccgaaa tcaccaaagc gcctctgtct gcaagtatga tcaagagata cgacgagcac   1620
```

```
caccaggacc tgactcttct taaggcactg gtacgccaac agcttccgga gaaatacaaa    1680
gaaatattct tcgaccagtc caagaatggt tacgcgggct acatcgatgg tggtgcatca    1740
caggaagagt tctataaatt tattaaacca atccttgaga aaatggatgg cacggaagag    1800
ttacttgtta aacttaaccg cgaagacttg cttagaaagc aacgtacatt cgacaacggc    1860
tccatcccac accagattca tttaggtgaa cttcacgcca tcttgcgcag acaagaagat    1920
ttctatccct tcttaaaaga caatcgggag aaaatcgaga agatcctgac gttccgcatt    1980
ccctattatg tcggtcccct ggcacgtggt aattctcggt ttgcctggat gacgcgcaaa    2040
agtgaggaaa ccatcacccc ttggaacttt gaagaagtcg tggataaagg tgctagcgcg    2100
cagtctttta tagaaagaat gacgaacttc gataaaaact tgcccaacga aaagtcctg     2160 cccaagcact ctcttttata tgagtacttt actgtgtaca acgaactgac taaagtgaaa    2220
tacgttacgg aaggtatgcg caaacctgcc tttcttagtg gcgagcagaa aaaagcaatt    2280
gtcgatcttc tctttaaaac gatcgcaag gtaactgtaa aacagctgaa ggaagattat     2340
ttcaaaaaga tcgaatgctt tgattctgtc gagatctcgg gtgtcgaaga tcgtttcaac    2400
gcttccttag ggacctatca tgatttgctg aagataataa aagacaaaga ctttctcgac    2460
aatgaagaaa atgaagatat tctggaggat attgttttga ccttgacctt attcgaagat    2520
agagagatga tcgaggagcg cttaaaaacc tatgcccacc tgtttgatga caaagtcatg    2580
aagcaattaa agcgccgcag atatacgggg tggggccgct tgagccgcaa gttgattaac    2640
ggtattagag acaagcagag cggaaaaact atcctggatt tcctcaaatc tgacggattt    2700
gcgaaccgca attttatgca gcttatacat gatgattcgc ttacattcaa agaggatatt    2760
cagaaggctc aggtgtctgg gcaaggtgat tcactccacg aacatatagc aaatttggcc    2820
ggctctcctg cgattaagaa ggggatcctg caaacagtta agttgtgga tgaacttgta     2880 aaagtaatgg gccgccacaa gccggagaat atcgtgatag aaatggcgcg cgagaatcaa    2940
acgacacaaa aaggtcaaaa gaactcaaga gagagaatga gcgcattga ggaggggata     3000 aaggaacttg gatctcaaat tctgaaagaa catccagttg aaaacactca gctgcaaaat    3060
gaaaaattgt acctgtacta cctgcagaat ggaagagaca tgtacgtgga tcaggaattg    3120
gatatcaata gactctcgga ctatgacgta gatcacattg tccctcagag cttcctcaag    3180
gatgattcta tagataataa agtacttacg agatcggaca aaaatcgcgg taaatcggat    3240
aacgtcccat cggaggaagt cgttaaaaag atgaaaaact attggcgtca actgctgaac    3300
gccaagctga tcacacagcg taagtttgat aatctgacta aagccgaacg cggtggtctt    3360
agtgaactcg ataaagcagg atttataaaa cggcagttag tagaaacgcg ccaaattacg    3420
aaacacgtgg ctcagatcct cgattctaga atgaatacaa agtacgatga aaacgataaa    3480
ctgatccgtg aagtaaaagt cattaccctta aaatctaaac ttgtgtccga tttccgcaaa    3540
gattttcagt tttacaaggt ccgggaaatc aataactatc accatgcaca tgatgcatat    3600
ttaaatgcgg ttgtaggcac ggcccttatt aagaaatacc ctaaactcga aagtgagttt    3660
gtttatgggg attataaagt gtatgacgtt cgcaaaatga tcgcgaaatc agaacaggaa    3720
atcggtaagg ctaccgctaa atactttttt tattccaaca ttatgaattt ttttaagacc    3780
gaaataactc tcgcgaatgg tgaaatccgt aaacggcctc ttatagaaac caatggtgaa    3840
acggagaaaa tcgtttggga taaaggtcgt gactttgcca ccgttcgtaa agtcctctca    3900
atgccgcaag ttaacattgt caagaagacg gaagttcaaa caggggggatt ctccaaagaa   3960 tctatcctgc cgaagcgtaa cagtgataaa cttattgcca gaaaaaaaga ttgggatcca   4020
```

```
aaaaaatacg gaggctttga ttccctacc gtcgcgtata gtgtgctggt ggttgctaaa    4080
gtcgagaaag ggaaaagcaa gaaattgaaa tcagttaaag aactgctggg tattacaatt    4140
atggaaagat cgtcctttga gaaaaatccg atcgactttt tagaggccaa ggggtataag    4200
gaagtgaaaa aagatctcat catcaaatta ccgaagtata gtcttttga gctggaaaac    4260 ggcagaaaaa gaatgctggc ctccgcgggc gagttacaga agggaaatga gctggcgctg    4320
ccttccaaat atgttaattt tctgtacctt gccagtcatt atgagaaact gaagggcagc    4380
cccgaagata acgaacagaa acaattattc gtggaacagc ataagcacta tttagatgaa    4440
attatagagc aaattagtga attttctaag cgcgttatcc tcgcggatgc taatttagac    4500
aaagtactgt cagcttataa taaacatcgg gataagccga ttagagaaca ggccgaaaat    4560
atcattcatt tgtttaccttt aaccaacctt ggagcaccag ctgccttcaa atatttcgat    4620
accacaattg atcgtaaacg gtatacaagt acaaagaag tcttggacgc aaccctcatt    4680
catcaatcta ttactggatt atatgagaca cgcattgatc tttcacagct gggcggagac    4740
aagaagaaaa aactgaaact gcaccatcat caccatcatc atcaccatca ttgataactc    4800
gagaaagctt acataaaaaa ccggccttgg ccccgccggt tttttattat ttttcttcct    4860
ccgcatgttc aatccgctcc ataatcgacg gatggctccc tctgaaaatt taacgagaa    4920 acggcgggtt gaccggctc agtccgtaa cggccaagtc ctgaaacgtc tcaatcgccg    4980
cttcccggtt tccggtcagc tcaatgccgt aacggtcggc ggcgttttcc tgataccggg    5040
agacggcatt cgtaatcgaa ttcgcggccg cacgcgtcat ggtcgctgat aaacagctga    5100
catcaactaa aagcttcatt aaatactttg aaaaagttg ttgacttaaa agaagctaaa    5160
tgttatagta ataatcaag ctctttgttt ttcaggtttt agagctagaa atagcaagtt    5220
aaaataaggc tagtccgtta tcaacttgaa aaagtggcac cgagtcggtg cgactcctgt    5280
tgatagatcc agtaatgacc tcagaactcc atctggattt gttcagaacg ctcggttgcc    5340
gccgggcgtt ttttattggt gagaatgtcg acctcgagag ttacgctagg gataacaggg    5400 taatataga gctccagtcg gcttaaacca gttttcgctg gtgcgaaaaa agagtgtctt    5460
gtgacaccta aattcaaaat ctatcggtca gatttatacc gatttgattt tatatattct    5520
tgaataacat acgccgagtt atcacataaa agcgggaacc aatcataaaa tttaaacttc    5580
attgcataat ccattaaact cttaaattct acgattcctt gttcatcaat aaactcaatc    5640
atttctttaa ttaatttata tctatctgtt gttgttttct ttaataattc attaacatct    5700
acaccgccat aaactatcat atcttctttt tgatatttaa atttattagg atcgtccatg    5760
tgaagcatat atctcacaag acctttcaca cttcctgcaa tctgcggaat agtcgcattc    5820
aattcttctg ttaattattt ttatctgttc ataagattta ttaccctcat acatcactag    5880
aatatgataa tgctcttttt tcatcctacc ttctgtatca gtatccctat catgtaatgg    5940
agacactaca aattgaatgt gtaactcttt taaatactct aaccactcgg cttttgctga    6000
ttctggatat aaaacaaatg tccaattacg tcctcttgaa ttttcttgt tttcagtttc    6060 ttttattaca ttttcgctca tgatataata acggtgctaa tacacttaac aaaatttagt    6120
catagatagg cagcatgcca gtgctgtcta tctttttttg tttaaaatgc accgtattcc    6180
tcctttgcat atttttttat tagaataccg gttgcatctg atttgctaat attatatttt    6240
tctttgattc tatttaatat ctcattttct tctgttgtaa gtcttaaagt aacagcaact    6300
tttttctctt cttttctatc tacaactatc actgtacctc ccaacatctg ttttttcac    6360
```

-continued

```
tttaacataa aaaacaacct tttaacatta aaaacccaat atttatttat ttgtttggac    6420
aatggacact ggacacctag gggggaggtc gtagtacccc cctatgtttt ctcccctaaa    6480
taaccccaaa aatctaagaa aaaaagacct caaaaggtc tttaattaac atctcaaatt    6540
tcgcatttat tccaatttcc ttttttgcgtg tgatgcgagc tcatcggctc cgtcgatact   6600
atgttatacg ccaactttca aaacaacttt gaaaaagctg ttttctggta tttaaggttt    6660
tagaatgcaa ggaacagtga attggagttc gtcttgttat aattagcttc ttggggtatc    6720
tttaaatact gtagaaaaga ggaaggaaat aataaatggc taaaatgaga atatcaccgg    6780
aattgaaaaa actgatcgaa aaataccgct gcgtaaaaga tacggaagga atgtctcctg    6840
ctaaggtata taagctggtg ggagaaaatg aaaacctata tttaaaaatg acggacagcc    6900
ggtataaagg gaccacctat gatgtggaac gggaaaagga catgatgcta tggctggaag    6960
gaaagctgcc tgttccaaag gtcctgcact ttgaacggca tgatggctgg agcaatctgc    7020
tcatgagtga ggccgatggc gtcctttgct cggaagagta tgaagatgaa caaagccctg    7080
aaaagattat cgagctgtat gcggagtgca tcaggctctt tcactccatc gacatatcgg    7140
attgtcccta tacgaatagc ttagacagcc gcttagccga attggattac ttactgaata    7200
acgatctggc cgatgtggat tgcgaaaact gggaagaaga cactccattt aaagatccgc    7260
gcgagctgta tgatttttta aagacgaaaa agcccgaaga ggaacttgtc ttttcccacg    7320
gcgacctggg agacagcaac atctttgtga agatggcaa agtaagtggc tttattgatc    7380
ttgggagaag cggcagggcg acaagtggt atgacattgc cttctgcgtc cggtcgatca    7440
gggaggatat cggggaagaa cagtatgtcg agctatttt tgacttactg gggatcaagc    7500
ctgattggga gaaaataaaa tattatattt tactggatga attgttttag tgactgcagt    7560
gagatctggt aatgactctc tagcttgagg catcaaataa aacgaaaggc tcagtcgaaa    7620
gactgggcct ttcgttttat ctgttgtttg tcggtgaacg ctctcctgag taggacaaat    7680
ccgccgctct agctaagcag aaggccatcc tgacggatgg ccttttttgcg tttctacaaa    7740
ctcttgttaa ctctagagct gcctgccgcg tttcggtgat gaagatcttc ccgatgatta    7800
attaattcag aacgctcggt tgccgccggg cgttttttat gaagcttcgt tgctggcgtt    7860
tttccatagg ctccgccccc ctgacgagca tcacaaaaat cgacgctcaa gtcagaggtg    7920
gcgaaacccg acaggactat aaagatacca ggcgtttccc cctggaagct ccctcgtgcg    7980
ctctcctgtt ccgaccctgc cgcttaccgg atacctgtcc gcctttctcc cttcgggaag    8040
cgtggcgctt tctcatagct cacgctgtag gtatctcagt tcggtgtagg tcgttcgctc    8100
caagctgggc tgtgtgcacg aaccccccgt tcagcccgac cgctgcgcct tatccggtaa    8160
ctatcgtctt gagtccaacc cggtaagaca cgacttatcg ccactggcag cagccactgg    8220
taacaggatt agcagagcga ggtatgtagg cggtgctaca gagttcttga agtggtggcc    8280
taactacggc tacactagaa ggacagtatt tggtatctgc gctctgctga agccagttac    8340
cttcggaaaa agagttggta gctcttgatc cggcaaacaa accaccgctg gtagcggtgg    8400
tttttttgtt tgcaagcagc agattacgcg cagaaaaaaa ggatctcaag aagatccttt    8460
gatcttttct acgggtctg acgctcagtg gaacgaaaac tcacgttaag ggattttggt    8520
catgagatta tcaaaaagga tcttcaccta gatccttta aattaaaaat gaagttttaa    8580
atcaatctaa agtatatatg agtaaacttg gtctgaca                          8618
```

<210> SEQ ID NO 35
<211> LENGTH: 7423

```
<212> TYPE: DNA
<213> ORGANISM: Bacillus subtilis

<400> SEQUENCE: 35
```

| | | | | | |
|---|---|---|---|---|---|
| cattactttg | ggaacattac | gaaagaggat | ttccttgatc | tgatttacta | aggcaaaaca | 60 |
| catcgtttga | aagagcggtt | gtgtttttga | aataatggag | gcaggaggga | ttcacatgaa | 120 |
| agtgttttta | atcggagcga | acggacaaat | cgggcaaaga | ctcgtctctt | tattccaaga | 180 |
| taatcctgat | cattccatca | gagcgatggt | cagaaaagaa | gaacagaaag | cgtctcttga | 240 |
| agctgccggt | gcagaagctg | tgcttgcgaa | tctggagggc | agcccggaag | aaatcgccgc | 300 |
| tgcggcaaaa | ggttgtgacg | cgatcatttt | cacagccggt | tccggcggca | gcacaggcta | 360 |
| tgataaaacg | ctgctggtgg | atcttgatgg | agcggcaaaa | gccattgaag | ctgcggccat | 420 |
| tgccggaatc | aaacggttta | ttatggtcag | cgccctgcaa | gcccataacc | gtgaaaattg | 480 |
| gaatgaggca | ctcaagcctt | attatgtggc | caagcattat | gctgataaaa | ttctggaagc | 540 |
| gagcggttta | acctatacga | ttatccgtcc | gggaggcctt | cgcaatgagc | ctggaacggg | 600 |
| aactgtttca | gcagcgaagg | atctggagcg | gggatttatt | tcccgtgatg | acgttgcaaa | 660 |
| aacggtcatt | gcctctttag | atgagaagaa | tacggaaaat | cgggcctttg | atctgacaga | 720 |
| aggagatacg | ccgattgccg | aagcattgaa | gaaactatga | cagtactgac | actcagggct | 780 |
| ttttgctctt | gagtgttttt | ttctgtttct | ctataatgga | gaagaaagct | tggcttcaat | 840 |
| aatgaatgac | tattcattca | cttaaggggt | gggagaatga | atcttgtttc | aaaattggaa | 900 |
| gaaacagcat | ctgagaagcc | cgacagcatc | gcatgcaggt | ttaaagatca | catgatgacg | 960 |
| tatcaagagc | tgaatgaata | tattcagcga | tttgcggacg | gccttcagga | agccggtatg | 1020 |
| gagaaagggg | accatttagc | tttgctgctt | ggcaattcgc | ctgattttat | catcgcgttt | 1080 |
| tttggcgctt | taaaagctgg | gatcgtagtt | gttcccatca | atccgttgta | cacgccgaca | 1140 |
| gaaattggtt | atatgctgac | aaatggcgat | gtaaaggcaa | tcgtgggcgt | tagccagctt | 1200 |
| ttgccgcttt | atgagagcat | gcatgaatcg | ctgccaaagg | ttgagctcgt | cattttatgc | 1260 |
| cagacggggg | aggccgagcc | ggaagctgcg | gacccagagg | tcaggatgaa | aatgacaacg | 1320 |
| tttgcaaaaa | tattgcggcc | gacatctgcc | gctaaacaaa | accaagaacc | tgtacctgat | 1380 |
| gataccgcgg | ttattttata | tacgtcagga | acgactggaa | aaccgaaagg | cgcgatgctg | 1440 |
| acacatcaga | atttgtacag | caatgccaac | gatgtcgcag | gctatttggg | aatggatgag | 1500 |
| agggacaatg | tggtctgcgc | tcttcccatg | tttcacgtgt | tttgtttaac | cgtctgtatg | 1560 |
| aatgcaccgc | tgatgagcgg | cgcaactgta | ttgattgagc | tcaattcag | tccggcatct | 1620 |
| gttttttaagc | ttgttaagca | gcagcaggcg | accattttttg | ccggtgtgcc | tacaatgtat | 1680 |
| aactacttgt | ttcagcatga | aaacggaaag | aaagatgatt | tttcttcgat | ccggctgtgc | 1740 |
| atttcgggag | gcgcgtccat | gccagtcgcg | ttgctgacgg | cgtttgaaga | aaaattcggt | 1800 |
| gttaccattt | tggaaggcta | cgggctctcg | gaagcatcac | ccgtcacgtg | ctttaacccg | 1860 |
| tttgacaggg | gcagaaagcc | gggctccatc | gggacaagta | tcttacatgt | cgaaaacaag | 1920 |
| gtcgtagatc | cgctcggacg | cgagctgccc | gctcaccagg | tcggcgaatt | gatcgtgaaa | 1980 |
| ggccccaatg | tgatgaaggg | ctattataaa | atgccgatgg | aaacagagca | tgcattaaaa | 2040 |
| gacgggtggc | tttatacggg | ggacttggca | agacgggatg | aggacggcta | tttttacatt | 2100 |
| gttgaccgga | aaaagacat | gatcattgta | ggaggataca | atgtgtatcc | gcgggaggtg | 2160 |
| gaggaggtgc | tgtacagcca | tccggacgtc | aaggaggcgg | ttgtcatcgg | cgtgccggac | 2220 |

```
ccccaaagcg gggaagcggt aaagggatat gtggtgccga aacgctctgg ggtaacagag    2280
gaggacatca tgcagcactg cgaaaagcat ctggcaaaat acaagcggcc tgccgccatt    2340
acgtttcttg acgatattcc gaaaaatgcg acggggaaaa tgctcagacg ggcactgaga    2400
gatattttgc cccaataaaa tgaaaaagcg aagcggttag cttcgctttt tcattttcaa    2460
tcctttgctt cttttttaat aatatttagc agcgcctttg tatcattttt gcttaatttg    2520
tagtatgtgc catccttcaa aaaacggct tgctggctgc cgtcaatcca tagtctgaat     2580
gagtcatacc ggtctttatg aaacttgatt gtcccttcgt aatcaggggc tgatgttttt    2640
tctgtcttca cctgttttcc ctgattcata atatccagca tatctttgac gtgctgtctt    2700
ttttcaatct cgatatcttc ctggccgctt gaagacagtg tgatcaaatc cgcgtctacc    2760
gattgataca catcgcctga tcggctgtaa agataaaaaa atgcgataaa cacaagaccg    2820
attaccacga tggctgccac tatttttttc atttgcatca ctccaaacat tgttagtttt    2880
cccagcgatc ggggtttcca tgcttaaaag ggtggaaaag tgcggaacac agcttggttc    2940
taagaatttg aatttatgat tacaatagaa gtaacgggtt gatgtgagga gtgaggcgtt    3000
atgcgcaagt ggattgcggc agcaggactt gcttacgtgc tgtacgggct gttttttat    3060 tggtattttt tcctgtcggg tgattccgca ataccgaaag ccgtgaaagg gacgcaggct    3120
gatccggctt ctttcatgaa gccgtctgag ttggcagtgg ccgagcagta ttcgaatgtc    3180
aagaattttt tatttttat cggggtacca cttgattggt ttctgttttt tgttctgctt    3240
gtcagcggtg tttcaaagaa atcaagaaa tggatcgaag cggccgtgcc ttttcggttt     3300
ttgcagaccg ttggttttgt gtttgtgctt tcgctgatta caacattggt gacgctgcct    3360
ttagattgga taggctatca agtatcgctt gactataaca tttccacaca gacaacggcc    3420
agctgggcta aggatcaggt tatcagcttt tggatcagct ttccaatctt tacgctttgc    3480
gttctcgttt tttattggct gatcaaaagg catgaaaaaa aatggtggtt atacgcctgg    3540
ctgttaacag tgccgttttc gctgtttctg ttttttattc agccggtcat tatcgatcct    3600
ttatacaatg attttatcc gctgaaaaac aaagagcttg aaagcaaaat tttagagctg    3660
gcagatgaag ccaatattcc ggctgaccat gtatatgaag tgaacatgtc agaaaaaaca    3720
aatgcgctga atgcctatgt tacaggaatt ggggccaata acggattgt attgtgggat    3780 acgacgctga acaaacttga cgattcagaa attctgtta ttatgggcca cgaaatgggc     3840
cattatgtca tgaagcacgt ttacatcggt ctggctggct atttgctcgt gtcgctcgcc    3900 ggatttatg tcattgataa gctttacaag cggacggttc gcctaacccg cagcatgttt      3960
catttagaag ggcggcatga tcttgcggca cttccgctgt tattgctttt gttttctgtt    4020
ttgagctttg cggttacgcc ttttctaat gctgtctcgc gttatcagga gaataaggct     4080
gaccagtatg ggatcgagtt aacgcaaaca acaagctgat ccacaatttt ttgcttctca    4140
ctctttaccc tctccttta aaaaaattca gagtagactt acttaaaaga ctattctgtg     4200
aatttattgt aatagatgga ataatatttt agtagaccca ttttttttgag atgattttat    4260 ctctatttag gtatatcatc tctcgctatt tccgtagaga ctcgaaataa ctattttcat    4320
acagaaaaga acgaaaatag acatgagtaa atgttcatta tgctgaaatg tcatgctttt    4380
ttaggttaaa tgctcctgag tcccggcaaa ttcctgtcga aaaaattcgt tcaaatgacc    4440
tgcgtgtgct tccgtgagaa caatggatat tatcgtgata ttttttcaaa gcatgatgat    4500 aaagtattc tgaaaaataa actttacaga aaagggatag aatgaaaaaa ttattgagag     4560
ggaggaagaa ataagatgaa cattcgccaa gcaaagacat cagatgcggc cgccattgcg    4620
```

```
ccgctgttta accaatatcg ggaattttat agacaggcat ccgatttgca aggggcagag    4680
gcttttttga aagctcgttt ggaaaatcac gagtctgtta ttttgatagc agaagaaaat    4740
ggagaattca taggctttac ccagctctat ccaacgtttt cttctgtgtc aatgaaaagg    4800
atatacatat taaatgactt atttgtcgtt cctcatgcgc gtacaaaggg agccggcggc    4860
cggctgcttt ctgccgcaaa ggattatgca gggcaaaacg gggcaaaatg tttaacactt    4920
cagactgagc accacaaccg gaaggcaaga agcttgtatg agcaaaacgg ctatgaagag    4980
gataccggat ttgtccatta ttgtctcaat gtgccggcga agtgaaaatg gcggcttgat    5040
gatttggttt tttgaacgtt cttcggttac gatataaatg aaaaggagtg tgccgaatgt    5100
caacgttatt tcaagccttg caggcagaaa aaaatgccga tgatgtttca gtccatgtga    5160
aaaccatatc aacagaggat ttgccgaagg atggtgtcct gattaaagtt gcttattccg    5220
gcattaatta caaagatggt ctggccggaa aagcaggagg caatatcgtc agagagtatc    5280
cgcttatttt aggcattgat gctgcgggta cggtcgtctc ttccaatgat ccgcgttttg    5340
cggaggggga tgaggtgatc gcgacaagct atgagctcgg tgtctcacgt gatggcggat    5400
taagtgaata cgcttcggtg cctggtgact ggctggtgcc tttgccacag aatctttcgt    5460
taaaagaagc gatggtgtac ggaacggcgg gatttactgc ggcgttatca gtgcatcggc    5520
ttgaacagaa cggtctgtct ccggaaaaag gcagcgtgct agtcacagga gcaaccggcg    5580
gtgtcggcgg aattgcggta tcgatgctga acaagcgggg ttatgatgtg gtggcaagta    5640
ccggaaaccg ggaggcggct gattatttga acagcttgg tgcaagcgaa gtaatcagca    5700
gggaagatgt ctatgacgga acgcttaagg cgctgtccaa gcagcaatgg cagggagcgg    5760
ttgatccagt cggcggaaaa cagcttgcct cgcttttaag caaaattcaa tacgcggat    5820
ctgtcgcagt gagcggctta accggcggag gagaagttcc ggcaaccgtg tatcctttta    5880
ttcttcgcgg agtaagcctg ctcggaatcg attcagtata ttgtccgatg gacgtcagag    5940
ccgctgtttg ggagcgcatg tcttctgatc tcaagcctga tcagctgctg accatcgtgg    6000
acagggaagt atcattggaa gaaacgccgg gtgcgttaaa agatattttg caaaatcgca    6060
ttcaaggaag agtgattgtg aagctttaac aggatcagct tgcagagaat gttatttttc    6120
tgcaagcttt tttgtggaca ggatgatcag ctgctgaact gctgtgtcgc gaaacaagat    6180
tttcctgtaa gccgaacttt ctcttctcat tttaaaaata attggtgata atgattctca    6240
ttccgtgtta tactactctt ggacatctta accatagaaa ctaccaacag gagagactgg    6300
aacatatgaa aaaacactg attattctta cagttttact tctttctgtc ttaacggctg    6360
cttgctcgtc ttcaagcggc aatcaaaaca gtaaagaaca taaagtggcg gtaacacatg    6420
atttagggaa gacaaatgtg cctgagcatc cgaagcgggt tgttgttctt gagctaggtt    6480
ttattgatac actgcttgat ctcggcatta cgcctgtcgg ggttgccgat gacaacaaag    6540
cgaagcagct gatcaacaag gatgtgctga agaaaattga cggctacaca tctgtcggca    6600
ctcgctcaca gccaagcatg gaaaaaatcg cttcattaaa acccgattta attattgctg    6660
acacgacccg gcataagaag gtgtacgatc agctgaaaaa aatagcgccg acgattgcac    6720
ttaataattt aaatgctgat tatcaggata caattgacgc ttcgcttacg attgcaaaag    6780
cagtcggcaa ggagaaggaa atggagaaaa agctgacggc gcatgaagaa aagcttagcg    6840
agacaaagca gaaaatcagc gcgaacagcc agtccgtgct tttgatcgga aatacaaatg    6900
ataccattat ggccagggat gaaaacttct ttacatcgag acttttaaca caggtcggct    6960
```

```
accgatatgc aatcagtacg tcaggcaata gcgattcaag caatggcggc gactctgtga    7020
atatgaaaat gacactggag cagctgctga aaacagatcc ggatgtgatc atcctgatga    7080
caggaaaaac agatgacctc gacgccgacg gtaaacgccc gatcgaaaag aatgtccttt    7140
ggaaaaaact gaaggcagtg aaaaacgggc atgtatacca cgtggatcgt gcggtgtggt    7200
ctctgcgccg cagtgtagac ggggcgaatg ccatttttgga cgagcttcaa aaagagatgc    7260
cggctgctaa gaaataaaag aaaagacagg caaacgcctg tcttttttctt atttgataaa    7320 gccggataag tggctgttga tattatagtc ttttatccgc cattttttctt ctgcaaattc    7380 aatgttgctg aggcaggcgt tgacgagacg ggtgctttga agc                      7423
```

<210> SEQ ID NO 36
<211> LENGTH: 45
<212> TYPE: DNA
<213> ORGANISM: Artificial Sequence
<220> FEATURE:
<223> OTHER INFORMATION: synthetic

<400> SEQUENCE: 36

```
ttcaggattt ggccgtgacg gttttagagc tagaaatagc aagtt                    45
```

<210> SEQ ID NO 37
<211> LENGTH: 50
<212> TYPE: DNA
<213> ORGANISM: Artificial Sequence
<220> FEATURE:
<223> OTHER INFORMATION: synthetic

<400> SEQUENCE: 37

```
cgtcacggcc aaatcctgaa tttattacta taacatttag cttcttttaa               50
```

<210> SEQ ID NO 38
<211> LENGTH: 2982
<212> TYPE: DNA
<213> ORGANISM: Bacillus subtilis

<400> SEQUENCE: 38

```
gcttcaaagc acccgtctcg tcaacgcctg cctcagcaac attgaatttg cagaagaaaa     60
atggcggata aagactata atatcaacag ccacttatcc ggctttatca ataagaaaa     120 agacaggcgt ttgcctgtct tttcttttat ttcttagcag ccggcatctc ttttttgaagc    180 tcgtccaaaa tggcattcgc cccgtctaca ctgcggcgca gagaccacac cgcacgatcc    240
acgtggtata catgcccgtt tttcactgcc ttcagttttt tccaaaggac attcttttcg    300
atcgggcgtt taccgtcggc gtcgaggtca tctgttttttc ctgtcatcag gatgatcaca    360
tccggatctg ttttcagcag ctgctccagt gtcattttca tattcacaga gtcgccgcca    420
ttgcttgaat cgctattgcc tgacgtactg attgcatatc ggtagccgac ctgtgttaaa    480
agtctcgatg taaagaagtt ttcatccctg gccataatgg tatcatttgt atttccgatc    540
aaaagcacgg actggctgtt cgcgctgatt ttctgctttg tctcgctaag cttttcttca    600
tgcgccgtca gcttttctctc catttccttc tccttgccga ctgcttttgc aatcgtaagc    660
gaagcgtcaa ttgtatcctg ataatcagca tttaaattat taagtgcaat cgtcggcgct    720 attttttttca gctgatcgta caccttctta tgccgggtcg tgtcagcaat aattaaatcg    780
ggttttaatg aagcgatttt ttccatgctt ggctgtgagc gagtgccgac agatgtgtag    840
ccgtcaattt tcttcagcac atccttgttg atcagctgct tcgctttgtt gtcatcggca    900
accccgacag gcgtaatgcc gagatcaagc agtgtatcaa taaaacctag ctcaagaaca    960
```

```
acaacccgct tcggatgctc aggcacattt gtcttccctc aatcatgtgt taccgccact    1020
ttatgttctt tactgttttg attgccgctt gaagacgagc aagcagccgt taagacagaa    1080
agaagtaaaa ctgtaagaat aatcagtgtt tttttcatat gttccagtct ctcctgttgg    1140
tagtttctat ggttaagatg tccaagagta gtataacacg gaatgagaat cattatcacc    1200
aattattttt aaaatgagaa gagaaagttc ggcttacagg aaaatcttgt ttcgcgacac    1260
agcagttcag cagctgatca tcctgtccac aaaaaagctt gcagaaaaat aacattctct    1320
gcaagctgat cctgttaaag cttcacaatc actcttcctt gaatgcgatt ttgcaaaata    1380
tcttttaacg cacccggcgt ttcttccaat gatacttccc tgtccacgat ggtcagcagc    1440
tgatcaggct tgagatcaga agacatgcgc tcccaaacag cggctctgac gtccatcgga    1500
caatatactg aatcgattcc gagcaggctt actccgcgaa gaataaaagg atacacggtt    1560
gccggaactt ctcctccgcc ggttaagccg ctcactgcga cagatccgcc gtattgaatt    1620
ttgcttaaaa gcgaggcaag ctgttttccg ccgactggac aaccgctcc ctgccattgc     1680 tgcttggaca gcgccttaag cgttccgtca tagacatctt ccctgctgat tacttcgctt    1740
gcaccaagct gtttcaaata atcagccgcc tcccggtttc cggtacttgc caccacatca    1800
taaccccgct tgttcagcat cgataccgca attccgccga caccgccggt tgctcctgtg    1860
actagcacgc tgcctttttc cggagacaga ccgttctgtt caagccgatg cactgataac    1920
gccgcagtaa atcccgccgt tccgtacacc atcgcttctt ttaacgaaag attctgtggc    1980
aaaggcacca gccagtcacc aggcaccgaa gcgtattcac ttaatccgcc atcacgtgag    2040
acaccgagct catagcttgt cgcgatcacc tcatcccct ccgcaaaacg cggatcattg     2100
gaagagacga ccgtacccgc agcatcaatg cctaaaataa gcggatactc tctgacgata    2160
ttgcctcctg cttttccggc cagaccatct ttgtaattaa tgccggaata agcaacttta    2220
atcaggacac catccttcgg caaatcctct gttgatatgg ttttcacatg gactgaaaca    2280
tcatcggcat ttttttctgc ctgcaaggct tgaaataacg ttgacattcg gcacactcct    2340
tttcatttat atcgtaaccg aagaacgttc aaaaaaccaa atcatcaagc cgccattttc    2400
acttcgccgg cacattgaga caataatgga caaatccggt atcctcttca tagccgtttt    2460
gctcatacaa gcttcttgcc ttccggttgt ggtgctcagt ctgaagtgtt aaacattttg    2520
ccccgttttg ccctgcataa tcctttgcgg cagaaagcag ccggccgccg gctccctttg    2580
tacgcgcatg aggaacgaca aataagtcat ttaatatgta tatccttttc attgacacag    2640
aagaaaacgt tggatagagc tgggtaaagc ctatgaattc tccatttct tctgctatca     2700 aaataacaga ctcgtgattt tccaaacgag cttcaaaaa agcctctgcc ccttgcaaat     2760
cggatgcctg tctataaaat tcccgatatt ggttaaacag cggcgcaatg gcggccgcat    2820
ctgatgtctt tgcttggcga atgttcatct tatttcttcc tccctctcaa taattttttc    2880
attctatccc ttttctgtaa agtttatttt tcagaatact tttatcatca tgctttgaaa    2940
aaatatcacg ataatatcca ttgttctcac ggaagcacac gc                       2982
```

<210> SEQ ID NO 39
<211> LENGTH: 91
<212> TYPE: DNA
<213> ORGANISM: Bacillus subtilis

<400> SEQUENCE: 39

```
gctgataaac agctgacatc aactaaaagc ttcattaaat actttgaaaa aagttgttga      60
```

```
cttaaaagaa gctaaatgtt atagtaataa a                                    91

<210> SEQ ID NO 40
<211> LENGTH: 91
<212> TYPE: DNA
<213> ORGANISM: Artificial Sequence
<220> FEATURE:
<223> OTHER INFORMATION: synthetic

<400> SEQUENCE: 40
gctgataaac agctgacatc aactaaaagt ttcattaaat actttgaaaa aagttgttga     60
cttaaaagaa gctaaatgtt atagtaattg t                                    91

<210> SEQ ID NO 41
<211> LENGTH: 254
<212> TYPE: DNA
<213> ORGANISM: Artificial Sequence
<220> FEATURE:
<223> OTHER INFORMATION: synthetic

<400> SEQUENCE: 41
tctagataca taaaaaaccg gccttggccc cgccggtttt ttattatttt tcttcctccg     60
catgttcaat ccgctccata atcgacggat ggctccctct gaaaattta acgagaaacg    120 gcgggttgac ccggctcagt cccgtaacgg ccaagtcctg aaacgtctca atcgccgctt   180
cccggtttcc ggtcagctca atgccgtaac ggtcggcggc gttttcctga taccgggaga   240
cggcattcgt aatc                                                      254

<210> SEQ ID NO 42
<211> LENGTH: 3000
<212> TYPE: DNA
<213> ORGANISM: Bacillus subtilis

<400> SEQUENCE: 42
aacgcctcac tcctcacatc aacccgttac ttctattgta atcataaatt caaattctta     60
gaaccaagct gtgttccgca cttttccacc cttttaagca tggaaacccc gatcgctggg    120
aaaactaaca atgtttggag tgatgcaaat gaaaaaaata gtggcagcca tcgtggtaat    180
cggtcttgtg tttatcgcat ttttttatct ttacagccga tcaggcgatg tgtatcaatc    240
ggtagacgcg gatttgatca cactgtcttc aagcggccag gaagatatcg agattgaaaa    300
aagacagcac gtcaaagata tgctggatat tatgaatcag ggaaaacagg tgaagacaga    360
aaaaacatca gcccctgatt acgaagggac aatcaagttt cataaagacc ggtatgactc    420
attcagacta tggattgacg gcagccagca agccgttttt ttgaaggatg gcacatacta    480
caaattaagc aaaaatgata caaaggcgct gctaaatatt attaaaaaag aagcaaagga    540
ttgaaaatga aaaagcgaag ctaaccgctt cgcttttca ttttattggg gcaaaatatc     600
tctcagtgcc cgtctgagca ttttcccccgt cgcatttttc ggaatatcgt caagaaacgt    660
aatggcggca ggccgcttgt attttgccag atgcttttcg cagtgctgca tgatgtcctc    720
ctctgttacc ccagagcgtt tcggcaccac atatcccttt accgcttccc cgctttgggg    780
gtccggcacg ccgatgacaa ccgcctcctt gacgtccgga tggctgtaca gcacctcctc    840
cacctcccgc ggatacacat tgtatcctcc tacaatgatc atgtcttttt tccggtcaac    900
aatgtaaaaa tagccgtcct catcccgtct tgccaagtcc cccgtataaa gccacccgtc    960
ttttaatgca tgctctgttt ccatcggcat tttataatag cccttcatca cattgggggc   1020
tttcacgatc aattcgccga cctggtgagc gggcagctcg cgtccgagcg gatctacgac   1080
```

```
cttgttttcg acatgtaaga tacttgtccc gatggagccc ggctttctgc ccctgtcaaa    1140
cgggttaaag cacgtgacgg gtgatgcttc cgagagcccg tagccttcca aaatggtaac    1200
accgaatttt tcttcaaacg ccgtcagcaa cgcgactggc atggacgcgc ctcccgaaat    1260
gcacagccgg atcgaagaaa aatcatcttt ctttccgttt tcatgctgaa acaagtagtt    1320
atacattgta ggcacaccgg caaaaatggt cgcctgctgc tgcttaacaa gcttaaaaac    1380
agatgccgga ctgaattgag gctcaatcaa tacagttgcg ccgctcatca gcggtgcatt    1440
catacagacg gttaaacaaa acacgtgaaa catgggaaga gcgcagacca cattgtccct    1500
ctcatccatt cccaaatagc ctgcgacatc gttggcattg ctgtacaaat tctgatgtgt    1560
cagcatcgcg cctttcggtt ttccagtcgt tcctgacgta tataaaataa ccgcggtatc    1620
atcaggtaca ggttcttggt tttgtttagc ggcagatgtc ggccgcaata tttttgcaaa    1680
cgttgtcatt ttcatcctga cctctgggtc cgcagcttcc ggctcggcct ccccgtctg     1740 gcataaaatg acgagctcaa cctttggcag cgattcatgc atgctctcat aaagcggcaa    1800
aagctggcta acgcccacga ttgcctttac atcgccattt gtcagcatat aaccaatttc    1860
tgtcggcgta tacaacggat tgatgggaac aactacgatc ccagctttta aagcgccaaa    1920
aaacgcgatg ataaaatcag gcgaattgcc aagcagcaaa gctaaatggt ccccttctc     1980 cataccggct tcctgaaggc cgtccgcaaa tcgctgaata tattcattca gctcttgata    2040
cgtcatcatg tgatctttaa acctgcatgc gatgctgtcg ggcttctcag atgctgtttc    2100
ttccaatttt gaaacaagat tcattctccc acccccttaag tgaatgaata gtcattcatt    2160
attgaagcca agctttcttc tccattatag agaaacagaa aaaaacactc aagagcaaaa    2220
agccctgagt gtcagtactg tcatagtttc ttcaatgctt cggcaatcgg cgtatctcct    2280
tctgtcagat caaggcccg attttccgta ttcttctcat ctaaagaggc aatgaccgtt     2340
tttgcaacgt catcacggga aataaatccc cgctccagat ccttcgctgc tgaaacagtt    2400
cccgttccag gctcattgcg aaggcctccc ggacggataa tcgtataggt taaaccgctc    2460
gcttccagaa ttttatcagc ataatgcttg gccacataat aaggcttgag tgcctcattc    2520
caattttcac ggttatgggc ttgcagggcg ctgaccataa taaaccgttt gattccggca    2580
atggccgcag cttcaatggc ttttgccgct ccatcaagat ccaccagcag cgttttatca    2640
tagcctgtgc tgccgccgga accggctgtg aaaatgatcg cgtcacaacc ttttgccgca    2700
gcggcgattt cttccgggct gccctccaga ttcgcaagca cagcttctgc accggcagct    2760
tcaagagacg ctttctgttc ttcttttctg accatcgctc tgatggaatg atcaggatta    2820
tcttggaata agagacgag tctttgcccg atttgtccgt tcgctccgat taaaaacact     2880
ttcatgtgaa tccctcctgc ctccattatt tcaaaaacac aaccgctctt tcaaacgatg    2940
tgttttgcct tagtaaatca gatcaaggaa atcctctttc gtaatgttcc caaagtaatg    3000
```

<210> SEQ ID NO 43
<211> LENGTH: 576
<212> TYPE: DNA
<213> ORGANISM: Bacillus subtilis

<400> SEQUENCE: 43

```
atgagtcaga aaacagacgc acctttagaa tcgtatgaag tgaacggcgc aacaattgcc      60
gtgctgccag aagaaataga cggcaaaatc tgttccaaaa ttattgaaaa agattgcgtg     120
ttttatgtaa acatgaagcc gctgcaaatt gtcgacagaa gctgccgatt ttttggatca     180
```

| | |
|---|---:|
| agctatgcgg gaagaaaagc aggaacttat gaagtgacaa aaatttcaca caagccgccg | 240 |
| atcatggtgg acccttcgaa ccaaatcttt ttattcccta cactttcttc gacaagaccc | 300 |
| caatgcggct ggatttccca tgtgcatgta aaagaattca aagcgactga attcgacgat | 360 |
| acggaagtga cgttttccaa tgggaaaacg atggagctgc cgatctctta taattcgttc | 420 |
| gagaaccagg tataccgaac agcgtggctc agaaccaaat tccaagacag aatcgaccac | 480 |
| cgcgtgccga aaagacagga atttatgctg tacccgaaag aagagcggac gaagatgatt | 540 |
| tatgatttta ttttgcgtga gctcggggaa cggtat | 576 |

<210> SEQ ID NO 44
<211> LENGTH: 9216
<212> TYPE: DNA
<213> ORGANISM: Artificial Sequence
<220> FEATURE:
<223> OTHER INFORMATION: synthetic

<400> SEQUENCE: 44

| | |
|---|---:|
| catcggacag ctcttgcttg atatcttcaa aatgacgccg gctcatgtca tgtcaacttt | 60 |
| tgtcgtatct ggagcgatcc ttgacggatt cggcatttac gaccgtttta tcgaatttgc | 120 |
| cggtgccggg gctacagtcc cgattgtcag cttcggccac tctcttttgc acggcgcgat | 180 |
| gcaccaggct gagaaacatg gctttatcgg aatcggcatg gggatatttg aactgacatc | 240 |
| tgccggtata tctgccgcta tcttgttcgc ttttcttgtt gccgtgattt ttaaaccgaa | 300 |
| aggataaagg aaaatgccag caaaacgcaa ggtcattttg gtcacagacg gcgatatata | 360 |
| cgctgcaaaa gcaatcgaat atgcagcaag aaaaacgggt ggccgctgca tttcccaatc | 420 |
| ggcggggaat ccgagcgtta aacaggacc ggagcttgta accatgatcc tgcaaccccc | 480 |
| tcatgatcct gtattcgtca tgtttgatga ttccggactt caaggtgaag gcccgggaga | 540 |
| gacagctatg aaatatgtag cgatgcatcc cgatatcgag gtgctcggag tcatcgccgt | 600 |
| cgcttcaaaa actcattatg cagagtggac gagagtcgat gtatcaatcg atgcagaagg | 660 |
| cgaactgaca gagtacggcg tcgataaaca cggggtcaaa gagttcgatg tcaaacgaat | 720 |
| gaatggtgat acagtctatt gccttgacca gctggatgtt ccgatcattg tcggaatcgg | 780 |
| tgatatcggt aagatgaaca gaaaagacga tgtggaaaaa ggttcgccga ttacaatgaa | 840 |
| agcggtcgag ctcatttag aaaggagcgg gtatcatgag tgctcaaaag caagagaaga | 900 |
| cgaacgtatt ccttgatcct tctaagaatg aagcgtattt caagaagcgg gtcggcatgg | 960 |
| gagaaagctt tgaccttggc gtacggaagg tctttattct cggacatgaa gttcagcttt | 1020 |
| attatgtcaa cggattgtgc gacacacaat acatcattca cctgttaaga gaactggtgc | 1080 |
| atctgaatga taaagaaaaa gaatcgggcg aggtcgaaga catcgtcgaa acaggctttt | 1140 |
| tgaaccagca ggtttcaaaa gcggaaacgc ttgatgaagc tgtcgaccaa gtgttgtcag | 1200 |
| gactggttgc catcatcgtc gaagatgcgg gctttgcttt tatcatcgat gtcagaagct | 1260 |
| acccgggcag aacgccggaa gaacctgata cagaaaaagt cgtacgcggt gcaagggacg | 1320 |
| gactcgtcga gaacatcatc gtcaacacag ccctgattag acgccggatc agagatgagc | 1380 |
| gcttgcgcta caaatgctt catatcggtg aacgctctaa aacagacatc tgcctctgct | 1440 |
| atttggaaga cgttgcagat cccgatcttg ttgaagtatt aaaaaagaa attgaagatg | 1500 |
| tgaagatcga cgggctgccg atgtcggata aatcggtaga ggaattcctg gtcggccaag | 1560 |
| gctacaatcc gtttccgctt gtcaggttta cggaaagggc agacgtagcc gcaagccata | 1620 |
| ttttagaggg gcatgtcatc gtgatcgtcg atacgtcgcc aagcgtcatc atcacaccga | 1680 |

```
ccactttgtt tcaccatgtt cagcatgctg aggaatacag acagacgccg gctgttggga   1740
cgttttttaag gtgggtgcgg ttttcggta ttttggcctc cacctttttg ctgccgcttt   1800
ggctgctgtt tgtcattcat ccgtcgctct tgcctgataa tttatcgttt atcgggttga   1860
ataaagacac ccatattccg attatcatgc agattttcct ggcggatctc ggcgtcgaat   1920
ttttaagaat ggccgccatt catacgccga cggcgctttc gactgcaatg gcctgatcg    1980
ccgctgtatt gatcggcgat atcgcgatca atgtcggctt gttttctccc gaagtcattt   2040
tatacgtttc cctctcggca atcggagcct acacgacacc aagctacgag ctgagcctgg   2100
cgaataaaat ggtgaagctg tttatgctga tattggtggc gcttttaaa gtggagggat    2160
ttgtcatcgg attaacgatc ttaactatag tgatgacttc gatcaggtca ttgcgaacgc   2220
cttacttatg gcctctcctc ccgttcaatg gaaaagcgtt ttggcatgtt ctcgtgcgca   2280
cgtccgttcc aggggaaaa gtcaggccga gcatcgttca tccgagaaac cgctccagac    2340
agccgtgaag ccggcattcg aagaggcttt tccccgggga aaagcctctt tttcaataat   2400
cgaattccgg tctttgagta ccgatgcctc tgtattcatt ggcagagatc gcgactgccc   2460
ggaggctgca gatgttgttc tgtcttctga tcggatagac gacatacagc atttcgcggc   2520
cgtacgggtc aatcgttgac gaatgaagga aaacctcagt tcctctccgc caaaatctcg   2580
tattcgccgg agctgtaata atctgcccctt cataaggctc ataaattctc tgttcataat   2640
gcgcagccgg ctgataaggg gcgtatacat cttcaggtgc atagccggga gcggggtgt    2700
agggatagcg atttgatac atatgataac ctctttccca cttcgttttt tggttttcat    2760
ctttaagatt atattcaggt aaatgcctat ttgtatgggc gaaaatctca gcttttcggc   2820
tctttttttta ttgaatggac gttgtgtatg cctatttcta tcaagcgctg ttttctgtta  2880
ttctataatc aatagaatgg attagttgtt tagggaatca tttcctttat aaatcaagaa   2940
aatttggaca aatggtggtt tagtttttaa aacgaaatgt tataatacaa cataagaatc   3000
gcactatcat gaagccggaa gatgcatcgg gcagcaaccg gagcgcccct tgcacctttg   3060
tcgatagaga aagagggaat gacaattgtt tttacacggt actagcagac aaaatgaaag   3120
agggcaccctc gaaatcggcg gtgtcgatgt tctatcattg gcagaaagat acggaacacc   3180
tctttatgta tacgtgtcg cgctgattag agagcgcgcc cgaaaattcc agaaggcatt    3240
caaggaagcc ggtttaaaag cgcaggtagc gtatgcaagc aaggcgtttt catcggttgc   3300
catgattcag cttgccgaac aagagggggct gtctctggat gtggtatcgg gaggagagct   3360
tttcactgcg atcaaagcag ggttcccagc tgagcggatt cattttcacg gaaacaataa   3420
gagccctgaa gaactagcca tggcgctgga gcatcaaatc ggctgcatcg tgctcgataa   3480
ctttcacgag atcgccatta cagaagatct ttgcaagcga tcaggacaaa ctgtagacgt    3540
tttgctcaga atcactccgg gagttgaagc gcacacgcac gattatatta cgacggggca   3600
ggaagattcc aaattcggtt tgatctgca taatggacag gtcgaacaag ccatcgaaca    3660
agtcctccgc tcgtctgcgt ttaagctcct cggcgtgcac tgccacatcg gttcgcaaat   3720
ttttgatacg gcaggatttg tccttgcagc agacaagatt ttcgagaagc ttgcggaatg   3780
gcgggagact tactctttca ttccggaagt gctcaatctt ggcgggggct tcggcatccg   3840
ctatacaaaa gacgacgagc cgcttgcagc tgatgtttat gttgaaaaaa tcatcgaggc   3900
ggtcaaagca aatgccgagc atttcggctt tgacatccct gagatttgga tcgaaccagg   3960
ccggtctctc gtcggtgatg cggggactac gctgtacacg atcggttctc aaaaagaggt   4020
```

-continued

| | |
|---|---|
| gccgggcatt cgcaaatatg tagccatcga cggcggcatg agcgataata tcaggccggc | 4080 |
| gctttatgag gcaaaatatg aagcagccgt cgccaacagg atgaacgatg cttgtcatga | 4140 |
| taccgcatca atcgcaggaa aatgctgcga aagcggagat atgctgattt gggatttgga | 4200 |
| aatccccgaa gttcgcgacg gagatgtgct cgccgttttc tgcaccggtg cgtacggcta | 4260 |
| cagcatggcc aacaactaca accgcattcc gcgcccggcc gtcgtctttg tcgaggacgg | 4320 |
| ggaagcgcag ctcgtcattc agagagagac gtatgaggat atcgtcaagc tggatctgcc | 4380 |
| gctgaaatcg aaagtcaaac aataaaaaaa tggagattcc ctaagagggg ggtctccatt | 4440 |
| tttaattcaa tcgctgataa acagctgaca tcaactaaaa gcttcattaa atactttgaa | 4500 |
| aaaagttgtt gacttaaaag aagctaaatg ttatagtaat aaaacagaat agtcttttaa | 4560 |
| gtaagtctac tctgaatttt tttaaaagga gagggtaaag atgaaacaac aaaaacggct | 4620 |
| ttacgcccga ttgctgacgc tgttatttgc gctcatcttc ttgctgcctc attctgcagc | 4680 |
| tagcgcagca gcgacaaacg gaacaatgat gcagtatttc gagtggtatg tacctaacga | 4740 |
| cggccagcaa tggaacagac tgagaacaga tgccccttac ttgtcatctg ttggtattac | 4800 |
| agcagtatgg acaccgccgg cttataaggg cacgtctcaa gcagatgtgg ggtacggccc | 4860 |
| gtacgatctg tatgatttag gcgagtttaa tcaaaaaggt acagtcagaa cgaagtatgg | 4920 |
| cacaaaagga gaacttaaat ctgctgtcaa cacgctgcat tcaaatggaa tccaagtgta | 4980 |
| tggtgatgtc gtgatgaatc ataaagcagg tgctgattat acagaaaacg taacggcggt | 5040 |
| ggaggtgaat ccgtctaata gatatcagga aacgagcggc gaatataata ttcaggcatg | 5100 |
| gacaggcttc aactttccgg gcagaggaac aacgtattct aactggaaat ggcagtggtt | 5160 |
| ccatttttgat ggaacggatt gggaccagag cagaagcctc tctagaatct tcaaattcca | 5220 |
| tggaaaggcg tgggactggc cggtttcttc agaaaacgga aattatgact atctgatgta | 5280 |
| cgcggactat gattatgacc atccggatgt cgtgaatgaa atgaaaaagt ggggcgtctg | 5340 |
| gtatgccaac gaagttgggt tagatggata cagacttgac gcggtcaaac atattaaatt | 5400 |
| tagcttttctc aaagactggg tggataacgc aagagcagcg acgggaaaag aaatgtttac | 5460 |
| ggttggcgaa tattggcaaa atgatttagg ggccctgaat aactacctgg caaaggtaaa | 5520 |
| ttacaaccaa tctcttttttg atgcgccgtt gcattacaac ttttacgctg cctcaacagg | 5580 |
| gggtggagcg tacgatatga gaaatattct taataacacg ttagtcgcaa gcaatccgac | 5640 |
| aaaggctgtt acgttagttg agaatcatga cacacagcct ggacaatcac tggaatcaac | 5700 |
| agtccaaccg tggtttaaac cgttagccta cgcgtttatt ctcacgagaa gcggaggcta | 5760 |
| tcctgcggta ttttatggag atatgtacgg tacaaaagga acgacaacat atgagatccc | 5820 |
| tgctctcttaaa tctaaaatcg aacctttgct taaggctaga aaagactatg cttatggaac | 5880 |
| acagagagac tatattgata acccggatgt cattggctgg acgagagaag gggactcaac | 5940 |
| gaaagccaag agcggtctgg ccacagtgat tacagatggg ccgggcggtt caaaaagaat | 6000 |
| gtatgttggc acgagcaatg cgggtgaaat ctggtatgat ttgacaggga atagaacaga | 6060 |
| taaaatcacg attggaagcg atggctatgc aacatttcct gtcaatgggg gctcagtttc | 6120 |
| agtatgggtg cagcaatgaa agcttctcga ggttaacaga ggacggattt cctgaaggaa | 6180 |
| atccgttttt ttattttcaa gcacgaaaaa cacttcccgg tgatcgggag gtgttttttg | 6240 |
| ttaaaaagat catgacatgc atagaacagc gaccgggcta attgtatata atattgtgaa | 6300 |
| tttaacaaaa aatttacaaa ggagatgata aaggcaatga ccagggtgaa aaggatgaga | 6360 |
| tttgctgatt tgttggattt agaggcggag tagatgaaac cggccaaagt atccctactc | 6420 |

```
caccgattgc tccagtgcct gaagcaatgt gttgattgta acacagtaaa tcgttttaca    6480
gcaataaaca ttttttgtaa tattttattg atttcggctg tgatctcatt cccatattct    6540
gctgcggccc atggcgcaac acagtccggc gatcaatatt caagctttga agaattggag    6600
cggaatgaag atccagcttc ttaccgaatt acggagaaga acgcaagagt gccgatgctc    6660
atcatggcca tccatggagg cggcatcgaa cccggaacga gcgaaatcgc caatgaagtg    6720
tccaaaaact attccctgta cttgtttgaa gggctgaaat catcaggcaa tacgacctt     6780 cacattacaa gcacgcgttt tgacgagcca gcggcgctcg caattactgc aagccaccag    6840
tatgtcatgt cgctccacgg ctattacagt gaagaccgcg atattaaagt aggcggcaca    6900
gaccgcgcta aaatcagaat attggttgat gagctgaacc gctcggggtt tgccgctgaa    6960
atgctgggga cagatgacaa gtatgccgga acccatccga ataacatcgc caacaagtcg    7020
ctttccgggc tgagcattca gcttgaaatg agcacgggtt tccgcaaatc tttattcgac    7080
cggtttacac taaagacag gcggcgacg caaaacgaaa cgttttaccg atttacaaag     7140
ctgctgacag attttattca tgaaaactat gaagaagacg aggggattt cccctctgca     7200 aaataaaac accccttca agtgaaaaag gaggtgtttc ggcggttgtg ttaaccgttg      7260
gactctgagg tgccgccgcc ggtgaatacg gaaacgatgg cgttccacag agacacaaag    7320
aagtcgatca gtttttgaag aaagttttgt ccttcttcag aatccaagaa tttcgtgatt    7380
ttatcctttg ctttgtcaag ctggtctcca acctggttcc agtcgatatt aatattttc     7440 atgttattaa ataaagatat aagagagttt ttctgatctt ctgtgagtgt cacgccaagt    7500
tcggaagcag ccgaatcaat cgttttctcc aattcctctt ttgactcggg aactccgttt    7560
ttcgagattt cttccttgac tttggccatc agcgctgacg cgttttcact gccgattttc    7620
tcgccaagct ctgaagtggt gacaagctct tcattcgcga ccttttttcac atcttcggaa    7680 atttttttcgc ccgaagtcgt ttcatacgct ttcatcaatc cggttaaagc ggctgtgcct    7740
gacacttcaa acggagcggt gacatagact ttggcgtctt ttacaccggc cgtcatcagc    7800
gcgttcaaat acatctcatc tgtaattctg ctgatattgt gtgtctgaac ttccaaaccg    7860
gtgccttttt tcgctacggt aattgaagaa gaagaaatcg ctcttgttcc gatttgtgct    7920
ttcggtatat aatcccctaa atatttatgc tcctcatcat ttgtcacctc gatgatggtc    7980
gcattttcag gcgcattcat ttcttttaat acttttttgtc tgtcctggct tgacaagtct    8040
ttccccagcg tgacgatgac atcacccact gcggcgtcag cgaagctgac ctgcgggaaa    8100
atgagcagac acaatgctgt aaagattcct agtatcgatt ttttcaagct caatgccctc    8160
cttaaaaatg caggcttcag gcagaattgc tgtacttttta aagaagcctg ccggaacgga    8220
aataatgcgt tccgaaatat agacggatga aagatgagtg aggtttcaaa gaaaaaaaga    8280
gagaattttc tcttcaagtc aaatgccctc ccggcatcgt atctcgccgc tctttttatca    8340 ttcatgattt tcacaggcga ttcaacctt ttttaaaatt ttttacaaaa acgatacaag     8400
agcggcgttt atttcggtcg attggctctc tgcttcttca atatgatata atgacccttg    8460
tgaaatgaaa ggagagaatc aagatggcta aaaaggata catacaactg acaaacggca    8520
aaaaaatcga gtttgaacta tatccggatg cggcgccggg aactgtcgcc aactttgaaa    8580
aacttgcaaa cgaagggttc tatgacgggc tgaagttcca ccgcgtcatc ccgggcttcg    8640
tcagccaggg aggctgcccg cacggcaccg gaacaggcgg acctggatat acgattaaat    8700
gcgagacaga agggaatccg cacaaacacg aagccggttc tctctcaatg gctcacgcag    8760
```

| | |
|---|---|
| gaaaagatac cggaggcagc caattttta tcgtccatga gcctcagccg cacttgaacg | 8820 |
| gcgttcacac cgttttcgga aaggtcacat caggccttga tgccgtcact tcaatggagc | 8880 |
| agggacaagg catggaaaaa gtcgaagtat ttgatgcata atcagagagc gcaaaaaaca | 8940 |
| gcccgcttag ccgggctgtt ttttgtctg taacggtgtt tattttccag gtgcaacagg | 9000 |
| acttgaggcc gattcttcgt ccacatcctg ataggaaata acgatgctaa taaataaat | 9060 |
| aattgtgaaa aaatgaccct ttatgtaaaa tatattcaag tgaagagcta gatagagaac | 9120 |
| gcaatctgta aaaaggaag gggcgtaagg ggtgagcgta aaatcccat cgacggcagt | 9180 |
| cggcgtaaaa attaatgact ggtataacgc gatacg | 9216 |

<210> SEQ ID NO 45
<211> LENGTH: 9214
<212> TYPE: DNA
<213> ORGANISM: Artificial Sequence
<220> FEATURE:
<223> OTHER INFORMATION: synthetic

<400> SEQUENCE: 45

| | |
|---|---|
| catcggacag ctcttgcttg atatcttcaa aatgacgccg gctcatgtca tgtcaacttt | 60 |
| tgtcgtatct ggagcgatcc ttgacggatt cggcatttac gaccgtttta tcgaatttgc | 120 |
| cggtgccggg gctacagtcc cgattgtcag cttcggccac tctcttttgc acggcgcgat | 180 |
| gcaccaggct gagaaacatg gctttatcgg aatcggcatg gggatatttg aactgacatc | 240 |
| tgccggtata tctgccgcta tcttgttcgc ttttcttgtt gccgtgattt ttaaaccgaa | 300 |
| aggataaagg aaaatgccag caaaacgcaa ggtcattttg gtcacagacg gcgatatata | 360 |
| cgctgcaaaa gcaatcgaat atgcagcaag aaaaacgggt ggccgctgca tttcccaatc | 420 |
| ggcggggaat ccgagcgtta aaacaggacc ggagcttgta accatgatcc tgcaaacccc | 480 |
| tcatgatcct gtattcgtca tgtttgatga ttccggactt caaggtgaag gcccgggaga | 540 |
| gacagctatg aaatatgtag cgatgcatcc cgatatcgag gtgctcggag tcatcgccgt | 600 |
| cgcttcaaaa actcattatg cagagtggac gagagtcgat gtatcaatcg atgcagaagg | 660 |
| cgaactgaca gagtacggcg tcgataaaca cggggtcaaa gagttcgatg tcaaacgaat | 720 |
| gaatggtgat acagtctatt gccttgacca gctggatgtt ccgatcattg tcggaatcgg | 780 |
| tgatatcggt aagatgaaca gaaaagacga tgtggaaaaa ggttcgccga ttacaatgaa | 840 |
| agcggtcgag ctcatttag aaaggagcgg gtatcatgag tgctcaaaag caagagaaga | 900 |
| cgaacgtatt ccttgatcct tctaagaatg aagcgtattt caagaagcgg tcggcatgg | 960 |
| gagaaagctt tgaccttggc gtacggaagg tctttattct cggacatgaa gttcagcttt | 1020 |
| attatgtcaa cggattgtgc gacacacaat acatcattca cctgttaaga gaactggtgc | 1080 |
| atctgaatga taagaaaaa gaatcgggcg aggtcgaaga catcgtcgaa acaggcttt | 1140 |
| tgaaccagca ggtttcaaaa gcggaaacgc ttgatgaagc tgtcgaccaa gtgttgtcag | 1200 |
| gactggttgc catcatcgtc gaagatgcgg gctttgcttt tatcatcgat gtcagaagct | 1260 |
| acccgggcag aacgccggaa gaacctgata cagaaaagt cgtacgcggt gcaagggacg | 1320 |
| gactcgtcga gaacatcatc gtcaacacag ccctgattag acgccggatc agagatgagc | 1380 |
| gcttgcgcta caaaatgctt catatcggtg aacgctctaa acagacatc tgcctctgct | 1440 |
| atttggaaga cgttgcagat cccgatcttg ttgaagtatt aaaaaaagaa attgaagatg | 1500 |
| tgaagatcga cgggctgccg atgtcggata atcggtaga ggaattcctg gtcggccaag | 1560 |
| gctacaatcc gtttccgctt gtcaggttta cggaaagggc agacgtagcc gcaagccata | 1620 |

```
tttagaggg gcatgtcatc gtgatcgtcg atacgtcgcc aagcgtcatc atcacaccga    1680
ccactttgtt tcaccatgtt cagcatgctg aggaatacag acagacgccg gctgttggga    1740 cgttttaag gtgggtgcgg tttttcggta ttttggcctc cacctttttg ctgccgcttt    1800
ggctgctgtt tgtcattcat ccgtcgctct tgcctgataa tttatcgttt atcgggttga    1860
ataaagacac ccatattccg attatcatgc agattttcct ggcggatctc ggcgtcgaat    1920
ttttaagaat ggccgccatt catacgccga cggcgctttc gactgcaatg ggcctgatcg    1980
ccgctgtatt gatcggcgat atcgcgatca atgtcggctt gttttctccc gaagtcattt    2040
tatacgtttc cctctcggca atcggagcct acacgacacc aagctacgag ctgagcctgg    2100
cgaataaaat ggtgaagctg tttatgctga tattggtggc gcttttaaa gtggagggat    2160 ttgtcatcgg attaacgatc ttaactatag tgatgacttc gatcaggtca ttgcgaacgc    2220
cttacttatg gcctctcctc ccgttcaatg gaaaagcgtt ttggcatgtt ctcgtgcgca    2280
cgtccgttcc aggggaaaa gtcaggccga gcatcgttca tccgagaaac cgctccagac    2340
agccgtgaag ccggcattcg aagaggcttt tccccgggga aaagcctctt tttcaataat    2400
cgaattccgg tctttgagta ccgatgcctc tgtattcatt ggcagagatc gcgactgccc    2460
ggaggctgca gatgttgttc tgtcttctga tcggatagac gacatacagc atttcgcggc    2520
cgtacgggtc aatcgttgac gaatgaagga aaacctcagt tcctctccgc caaaatctcg    2580
tattcgccgg agctgtaata atctgccctt cataaggctc ataaattctc tgttcataat    2640
gcgcagccgg ctgataaggg gcgtatacat cttcaggtgc atagccggga gcggggtgt    2700 agggatagcg atttggatac atatgataac ctctttccca cttcgttttt tggttttcat    2760
ctttaagatt atattcaggt aaatgcctat ttgtatgggc gaaaatctca gcttttcggc    2820 tctttttta ttgaatggac gttgtgtatg cctatttcta tcaagcgctg ttttctgtta    2880
ttctataatc aatagaatgg attagttgtt tagggaatca tttcctttat aaatcaagaa    2940
aatttggaca aatggtggtt tagttttta aacgaaatgt tataatacaa cataagaatc    3000
gcactatcat gaagccggaa gatgcatcgg gcagcaaccg gagcgcccct tgcacctttg    3060
tcgatagaga aagagggaat gacaattgtt tttacacggt actagcagac aaaatgaaag    3120
agggcacctc gaaatcggcg gtgtcgatgt tctatcattg gcagaaagat acggaacacc    3180
tctttatgta tacgatgtcg cgctgattag agagcgcgcc cgaaaattcc agaaggcatt    3240
caaggaagcc ggtttaaaag cgcaggtagc gtatgcaagc aaggcgtttt catcggttgc    3300
catgattcag cttgccgaac aagaggggct gtctctggat gtggtatcgg gaggagagct    3360
tttcactgcg atcaaagcag ggttcccagc tgagcggatt catttcacg gaaacaataa    3420 gagccctgaa gaactagcca tggcgctgga gcatcaaatc ggctgcatcg tgctcgataa    3480
ctttcacgag atcgccatta cagaagatct ttgcaagcga tcaggacaaa ctgtagacgt    3540
tttgctcaga atcactccgg gagttgaagc gcacacgcac gattatatta cgacggggca    3600
ggaagattcc aaattcggtt ttgatctgca taatggacag gtcgaacaag ccatcgaaca    3660
agtcctccgc tcgtctgcgt ttaagctcct cggcgtgcac tgccacatcg gttcgcaaat    3720
ttttgatacg gcaggatttg tccttgcagc agacaagatt tcgagaagc ttgcggaatg    3780 gcgggagact tactctttca ttccggaagt gctcaatctt ggcggggct tcggcatccg    3840 ctatacaaaa gacgacagag cgcttgcagc tgatgtttat gttgaaaaaa tcatcgaggc    3900
ggtcaaagca aatgccgagc atttcggctt tgacatccct gagatttgga tcgaaccagg    3960
```

```
ccggtctctc gtcggtgatg cggggactac gctgtacacg atcggttctc aaaaagaggt    4020
gccgggcatt cgcaaatatg tagccatcga cggcggcatg agcgataata tcaggccggc    4080
gctttatgag gcaaaatatg aagcagccgt cgccaacagg atgaacgatg cttgtcatga    4140
taccgcatca atcgcaggaa aatgctgcga aagcggagat atgctgattt gggatttgga    4200
aatccccgaa gttcgcgacg gagatgtgct cgccgttttc tgcaccggtg cgtacggcta    4260
cagcatggcc aacaactaca accgcattcc gcgcccggcc gtcgtctttg tcgaggacgg    4320
ggaagcgcag ctcgtcattc agagagagac gtatgaggat atcgtcaagc tggatctgcc    4380
gctgaaatcg aaagtcaaac aataaaaaaa tggagattcc ctaagagggg ggtctccatt    4440
tttaattcaa gctgataaac agctgacatc aactaaaagt ttcattaaat actttgaaaa    4500
aagttgttga cttaaaagaa gctaaatgtt atagtaattg tacagaatag tcttttaagt    4560
aagtctactc tgaattttt taaaggaga gggtaaagat gaaacaacaa aaacggcttt    4620
acgcccgatt gctgacgctg ttatttgcgc tcatcttctt gctgcctcat tctgcagcta    4680
gcgcagcagc gacaaacgga acaatgatgc agtatttcga gtggtatgta cctaacgacg    4740
gccagcaatg gaacagactg agaacagatg ccccttactt gtcatctgtt ggtattacag    4800
cagtatggac accgccggct tataagggca cgtctcaagc agatgtgggg tacggcccgt    4860
acgatctgta tgatttaggc gagtttaatc aaaaaggtac agtcagaacg aagtatggca    4920
caaaaggaga acttaaatct gctgtcaaca cgctgcattc aaatggaatc caagtgtatg    4980
gtgatgtcgt gatgaatcat aaagcaggtg ctgattatac agaaaacgta acggcggtgg    5040
aggtgaatcc gtctaataga tatcaggaaa cgagcggcga atataatatt caggcatgga    5100
caggcttcaa ctttccgggc agaggaacaa cgtattctaa ctggaaatgg cagtggttcc    5160
attttgatgg aacggattgg gaccagagca gaagcctctc tagaatcttc aaattccatg    5220
gaaaggcgtg ggactggccg gtttcttcag aaaacggaaa ttatgactat ctgatgtacg    5280
cggactatga ttatgaccat ccggatgtcg tgaatgaaat gaaaaagtgg ggcgtctggt    5340
atgccaacga agttgggtta gatggataca gacttgacgc ggtcaaacat attaaattta    5400
gctttctcaa agactgggtg gataacgcaa gagcagcgac gggaaaagaa atgtttacgg    5460
ttggcgaata ttggcaaaat gatttagggg ccctgaataa ctacctggca aaggtaaatt    5520
acaaccaatc tcttttttgat gcgccgttgc attacaactt ttacgctgcc tcaacagggg    5580
gtggagcgta cgatatgaga aatattctta ataacacgtt agtcgcaagc aatccgacaa    5640
aggctgttac gttagttgag aatcatgaca cacagcctgg acaatcactg gaatcaacag    5700
tccaaccgtg gtttaaaccg ttagcctacg cgtttattct cacgagaagc ggaggctatc    5760
ctgcggtatt ttatggagat atgtacggta caaaaggaac gacaacatat gagatccctg    5820
ctcttaaatc taaaatcgaa cctttgctta aggctagaaa agactatgct tatggaacac    5880
agagagacta tattgataac ccggatgtca ttggctggac gagagaaggg gactcaacga    5940
aagccaagag cggtctggcc acagtgatta cagatgggcc gggcggttca aaaagaatgt    6000
atgttggcac gagcaatgcg ggtgaaatct ggtatgattt gacagggaat agaacagata    6060
aaatcacgat tggaagcgat ggctatgcaa catttcctgt caatggggc tcagtttcag    6120
tatgggtgca gcaatgaaag cttctcgagg ttaacagagg acggatttcc tgaaggaaat    6180
ccgttttttt attttcaagc acgaaaaaca cttcccggtg atcgggaggt gttttttgtt    6240
aaaaagatca tgcatgcat agaacagcga ccgggctaat tgtatataat attgtgaatt    6300
taacaaaaaa tttacaaagg agatgataaa ggcaatgacc agggtgaaaa ggatgagatt    6360
```

```
tgctgatttg ttggatttag aggcggagta gatgaaaccg gccaaagtat ccctactcca    6420
ccgattgctc cagtgcctga agcaatgtgt tgattgtaac acagtaaatc gttttacagc    6480
aataaacatt tttgtgaata ttttattgat ttcggctgtg atctcattcc catattctgc    6540
tgcggcccat ggcgcaacac agtccggcga tcaatattca agctttgaag aattggagcg    6600
gaatgaagat ccagcttctt accgaattac ggagaagaac gcaagagtgc cgatgctcat    6660
catggccatc catggaggcg gcatcgaacc cggaacgagc gaaatcgcca atgaagtgtc    6720
caaaaactat tccctgtact tgtttgaagg gctgaaatca tcaggcaata cggaccttca    6780
cattacaagc acgcgttttg acgagccagc ggcgctcgca attactgcaa gccaccagta    6840
tgtcatgtcg ctccacggct attacagtga agaccgcgat attaaagtag gcggcacaga    6900
ccgcgctaaa atcagaatat tggttgatga gctgaaccgc tcggggtttg ccgctgaaat    6960
gctggggaca gatgacaagt atgccggaac ccatccgaat aacatcgcca acaagtcgct    7020
ttccgggctg agcattcagc ttgaaatgag cacgggtttc cgcaaatctt tattcgaccg    7080
gtttacacta aagacaggg cggcgacgca aacgaaacg ttttaccgat ttacaaagct     7140
gctgacagat tttattcatg aaaactatga agaagacgga ggggatttcc cctctgcaaa    7200
aataaaacac cccccttcaag tgaaaaagga ggtgtttcgg cggttgtgtt aaccgttgga   7260
ctctgaggtg ccgccgccgg tgaatacgga acgatggcg ttccacagag acacaaagaa     7320
gtcgatcagt ttttgaagaa agttttgtcc ttcttcagaa tccaagaatt tcgtgatttt    7380
atcctttgct ttgtcaagct ggtctccaac ctggttccag tcgatattaa tattttcat    7440
gttattaaat aaagatataa gagagtttt ctgatcttct gtgagtgtca cgccaagttc     7500
ggaagcagcc gaatcaatcg ttttctccaa ttcctctttt gactcgggaa ctccgttttt    7560
cgagatttct tccttgactt tggccatcag cgctgacgcg ttttcactgc cgattttctc    7620
gccaagctct gaagtggtga caagctcttc attcgcgacc ttttttcacat cttcggaaat   7680
ttttcgccc gaagtcgttt catacgcttt catcaatccg gttaaagcgg ctgtgcctga    7740
cacttcaaac ggagcggtga catagacttt ggcgtctttt acaccggccg tcatcagcgc    7800
gttcaaatac atctcatctg taattctgct gatattgtgt gtctgaactt ccaaaccggt    7860
gccttttttc gctacggtaa ttgaagaaga agaaatcgct cttgttccga tttgtgcttt    7920
cggtatataa tcccctaaat atttatgctc ctcatcattt gtcacctcga tgatggtcgc    7980
attttcaggc gcattcattt cttttaatac ttttttgtctg tcctggcttg acaagtcttt    8040
ccccagcgtg acgatgacat cacccactgc ggcgtcagcg aagctgacct gcgggaaaat    8100
gagcagacac aatgctgtaa agattcctag tatcgatttt ttcaagctca atgccctcct    8160
taaaaatgca ggcttcaggc agaattgctg tacttttaaa gaagcctgcc ggaacggaaa    8220
taatgcgttc cgaaatatag acggatgaaa gatgagtgag gtttcaaaga aaaaagaga    8280
gaattttctc ttcaagtcaa atgccctccc ggcatcgtat ctcgccgctc ttttatcatt    8340
catgattttc acaggcgatt caacctttt ttaaaatttt ttacaaaaac gatacaagag     8400
cggcgtttat ttcggtcgat tggctctctg cttcttcaat atgatataat gacccttgtg    8460
aaatgaaagg agagaatcaa gatggctaaa aaaggataca tacaactgac aaacggcaaa    8520
aaaatcgagt ttgaactata tccggatgcg gcgccgggaa ctgtcgccaa ctttgaaaaa    8580
cttgcaaacg aagggttcta tgacgggctg aagttcacc gcgtcatccc gggcttcgtc     8640
agccagggag gctgcccgca cggcaccgga acaggcggac ctggatatac gattaaatgc    8700
```

| | |
|---|---|
| gagacagaag ggaatccgca caaacacgaa gccggttctc tctcaatggc tcacgcagga | 8760 |
| aaagataccg gaggcagcca atttttatc gtccatgagc ctcagccgca cttgaacggc | 8820 |
| gttcacaccg ttttcggaaa ggtcacatca ggccttgatg ccgtcacttc aatggagcag | 8880 |
| ggacaaggca tggaaaaagt cgaagtattt gatgcataat cagagagcgc aaaaaacagc | 8940 |
| ccgcttagcc gggctgtttt tttgtctgta acggtgttta ttttccaggt gcaacaggac | 9000 |
| ttgaggccga ttcttcgtcc acatcctgat aggaaataac gatgctaata aataaaataa | 9060 |
| ttgtgaaaaa atgacccttt atgtaaaata tattcaagtg aagagctaga tagagaacgc | 9120 |
| aatctgtaaa aaaggaaggg gcgtaagggg tgagcgtaaa aatcccatcg acggcagtcg | 9180 |
| gcgtaaaaat taatgactgg tataacgcga tacg | 9214 |

<210> SEQ ID NO 46
<211> LENGTH: 4450
<212> TYPE: DNA
<213> ORGANISM: Bacillus licheniformis

<400> SEQUENCE: 46

| | |
|---|---|
| catcggacag ctcttgcttg atatcttcaa aatgacgccg gctcatgtca tgtcaacttt | 60 |
| tgtcgtatct ggagcgatcc ttgacggatt cggcatttac gaccgtttta tcgaatttgc | 120 |
| cggtgccggg gctacagtcc cgattgtcag cttcggccac tctcttttgc acggcgcgat | 180 |
| gcaccaggct gagaaacatg gctttatcgg aatcggcatg gggatatttg aactgacatc | 240 |
| tgccggtata tctgccgcta tcttgttcgc ttttcttgtt gccgtgattt ttaaaccgaa | 300 |
| aggataaagg aaaatgccag caaaacgcaa ggtcattttg gtcacagacg gcgatatata | 360 |
| cgctgcaaaa gcaatcgaat atgcagcaag aaaaacgggt ggccgctgca tttcccaatc | 420 |
| ggcggggaat ccgagcgtta aaacaggacc ggagcttgta accatgatcc tgcaaacccc | 480 |
| tcatgatcct gtattcgtca tgtttgatga ttccggactt caaggtgaag gcccgggaga | 540 |
| gacagctatg aaatatgtag cgatgcatcc cgatatcgag gtgctcggag tcatcgccgt | 600 |
| cgcttcaaaa actcattatg cagagtggac gagagtcgat gtatcaatcg atgcagaagg | 660 |
| cgaactgaca gagtacggcg tcgataaaca cggggtcaaa gagttcgatg tcaaacgaat | 720 |
| gaatggtgat acagtctatt gccttgacca gctggatgtt ccgatcattg tcggaatcgg | 780 |
| tgatatcggt aagatgaaca gaaaagacga tgtggaaaaa ggttcgccga ttacaatgaa | 840 |
| agcggtcgag ctcatttag aaaggagcgg gtatcatgag tgctcaaaag caagagaaga | 900 |
| cgaacgtatt ccttgatcct tctaagaatg aagcgtattt caagaagcgg tcggcatgg | 960 |
| gagaaagctt tgaccttggc gtacggaagg tctttattct cggacatgaa gttcagcttt | 1020 |
| attatgtcaa cggattgtgc gacacacaat acatcattca cctgttaaga gaactggtgc | 1080 |
| atctgaatga taaagaaaaa gaatcgggcg aggtcgaaga catcgtcgaa acaggctttt | 1140 |
| tgaaccagca ggtttcaaaa gcggaaacgc ttgatgaagc tgtcgaccaa gtgttgtcag | 1200 |
| gactggttgc catcatcgtc gaagatgcgg gctttgcttt tatcatcgat gtcagaagct | 1260 |
| acccgggcag aacgccggaa gaacctgata cagaaaaagt cgtacgcggt gcaagggacg | 1320 |
| gactcgtcga gaacatcatc gtcaacacag ccctgattag acgccggatc agagatgagc | 1380 |
| gcttgcgcta caaaatgctt catatcggtg aacgctctaa aacagacatc tgcctctgct | 1440 |
| atttggaaga cgttgcagat cccgatcttg ttgaagtatt aaaaaagaa attgaagatg | 1500 |
| tgaagatcga cgggctgccg atgtcggata atcggtaga ggaattcctg gtcggccaag | 1560 |
| gctacaatcc gtttccgctt gtcaggttta cggaaagggc agacgtagcc gcaagccata | 1620 |

```
ttttagaggg gcatgtcatc gtgatcgtcg atacgtcgcc aagcgtcatc atcacaccga   1680
ccactttgtt tcaccatgtt cagcatgctg aggaatacag acagacgccg gctgttggga   1740
cgtttttaag gtgggtgcgg ttttccggta ttttggcctc cacctttttg ctgccgcttt   1800
ggctgctgtt tgtcattcat ccgtcgctct tgcctgataa tttatcgttt atcgggttga   1860
ataaagacac ccatattccg attatcatgc agattttcct ggcggatctc ggcgtcgaat   1920
ttttaagaat ggccgccatt catacgccga cggcgctttc gactgcaatg gcctgatcg   1980
ccgctgtatt gatcggcgat atcgcgatca atgtcggctt gttttctccc gaagtcattt   2040
tatacgtttc cctctcggca atcggagcct acacgacacc aagctacgag ctgagcctgg   2100
cgaataaaat ggtgaagctg tttatgctga tattggtggc gcttttttaaa gtggagggat   2160
ttgtcatcgg attaacgatc ttaactatag tgatgacttc gatcaggtca ttgcgaacgc   2220
cttacttatg gcctctcctc ccgttcaatg gaaaagcgtt ttggcatgtt ctcgtgcgca   2280
cgtccgttcc agggggaaaa gtcaggccga gcatcgttca tccgagaaac cgctccagac   2340
agccgtgaag ccggcattcg aagaggcttt tccccgggga aaagcctctt tttcaataat   2400
cgaattccgg tctttgagta ccgatgcctc tgtattcatt ggcagagatc gcgactgccc   2460
ggaggctgca gatgttgttc tgtcttctga tcggatagac gacatacagc atttcgcggc   2520
cgtacgggtc aatcgttgac gaatgaagga aaacctcagt tcctctccgc caaaatctcg   2580
tattcgccgg agctgtaata atctgccctt cataaggctc ataaattctc tgttcataat   2640
gcgcagccgg ctgataaggg gcgtatacat cttcaggtgc atagccggga gcggggtgt   2700
agggatagcg atttggatac atatgataac ctctttccca cttcgttttt tggttttcat   2760
ctttaagatt atattcaggt aaatgccat ttgtatgggc gaaatctca gcttttcggc   2820
tcttttttta ttgaatggac gttgtgtatg cctatttcta tcaagcgctg ttttctgtta   2880
ttctataatc aatagaatgg attagttgtt tagggaatca tttccttat aaatcaagaa   2940
aatttggaca aatggtggtt tagtttttaa acgaaatgt tataatacaa cataagaatc   3000
gcactatcat gaagccggaa gatgcatcgg gcagcaaccg gagcgcccct tgcacctttg   3060
tcgatagaga aagagggaat gacaattgtt tttacacggt actagcagac aaaatgaaag   3120
agggcacctc gaaatcggcg gtgtcgatgt tctatcattg gcagaaagat acggaacacc   3180
tctttatgta tacgatgtcg cgctgattag agagcgcgcc cgaaaattcc agaaggcatt   3240
caaggaagcc ggtttaaaag cgcaggtagc gtatgcaagc aaggcgtttt catcggttgc   3300
catgattcag cttgccgaac aagaggggct gtctctggat gtggtatcgg gaggagagct   3360
tttcactgcg atcaaagcag ggttcccagc tgagcggatt cattttcacg gaaacaataa   3420
gagccctgaa gaactagcca tggcgctgga gcatcaaatc ggctgcatcg tgctcgataa   3480
ctttcacgag atcgccatta cagaagatct ttgcaagcga tcaggacaaa ctgtagacgt   3540
tttgctcaga atcactccgg gagttgaagc gcacacgcac gattatatta cgacggggca   3600
ggaagattcc aaattcggtt ttgatctgca taatggacag gtcgaacaag ccatcgaaca   3660
agtcctccgc tcgtctgcgt ttaagctcct cggcgtgcac tgccacatcg gttcgcaaat   3720
ttttgatacg gcaggatttg tccttgcagc agacaagatt ttcgagaagc ttgcggaatg   3780
gcgggagact tactctttca ttccggaagt gctcaatctt ggcgggggct tcggcatccg   3840
ctatacaaaa gacgacagag cgcttgcagc tgatgtttat gttgaaaaaa tcatcgaggc   3900
ggtcaaagca aatgccgagc atttcggctt tgacatccct gagatttgga tcgaaccagg   3960
```

| | |
|---|---|
| ccggtctctc gtcggtgatg cggggactac gctgtacacg atcggttctc aaaaagaggt | 4020 |
| gccgggcatt cgcaaatatg tagccatcga cggcggcatg agcgataata tcaggccggc | 4080 |
| gctttatgag gcaaaatatg aagcagccgt cgccaacagg atgaacgatg cttgtcatga | 4140 |
| taccgcatca atcgcaggaa aatgctgcga aagcggagat atgctgattt gggatttgga | 4200 |
| aatccccgaa gttcgcgacg gagatgtgct cgccgttttc tgcaccggtg cgtacggcta | 4260 |
| cagcatggcc aacaactaca accgcattcc gcgcccggcc gtcgtctttg tcgaggacgg | 4320 |
| ggaagcgcag ctcgtcattc agagagagac gtatgaggat atcgtcaagc tggatctgcc | 4380 |
| gctgaaatcg aaagtcaaac aataaaaaaa tggagattcc ctaagagggg ggtctccatt | 4440 |
| tttaattcaa | 4450 |

<210> SEQ ID NO 47
<211> LENGTH: 57
<212> TYPE: DNA
<213> ORGANISM: Artificial Sequence
<220> FEATURE:
<223> OTHER INFORMATION: synthetic

<400> SEQUENCE: 47

| | |
|---|---|
| acagaatagt cttttaagta agtctactct gaatttttt aaaggagag ggtaaag | 57 |

<210> SEQ ID NO 48
<211> LENGTH: 87
<212> TYPE: DNA
<213> ORGANISM: Bacillus licheniformis

<400> SEQUENCE: 48

| | |
|---|---|
| atgaaacaac aaaaacggct ttacgcccga ttgctgacgc tgttatttgc gctcatcttc | 60 |
| ttgctgcctc attctgcagc tagcgca | 87 |

<210> SEQ ID NO 49
<211> LENGTH: 1452
<212> TYPE: DNA
<213> ORGANISM: Artificial Sequence
<220> FEATURE:
<223> OTHER INFORMATION: synthetic

<400> SEQUENCE: 49

| | |
|---|---|
| gcagcgacaa acggaacaat gatgcagtat ttcgagtggt atgtacctaa cgacggccag | 60 |
| caatggaaca gactgagaac agatgcccct tacttgtcat ctgttggtat tacagcagta | 120 |
| tggacaccgc cggcttataa gggcacgtct caagcgatg tggggtacgg cccgtacgat | 180 |
| ctgtatgatt taggcgagtt taatcaaaaa ggtacagtca gaacgaagta tggcacaaaa | 240 |
| ggagaactta aatctgctgt caacacgctg cattccaaatg gaatccaagt gtatggtgat | 300 |
| gtcgtgatga atcataaagc aggtgctgat tatacagaaa acgtaacggc ggtggaggtg | 360 |
| aatccgtcta atagatatca ggaaacgagc ggcgaatata atattcaggc atggacaggc | 420 |
| ttcaactttc cgggcagagg aacaacgtat tctaactgga atggcagtg gttccatttt | 480 |
| gatggaacgg attgggacca gagcagaagc ctctctagaa tcttcaaatt ccatggaaag | 540 |
| gcgtgggact ggccggtttc ttcagaaaac ggaaattatg actatctgat gtacgcggac | 600 |
| tatgattatg accatccgga tgtcgtgaat gaaatgaaaa agtgggcgt ctggtatgcc | 660 |
| aacgaagttg ggttagatgg atacagactt gacgcggtca acatattaa atttagcttt | 720 |
| ctcaaagact gggtggataa cgcaagagca gcgacggaa aagaaatgtt tacggttgc | 780 |
| gaatattggc aaaatgattt aggggccctg aataactacc tggcaaaggt aaattacaac | 840 |

-continued

```
caatctcttt tgatgcgcc gttgcattac aactttacg ctgcctcaac agggggtgga      900
gcgtacgata tgagaaatat tcttaataac acgttagtcg caagcaatcc gacaaaggct    960
gttacgttag ttgagaatca tgacacacag cctggacaat cactggaatc aacagtccaa   1020
ccgtggttta aaccgttagc ctacgcgttt attctcacga gaagcggagg ctatcctgcg   1080
gtattttatg gagatatgta cggtacaaaa ggaacgacaa catatgagat ccctgctctt   1140
aaatctaaaa tcgaaccttt gcttaaggct agaaaagact atgcttatgg aacacagaga   1200
gactatattg ataacccgga tgtcattggc tggacgagag aaggggactc aacgaaagcc   1260
aagagcggtc tggccacagt gattacagat gggccgggcg gttcaaaaag aatgtatgtt   1320
ggcacgagca atgcgggtga aatctggtat gatttgacag ggaatagaac agataaaatc   1380
acgattggaa gcgatggcta tgcaacattt cctgtcaatg ggggctcagt ttcagtatgg   1440
gtgcagcaat ga                                                      1452
```

<210> SEQ ID NO 50
<211> LENGTH: 34
<212> TYPE: DNA
<213> ORGANISM: Bacillus licheniformis

<400> SEQUENCE: 50

```
cggatttcct gaaggaaatc cgttttttta tttt                                 34
```

<210> SEQ ID NO 51
<211> LENGTH: 3019
<212> TYPE: DNA
<213> ORGANISM: Bacillus licheniformis

<400> SEQUENCE: 51

```
caagcacgaa aaacacttcc cggtgatcgg gaggtgtttt ttgttaaaaa gatcatgaca     60
tgcatagaac agcgaccggg ctaattgtat ataatattgt gaatttaaca aaaaatttac    120
aaaggagatg ataaaggcaa tgaccagggt gaaaaggatg agatttgctg atttgttgga   180
tttagaggcg gagtagatga aaccggccaa agtatcccta ctccaccgat tgctccagtg   240
cctgaagcaa tgtgttgatt gtaacacagt aaatcgtttt acagcaataa acattttgt    300
gaatatttta ttgatttcgg ctgtgatctc attcccatat tctgctgcgg cccatggcgc   360
aacacagtcc ggcgatcaat attcaagctt tgaagaattg gagcggaatg aagatccagc   420
ttcttaccga attacggaga gaacgcaag agtgccgatg ctcatcatgg ccatccatgg    480
aggcggcatc gaacccggaa cgagcgaaat cgccaatgaa gtgtccaaaa actattccct   540
gtacttgttt gaagggctga atcatcagg caatacggac cttcacatta caagcacgcg    600
tttgacgag ccagcggcgc tcgcaattac tgcaagccac cagtatgtca tgtcgctcca    660
cggctattac agtgaagacc gcgatattaa agtaggcggc acagaccgcg ctaaaatcag   720
aatattggtt gatgagctga accgctcggg gttgccgct gaaatgctgg ggacagatga    780
caagtatgcc ggaacccatc cgaataacat cgccaacaag tcgctttccg ggctgagcat   840
tcagcttgaa atgagcacgg gtttccgcaa atctttattc gaccggttta cactaaaaga   900
cagggcggcg acgcaaaacg aaacgtttta ccgatttaca aagctgctga cagatttttat   960
tcatgaaaac tatgaagaag acggagggga tttcccctct gcaaaaataa acaccccct   1020
tcaagtgaaa aaggaggtgt tcggcggtt gtgttaaccg ttggactctg aggtgccgcc   1080
gccggtgaat acgaaaacga tggcgttcca cagagacaca aagaagtcga tcagttttg    1140
```

```
aagaaagttt tgtccttctt cagaatccaa gaatttcgtg attttatcct ttgctttgtc    1200
aagctggtct ccaacctggt tccagtcgat attaatattt ttcatgttat taaataaaga    1260
tataagagag tttttctgat cttctgtgag tgtcacgcca agttcggaag cagccgaatc    1320
aatcgttttc tccaattcct cttttgactc gggaactccg ttttcgaga tttcttcctt     1380 gactttggcc atcagcgctg acgcgttttc actgccgatt ttctcgccaa gctctgaagt    1440
ggtgacaagc tcttcattcg cgaccttttt cacatcttcg gaattttttt cgcccgaagt    1500
cgtttcatac gctttcatca atccggttaa agcggctgtg cctgacactt caaacggagc    1560
ggtgacatag actttggcgt cttttacacc ggccgtcatc agcgcgttca aatacatctc    1620
atctgtaatt ctgctgatat tgtgtgtctg aacttccaaa ccggtgcctt ttttcgctac    1680
ggtaattgaa gaagaagaaa tcgctcttgt tccgatttgt gctttcggta tataatcccc    1740
taaatattta tgctcctcat catttgtcac ctcgatgatg gtcgcatttt caggcgcatt    1800
catttctttt aatactttt gtctgtcctg gcttgacaag tctttcccca gcgtgacgat     1860
gacatcaccc actgcggcgt cagcgaagct gacctgcggg aaaatgagca gacacaatgc    1920
tgtaaagatt cctagtatcg attttttcaa gctcaatgcc ctccttaaaa atgcaggctt    1980
caggcagaat tgctgtactt ttaaagaagc ctgccgaac  ggaataatg cgttccgaaa     2040 tatagacgga tgaaagatga gtgaggtttc aaagaaaaaa agagagaatt ttctcttcaa    2100
gtcaaatgcc ctcccggcat cgtatctcgc cgctctttta tcattcatga ttttcacagg    2160
cgattcaacc tttttttaaa atttttaca aaaacgatac aagagcggcg tttatttcgg     2220
tcgattggct ctctgcttct tcaatatgat ataatgaccc ttgtgaaatg aaaggagaga    2280
atcaagatgg ctaaaaaagg atacatacaa ctgacaaacg gcaaaaaaat cgagtttgaa    2340
ctatatccgg atgcggcgcc gggaactgtc gccaactttg aaaaacttgc aaacgaaggg    2400
ttctatgacg ggctgaagtt ccaccgcgtc atcccgggct tcgtcagcca gggaggctgc    2460
ccgcacggca ccggaacagg cggacctgga tatacgatta aatgcgagac agaagggaat    2520
ccgcacaaac acgaagccgg ttctctctca atggctcacg caggaaaaga taccggaggc    2580
agccaatttt ttatcgtcca tgagcctcag ccgcacttga acggcgttca caccgttttc    2640
ggaaaggtca catcaggcct tgatgccgtc acttcaatgg agcagggaca aggcatggaa    2700
aaagtcgaag tatttgatgc ataatcagag agcgcaaaaa acagcccgct tagccgggct    2760 gttttttgt ctgtaacggt gtttattttc caggtgcaac aggacttgag gccgattctt      2820
cgtccacatc ctgataggaa ataacgatgc taataaataa aataattgtg aaaaaatgac     2880
cctttatgta aaatatattc aagtgaagag ctagatagag aacgcaatct gtaaaaaagg     2940
aaggggcgta aggggtgagc gtaaaaatcc catcgacggc agtcggcgta aaaattaatg    3000
actggtataa cgcgatacg                                                 3019
```

<210> SEQ ID NO 52
<211> LENGTH: 20
<212> TYPE: DNA
<213> ORGANISM: Artificial Sequence
<220> FEATURE:
<223> OTHER INFORMATION: synthetic

<400> SEQUENCE: 52
gatttgggat ttggaaatcc                                                  20

<210> SEQ ID NO 53
<211> LENGTH: 18

```
<212> TYPE: DNA
<213> ORGANISM: Artificial Sequence
<220> FEATURE:
<223> OTHER INFORMATION: synthetic

<400> SEQUENCE: 53
caacacattg cttcaggc                                                       18

<210> SEQ ID NO 54
<211> LENGTH: 20
<212> TYPE: DNA
<213> ORGANISM: Artificial Sequence
<220> FEATURE:
<223> OTHER INFORMATION: synthetic

<400> SEQUENCE: 54
tcagagagag acgtatgagg                                                     20

<210> SEQ ID NO 55
<211> LENGTH: 20
<212> TYPE: DNA
<213> ORGANISM: Artificial Sequence
<220> FEATURE:
<223> OTHER INFORMATION: synthetic

<400> SEQUENCE: 55
gcatggacag gcttcaactt                                                     20

<210> SEQ ID NO 56
<211> LENGTH: 20
<212> TYPE: DNA
<213> ORGANISM: Artificial Sequence
<220> FEATURE:
<223> OTHER INFORMATION: synthetic

<400> SEQUENCE: 56
ggatgtcatt ggctggacga                                                     20

<210> SEQ ID NO 57
<211> LENGTH: 20
<212> TYPE: DNA
<213> ORGANISM: Artificial Sequence
<220> FEATURE:
<223> OTHER INFORMATION: synthetic

<400> SEQUENCE: 57
tctactccgc ctctaaatcc                                                     20

<210> SEQ ID NO 58
<211> LENGTH: 91
<212> TYPE: DNA
<213> ORGANISM: Artificial Sequence
<220> FEATURE:
<223> OTHER INFORMATION: synthetic

<400> SEQUENCE: 58
gctgataaac agctgacatc aactaaaagc ttcattaaat actttgaaaa aagttgttga         60
cttaaaagaa gctaaatgtt atagtaattg t                                        91

<210> SEQ ID NO 59
<211> LENGTH: 91
<212> TYPE: DNA
<213> ORGANISM: Artificial Sequence
<220> FEATURE:
<223> OTHER INFORMATION: synthetic
```

<400> SEQUENCE: 59
gctgataaac agctgacatc aactaaaagt ttcattaaat actttgaaaa aagttgttga    60
cttaaaagaa gctaaatgtt atagtaataa a                                   91

<210> SEQ ID NO 60
<211> LENGTH: 91
<212> TYPE: DNA
<213> ORGANISM: Artificial Sequence
<220> FEATURE:
<223> OTHER INFORMATION: synthetic

<400> SEQUENCE: 60
cgactatttg tcgactgtag ttgattttcg aagtaattta tgaaactttt ttcaacaact    60 gaatttctt cgatttacaa tatcattatt t                                    91

<210> SEQ ID NO 61
<211> LENGTH: 91
<212> TYPE: DNA
<213> ORGANISM: Artificial Sequence
<220> FEATURE:
<223> OTHER INFORMATION: synthetic

<400> SEQUENCE: 61
cgactatttg tcgactgtag ttgattttca aagtaattta tgaaactttt ttcaacaact    60 gaatttctt cgatttacaa tatcattaac a                                    91

<210> SEQ ID NO 62
<211> LENGTH: 91
<212> TYPE: DNA
<213> ORGANISM: Artificial Sequence
<220> FEATURE:
<223> OTHER INFORMATION: synthetic

<400> SEQUENCE: 62
cgactatttg tcgactgtag ttgattttcg aagtaattta tgaaactttt ttcaacaact    60 gaatttctt cgatttacaa tatcattaac a                                    91

<210> SEQ ID NO 63
<211> LENGTH: 91
<212> TYPE: DNA
<213> ORGANISM: Artificial Sequence
<220> FEATURE:
<223> OTHER INFORMATION: synthetic

<400> SEQUENCE: 63
cgactatttg tcgactgtag ttgattttcg aagtaattta tgaaactttt ttcaacaact    60 gaatttctt cgatttacaa tatcattatt t                                    91

<210> SEQ ID NO 64
<211> LENGTH: 100
<212> TYPE: DNA
<213> ORGANISM: Bacillus licheniformis

<400> SEQUENCE: 64
gcttttcttt tggaagaaaa tatagggaaa atggtacttg ttaaaaattc ggaatattta    60
tacaatatca tatgtttcac attgaaaggg gaggagaatc                         100

<210> SEQ ID NO 65
<211> LENGTH: 100
<212> TYPE: DNA
<213> ORGANISM: Artificial Sequence
<220> FEATURE:
<223> OTHER INFORMATION: synthetic

<400> SEQUENCE: 65
gcttttcttt tggaagaaaa tagggaaa atggtacttg ttaaaaattc ggaatattta    60
tacaatatca ttgttttcac attgaaaggg gaggagaatc                      100

<210> SEQ ID NO 66
<211> LENGTH: 132
<212> TYPE: DNA
<213> ORGANISM: Artificial Sequence
<220> FEATURE:
<223> OTHER INFORMATION: syntehtic

<400> SEQUENCE: 66
gcttttcttt tggaagaaaa tagggaaa atggtacttg ttaaaaattc ggaatattta    60
tacaatatca tatgacagaa tagtctttta agtaagtcta ctctgaattt ttttaaaagg  120
agagggtaaa ga                                                    132

<210> SEQ ID NO 67
<211> LENGTH: 132
<212> TYPE: DNA
<213> ORGANISM: Artificial Sequence
<220> FEATURE:
<223> OTHER INFORMATION: synthetic

<400> SEQUENCE: 67
gcttttcttt tggaagaaaa tagggaaa atggtacttg ttaaaaattc ggaatattta    60
tacaatatca ttgtacagaa tagtctttta agtaagtcta ctctgaattt ttttaaaagg  120
agagggtaaa ga                                                    132

<210> SEQ ID NO 68
<211> LENGTH: 2475
<212> TYPE: DNA
<213> ORGANISM: B. deramificans

<400> SEQUENCE: 68
gcagctaaac ccgctgtaag caacgcttat ttagatgctt caaaccaggt gctggttaaa    60
cttagccagc cgttaactct tggggaaggc gcaagcggct ttacggttca tgacgacaca   120
gcaaataagg atattccagt gacatctgtg aaggatgcaa gtcttggtca agatgtaacc   180
gctgttttgg caggtacctt ccaacatatt tttggaggtt ccgattgggc acctgataat   240
cacagtactt tattaaaaaa ggtgactaac aatctctatc aattctcagg agatcttcct   300
gaaggaaact accaatataa agtggcttta atgatagct ggaataatcc gagttaccca   360
tctgacaaca ttaatttaac agtccctgcc ggcggtgcac acgtcacttt ttcgtatatt   420
ccgtccactc atgcagtcta tgacacaatt aataatccta tgcggatttt acaagtagaa   480
agcggggtta aaacggatct cgtgacggtt actctagggg aagatccaga tgtgagccat   540
actctgtcca ttcaaacaga tggctatcag gcaaagcagg tgatacctcg taatgtgctt   600
aattcatcac agtactacta ttcaggagat gatcttggga ataccctata cagaaagca   660 acaacccttta aagtctgggc accaacttct actcaagtaa atgttcttct ttatgacagt   720
gcaacgggtt ctgtaacaaa aatcgtacct atgacggcat cgggccatgg tgtgtgggaa   780
gcaacggtta atcaaaacct tgaaaattg tattacatgt atgaggtaac aggccaaggc   840
tctacccgaa cggctgttga tcctatgca actgcgattg caccaaatgg aacgagaggc   900

```
atgattgtgg acctggctaa acagatcct gctggctgga acagtgataa acatattacg      960
ccaaagaata tagaagatga ggtcatctat gaaatggatg tccgtgactt ttccattgac     1020
cctaattcgg gtatgaaaaa taagggaag tatttggctc ttacagaaaa aggaacaaag     1080
ggccctgaca acgtaaagac ggggatagat tccttaaaac aacttgggat tactcatgtt    1140
cagcttatgc ctgttttcgc atctaacagt gtcgatgaaa ctgatccaac ccaagataat    1200
tggggttatg accctcgcaa ctatgatgtt cctgaagggc agtatgctac aaatgcgaat    1260
ggtaatgctc gtataaaaga gtttaaggaa atggttcttt cactccatcg tgaacacatt    1320
ggggttaaca tggatgttgt ctataatcat acctttgcca cgcaaatctc tgacttcgat    1380
aaaattgtac agaatatta ttaccgtacg gatgatgcag gtaattatac caacggatca     1440
ggtactggaa atgaaattgc agccgaaagg ccaatggttc aaaatttat tattgattcc     1500 cttaagtatt gggtcaatga gtatcatatt gacggcttcc gttttgactt aatggcgctg    1560
cttggaaaag acacgatgtc caaagctgcc tcggagcttc atgctattaa tccaggaatt    1620
gcactttacg gtgagccatg gacgggtgga acctctgcac tgccagatga tcagcttctg    1680
acaaaaggag ctcaaaaagg catgggagta gcggtgttta atgacaattt acgaaacgcg    1740
ttggacggca atgtctttga ttcttccgct caaggttttg cgacaggtgc aacaggctta    1800
actgatgcaa ttaagaatgg cgttgagggg agtattaatg actttacctc ttcaccaggt    1860
gagacaatta actatgtcac aagtcatgat aactacaccc tttgggacaa aatagcccta    1920
agcaatccta atgattccga agcggatcgg attaaaatgg atgaactcgc acaagcagtt    1980
gttatgacct cacaaggcgt tccattcatg caaggcgggg aagaaatgct tcgtacaaaa    2040
ggcggcaacg acaatagtta taatgcaggc gatgcggtca atgagtttga ttggagcagg    2100
aaagctcaat atccagatgt tttcaactat tatagcgggc taatccacct tcgtcttgat    2160
cacccagcct tccgcatgac gacagctaat gaaatcaata gccacctcca attcctaaat    2220
agtccagaga acacagtggc ctatgaatta actgatcatg ttaataaaga caaatgggga    2280
aatatcattg ttgtttataa cccaaataaa actgtagcaa ccatcaattt gccgagcggg    2340
aaatgggcaa tcaatgctac gagcggtaag gtaggagaat ccacccttgg tcaagcagag    2400
ggaagtgtcc aagtaccagg tatatctatg atgatccttc atcaagaggt aagcccagac    2460
cacggtaaaa agtaa                                                     2475
```

<210> SEQ ID NO 69
<211> LENGTH: 21
<212> TYPE: DNA
<213> ORGANISM: Artificial Sequence
<220> FEATURE:
<223> OTHER INFORMATION: synthetic

<400> SEQUENCE: 69
ctacagcatg gccaacaact a                                                21

<210> SEQ ID NO 70
<211> LENGTH: 24
<212> TYPE: DNA
<213> ORGANISM: Artificial Sequence
<220> FEATURE:
<223> OTHER INFORMATION: synthetic

<400> SEQUENCE: 70
gtcatgatct ttttaacaaa aaac                                             24

<210> SEQ ID NO 71
<211> LENGTH: 22
<212> TYPE: DNA
<213> ORGANISM: Artificial Sequence
<220> FEATURE:
<223> OTHER INFORMATION: synthetic

<400> SEQUENCE: 71
gattgctgac gctgttattt gc					22

<210> SEQ ID NO 72
<211> LENGTH: 20
<212> TYPE: DNA
<213> ORGANISM: Artificial Sequence
<220> FEATURE:
<223> OTHER INFORMATION: synthetic

<400> SEQUENCE: 72
gtagaagttg gtgcccagac					20

<210> SEQ ID NO 73
<211> LENGTH: 25
<212> TYPE: DNA
<213> ORGANISM: Artificial Sequence
<220> FEATURE:
<223> OTHER INFORMATION: synthetic

<400> SEQUENCE: 73
ggaataccta tacacagaaa gcaac					25

<210> SEQ ID NO 74
<211> LENGTH: 24
<212> TYPE: DNA
<213> ORGANISM: Artificial Sequence
<220> FEATURE:
<223> OTHER INFORMATION: synthetic

<400> SEQUENCE: 74
cattcgcatt tgtagcatac tgcc					24

<210> SEQ ID NO 75
<211> LENGTH: 20
<212> TYPE: DNA
<213> ORGANISM: Artificial Sequence
<220> FEATURE:
<223> OTHER INFORMATION: synthetic

<400> SEQUENCE: 75
cacgcaaatc tctgacttcg					20

<210> SEQ ID NO 76
<211> LENGTH: 19
<212> TYPE: DNA
<213> ORGANISM: Artificial Sequence
<220> FEATURE:
<223> OTHER INFORMATION: synthetic

<400> SEQUENCE: 76
caagcagcgc cattaagtc					19

<210> SEQ ID NO 77
<211> LENGTH: 21
<212> TYPE: DNA
<213> ORGANISM: Artificial Sequence
<220> FEATURE:
<223> OTHER INFORMATION: synthetic

<400> SEQUENCE: 77

```
gcaacgacaa tagttataat g                                              21
```

<210> SEQ ID NO 78
<211> LENGTH: 10178
<212> TYPE: DNA
<213> ORGANISM: Artificial Sequence
<220> FEATURE:
<223> OTHER INFORMATION: synthetic

<400> SEQUENCE: 78

```
catcggacag ctcttgcttg atatcttcaa aatgacgccg gctcatgtca tgtcaacttt     60
tgtcgtatct ggagcgatcc ttgacggatt cggcatttac gaccgtttta tcgaatttgc   120
cggtgccggg gctacagtcc cgattgtcag cttcggccac tctcttttgc acggcgcgat   180
gcaccaggct gagaaacatg gctttatcgg aatcggcatg gggatatttg aactgacatc   240
tgccggtata tctgccgcta tcttgttcgc ttttcttgtt gccgtgattt ttaaaccgaa   300
aggataaagg aaaatgccag caaaacgcaa ggtcattttg gtcacagacg gcgatatata   360
cgctgcaaaa gcaatcgaat atgcagcaag aaaaacgggt ggccgctgca tttcccaatc   420
ggcggggaat ccgagcgtta aaacaggacc ggagcttgta accatgatcc tgcaaacccc   480
tcatgatcct gtattcgtca tgtttgatga ttccggactt caaggtgaag gcccgggaga   540
gacagctatg aaatatgtag cgatgcatcc cgatatcgag gtgctcggag tcatcgccgt   600
cgcttcaaaa actcattatg cagagtggac gagagtcgat gtatcaatcg atgcagaagg   660
cgaactgaca gagtacggcg tcgataaaca cggggtcaaa gagttcgatg tcaaacgaat   720
gaatggtgat acagtctatt gccttgacca gctggatgtt ccgatcattg tcggaatcgg   780
tgatatcggt aagatgaaca gaaaagacga tgtggaaaaa ggttcgccga ttacaatgaa   840
agcggtcgag ctcatttttag aaaggagcgg gtatcatgag tgctcaaaag caagagaaga   900
cgaacgtatt ccttgatcct tctaagaatg aagcgtattt caagaagcgg tcggcatgg    960
gagaaagctt tgaccttggc gtacggaagg tctttattct cggacatgaa gttcagcttt  1020
attatgtcaa cggattgtgc gacacacaat acatcattca cctgttaaga gaactggtgc  1080
atctgaatga taaagaaaaa gaatcgggcg aggtcgaaga catcgtcgaa acaggctttt  1140
tgaaccagca ggtttcaaaa gcggaaacgc ttgatgaagc tgtcgaccaa gtgttgtcag  1200
gactggttgc catcatcgtc gaagatgcgg gctttgcttt tatcatcgat gtcagaagct  1260
acccgggcag aacgccggaa gaacctgata cagaaaaagt cgtacgcggt gcaagggacg  1320
gactcgtcga gaacatcatc gtcaacacag ccctgattag acgccggatc agagatgagc  1380
gcttgcgcta caaatgctt catatcggtg aacgctctaa aacagacatc tgcctctgct  1440
atttggaaga cgttgcagat cccgatcttg ttgaagtatt aaaaaaagaa attgaagatg  1500
tgaagatcga cgggctgccg atgtcggata aatcggtaga ggaattcctg gtcggccaag  1560
gctacaatcc gtttccgctt gtcaggttta cggaaagggc agacgtagcc gcaagccata  1620
ttttagaggg gcatgtcatc gtgatcgtcg atacgtcgcc aagcgtcatc atcacaccga  1680
ccactttgtt tcaccatgtt cagcatgctg aggaatacag acagacgccg gctgttggga  1740
cgttttttaag gtgggtgcgg ttttttcggta ttttggcctc cacctttttg ctgccgcttt  1800
ggctgctgtt tgtcattcat ccgtcgctct tgcctgataa tttatcgttt atcgggttga  1860
ataaagacac ccatattccg attatcatgc agattttcct ggcggatctc ggcgtcgaat  1920
ttttaagaat ggccgccatt catacgccga cggcgctttc gactgcaatg ggcctgatcg  1980
```

```
ccgctgtatt gatcggcgat atcgcgatca atgtcggctt gttttctccc gaagtcattt      2040
tatacgtttc cctctcggca atcggagcct acacgacacc aagctacgag ctgagcctgg      2100
cgaataaaat ggtgaagctg tttatgctga tattggtggc gcttttttaaa gtggagggat     2160 ttgtcatcgg attaacgatc ttaactatag tgatgacttc gatcaggtca ttgcgaacgc      2220
cttacttatg gcctctcctc ccgttcaatg gaaaagcgtt ttggcatgtt ctcgtgcgca      2280
cgtccgttcc aggggaaaaa gtcaggccga gcatcgttca tccgagaaac cgctccagac      2340
agccgtgaag ccggcattcg aagaggcttt tccccgggga aaagcctctt tttcaataat      2400
cgaattccgg tctttgagta ccgatgcctc tgtattcatt ggcagagatc gcgactgccc      2460
ggaggctgca gatgttgttc tgtcttctga tcggatagac gacatacagc atttcgcggc      2520
cgtacgggtc aatcgttgac gaatgaagga aaacctcagt tcctctccgc caaaatctcg      2580
tattcgccgg agctgtaata atctgccctt cataaggctc ataaattctc tgttcataat      2640
gcgcagccgc ctgataaggg gcgtatacat cttcaggtgc atagccggga gcggggtgt       2700 agggatagcg atttggatac atatgataac ctctttccca cttcgttttt tggttttcat      2760
ctttaagatt atattcaggt aaatgcctat ttgtatgggc gaaaatctca gcttttcggc      2820
tcttttttta ttgaatggac gttgtgtatg cctatttcta tcaagcgctg ttttctgtta      2880
ttctataatc aatagaatgg attagttgtt tagggaatca tttcctttat aaatcaagaa      2940
aatttggaca aatggtggtt tagtttttaa aacgaaatgt tataatacaa cataagaatc      3000
gcactatcat gaagccggaa gatgcatcgg gcagcaaccg gagcgcccct tgcacctttg      3060
tcgatagaga aagagggaat gacaattgtt tttacacggt actagcagac aaaatgaaag      3120
agggcacctc gaaatcggcg gtgtcgatgt tctatcattg gcagaaagat acggaacacc      3180
tctttatgta tacgatgtcg cgctgattag agagcgcgcc cgaaaattcc agaaggcatt      3240
caaggaagcc ggtttaaaag cgcaggtagc gtatgcaagc aaggcgtttt catcggttgc      3300
catgattcag cttgccgaac aagaggggct gtctctggat gtggtatcgg gaggagagct      3360
tttcactgcg atcaaagcag ggttcccagc tgagcggatt cattttcacg gaaacaataa      3420
gagccctgaa gaactagcca tggcgctgga gcatcaaatc ggctgcatcg tgctcgataa      3480 cttcacgag atcgccatta cagaagatct ttgcaagcga tcaggacaaa ctgtagacgt      3540
tttgctcaga atcactccgg gagttgaagc gcacacgcac gattatatta cgacggggca      3600
ggaagattcc aaattcggtt ttgatctgca taatggacag gtcgaacaag ccatcgaaca      3660
agtcctccgc tcgtctgcgt ttaagctcct cggcgtgcac tgccacatcg gttcgcaaat      3720
ttttgatacg gcaggatttg tccttgcagc agacaagatt ttcgagaagc ttgcggaatg      3780
gcgggagact tactctttca ttccggaagt gctcaatctt ggcgggggct tcggcatccg      3840
ctatacaaaa gacgacgagc cgcttgcagc tgatgtttat gttgaaaaaa tcatcgaggc      3900
ggtcaaagca aatgccgagc atttcggctt tgacatccct gagatttgga tcgaaccagg      3960
ccggtctctc gtcggtgatg cggggactac gctgtacacg atcggttctc aaaaagaggt      4020
gccgggcatt cgcaaatatg tagccatcga cggcggcatg agcgataata tcaggccggc      4080
gctttatgag gcaaaatatg aagcagccgt cgccaacagg atgaacgatg cttgtcatga      4140
taccgcatca atcgcaggaa aatgctgcga aagcggagat atgctgattt gggatttgga      4200
aatccccgaa gttcgcgacg gagatgtgct cgccgttttc tgcaccggtg cgtacggcta      4260
cagcatggcc aacaactaca accgcattcc gcgcccggcc gtcgtctttg tcgaggacgg      4320
```

```
ggaagcgcag ctcgtcattc agagagagac gtatgaggat atcgtcaagc tggatctgcc    4380
gctgaaatcg aaagtcaaac aataaaaaaa tggagattcc ctaagagggg ggtctccatt    4440
tttaattcag cttttctttt ggaagaaaat atagggaaaa tggtacttgt taaaaattcg    4500
gaatatttat acaatatcat atgtttcaca ttgaaagggg aggagaatca tgaaacaaca    4560
aaaacggctt tacgcccgat tgctgacgct gttatttgcg ctcatcttct tgctgcctca    4620
ttctgcagct tcagcagcag ctaaacccgc tgtaagcaac gcttatttag atgcttcaaa    4680
ccaggtgctg gttaaactta gccagccgtt aactcttggg gaaggcgcaa gcggctttac    4740
ggttcatgac gacacagcaa ataaggatat tccagtgaca tctgtgaagg atgcaagtct    4800
tggtcaagat gtaaccgctg ttttggcagg taccttccaa catattttg gaggttccga    4860 ttgggcacct gataatcaca gtactttatt aaaaaaggtg actaacaatc tctatcaatt    4920
ctcaggagat cttcctgaag gaaactacca atataaagtg gctttaaatg atagctggaa    4980
taatccgagt tacccatctg acaacattaa tttaacagtc cctgccggcg gtgcacacgt    5040 cacttttttcg tatattccgt ccactcatgc agtctatgac acaattaata atcctaatgc    5100
ggatttacaa gtagaaagcg gggttaaaac ggatctcgtg acggttactc taggggaaga    5160
tccagatgtg agccatactc tgtccattca aacagatggc tatcaggcaa agcaggtgat    5220
acctcgtaac gtgcttaatt catcacagta ctactattca ggagatgatc ttgggaatac    5280
ctatacacag aaagcaacaa cctttaaagt ctgggcacca acttctactc aagtaaatgt    5340
tcttctttat gacagtgcaa cgggttctgt aacaaaaatc gtacctatga cggcatcggg    5400
ccatggtgtg tgggaagcaa cggttaatca aaaccttgaa aattggtatt acatgtatga    5460
ggtaacaggc caaggctcta cccgaacggc tgttgatcct tatgcaactg cgattgcacc    5520
aaatggaacg agaggcatga ttgtggacct ggctaaaaca gatcctgctg ctggaacag    5580 tgataaacat attacgccaa agaatataga agatgaggtc atctatgaaa tggatgtccg    5640 tgactttttcc attgacccta attcgggtat gaaaaataaa gggaagtatt tggctcttac    5700
agaaaaagga acaaagggcc ctgacaacgt aaagacgggg atagattcct taaaacaact    5760
tgggattact catgttcagc ttatgcctgt tttcgcatct aacagtgtcg atgaaactga    5820
tccaacccaa gataattggg gttatgaccc tcgcaactat gatgttcctg aagggcagta    5880
tgctacaaat gcgaatggta atgctcgtat aaaagagttt aaggaaatgg ttctttcact    5940
ccatcgtgaa cacattgggg ttaacatgga tgttgtctat aatcatacct tgccacgca    6000 aatctctgac ttcgataaaa ttgtaccaga atattattac cgtacggatg atgcaggtaa    6060
ttataccaac ggatcaggta ctggaaatga aattgcagcc gaaaggccaa tggttcaaaa    6120
atttattatt gattccctta agtattgggt caatgagtat catattgacg gcttccgttt    6180
tgacttaatg gcgctgcttg gaaaagacac gatgtccaaa gctgcctcgg agcttcatgc    6240
tattaatcca ggaattgcac tttacggtga gccatggacg ggtggaacct ctgcactgcc    6300
agatgatcag cttctgacaa aaggagctca aaaaggcatg gagtagcgg tgtttaatga    6360 caatttacga aacgcgttgg acggcaatgt cttttgattct tccgctcaag gttttgcgac    6420
aggtgcaaca ggcttaactg atgcaattaa gaatggcgtt gagggagta ttaatgactt    6480 tacctcttca ccaggtgaga caattaacta tgtcacaagt catgataact acacccttg    6540 ggacaaaata gccctaagca atcctaatga ttccgaagcg atcggatta aaatggatga    6600 actcgcacaa gcagttgtta tgacctcaca aggcgttcca ttcatgcaag cggggaaga    6660 aatgcttcgt acaaaaggcg gcaacgacaa tagttataat gcaggcgatg cggtcaatga    6720
```

```
gtttgattgg agcaggaaag ctcaatatcc agatgttttc aactattata gcgggctaat    6780
ccaccttcgt cttgatcacc cagccttccg catgacgaca gctaatgaaa tcaatagcca    6840
cctccaattc ctaaatagtc cagagaacac agtggcctat gaattaactg atcatgttaa    6900
taaagacaaa tggggaaata tcattgttgt ttataaccca aataaaactg tagcaaccat    6960
caatttgccg agcgggaaat gggcaatcaa tgctacgagc ggtaaggtag gagaatccac    7020
ccttggtcaa gcagagggaa gtgtccaagt accaggtata tctatgatga tccttcatca    7080
agaggtaagc ccagaccacg gtaaaaagta aaagagcaga gaggacggat ttcctgaagg    7140
aaatccgttt ttttattttc aagcacgaaa aacacttccc ggtgatcggg aggtgttttt    7200
tgttaaaaag atcatgacat gcatagaaca gcgaccgggc taattgtata taatattgtg    7260
aatttaacaa aaaatttaca aaggagatga taaaggcaat gaccagggtg aaaaggatga    7320
gatttgctga tttgttggat ttagaggcgg agtagatgaa accggccaaa gtatccctac    7380
tccaccgatt gctccagtgc ctgaagcaat gtgttgattg taacacagta aatcgtttta    7440
cagcaataaa cattttttgtg aatattttat tgatttcggc tgtgatctca ttcccatatt    7500
ctgctgcggc ccatggcgca acacagtccg gcgatcaata ttcaagcttt gaagaattgg    7560
agcggaatga agatccagct tcttaccgaa ttacggagaa gaacgcaaga gtgccgatgc    7620
tcatcatggc catccatgga ggcggcatcg aacccggaac gagcgaaatc gccaatgaag    7680
tgtccaaaaa ctattccctg tacttgtttg aagggctgaa atcatcaggc aatacggacc    7740
ttcacattac aagcacgcgt tttgacgagc cagcggcgct cgcaattact gcaagccacc    7800
agtatgtcat gtcgctccac ggctattaca gtgaagaccg cgatattaaa gtaggcggca    7860
cagaccgcgc taaaatcaga atattggttg atgagctgaa ccgctcgggg tttgccgctg    7920
aaatgctggg gacagatgac aagtatgccg gaacccatcc gaataacatc gccaacaagt    7980
cgctttccgg gctgagcatt cagcttgaaa tgagcacggg tttccgcaaa tctttattcg    8040
accggtttac actaaaagac agggcggcga cgcaaaacga aacgttttac cgatttacaa    8100
agctgctgac agattttatt catgaaaact atgaagaaga cggaggggat ttcccctctg    8160
caaaaataaa acacccccctt caagtgaaaa aggaggtgtt tcggcggttg tgttaaccgt    8220
tggactctga ggtgccgccg ccggtgaata cggaaacgat ggcgttccac agagacacaa    8280
agaagtcgat cagttttttga agaaagtttt gtccttcttc agaatccaag aatttcgtga    8340
ttttatcctt tgctttgtca agctggtctc caacctggtt ccagtcgata ttaatatttt    8400
tcatgttatt aaataaagat ataagagagt ttttctgatc ttctgtgagt gtcacgccaa    8460
gttcggaagc agccgaatca atcgtttttct ccaattcctc tttttgactcg ggaactccgt    8520 ttttcgagat ttcttccttg actttggcca tcagcgctga cgcgttttca ctgccgattt    8580
tctcgccaag ctctgaagtg gtgacaagct cttcattcgc gaccttttttc acatcttcgg    8640 aaattttttc gcccgaagtc gtttcatacg cttttcatcaa tccggttaaa gcggctgtgc    8700
ctgacacttc aaacggagcg gtgacataga cttttggcgtc ttttacaccg gccgtcatca    8760
gcgcgttcaa atacatctca tctgtaattc tgctgatatt gtgtgtctga acttccaaac    8820
cggtgccttt tttcgctacg gtaattgaag aagaagaaat cgctcttgtt ccgatttgtg    8880
ctttcggtat ataatcccct aaatatttat gctcctcatc atttgtcacc tcgatgatgg    8940 tcgcatttttc aggcgcattc atttcttttta atacttttttg tctgtcctgg cttgacaagt    9000
ctttccccag cgtgacgatg acatcaccca ctgcggcgtc agcgaagctg acctgcggga    9060
```

-continued

```
aaatgagcag acacaatgct gtaaagattc ctagtatcga ttttttcaag ctcaatgccc    9120
tccttaaaaa tgcaggcttc aggcagaatt gctgtacttt taaagaagcc tgccggaacg    9180
gaaataatgc gttccgaaat atagacggat gaaagatgag tgaggtttca agaaaaaaa     9240
gagagaattt tctcttcaag tcaaatgccc tcccggcatc gtatctcgcc gctcttttat    9300
cattcatgat tttcacaggc gattcaacct tttttaaaa  ttttttacaa aaacgataca    9360
agagcggcgt ttatttcggt cgattggctc tctgcttctt caatatgata taatgaccct    9420
tgtgaaatga aaggagagaa tcaagatggc taaaaagga  tacatacaac tgacaaacgg    9480
caaaaaaatc gagtttgaac tatatccgga tgcggcgccg ggaactgtcg ccaactttga    9540
aaaacttgca aacgaagggt tctatgacgg gctgaagttc caccgcgtca tcccgggctt    9600
cgtcagccag ggaggctgcc cgcacggcac cggaacaggc ggacctggat atacgattaa    9660
atgcgagaca aagggaatc  cgcacaaaca cgaagccggt tctctctcaa tggctcacgc    9720
aggaaaagat accggaggca gccaatttt  tatcgtccat gagcctcagc cgcacttgaa    9780
cggcgttcac accgttttcg gaaaggtcac atcaggcctt gatgccgtca cttcaatgga    9840
gcagggacaa ggcatggaaa agtcgaagt  atttgatgca taatcagaga gcgcaaaaaa    9900
cagcccgctt agccgggctg ttttttttgtc tgtaacggtg tttattttcc aggtgcaaca    9960
ggacttgagg ccgattcttc gtccacatcc tgataggaaa taacgatgct aataataaa    10020
ataattgtga aaaatgacc  ctttatgtaa aatatattca agtgaagagc tagatagaga   10080
acgcaatctg taaaaagga  aggggcgtaa ggggtgagcg taaaaatccc atcgacggca   10140
gtcggcgtaa aaattaatga ctggtataac gcgatacg                           10178
```

<210> SEQ ID NO 79
<211> LENGTH: 10178
<212> TYPE: DNA
<213> ORGANISM: Artificial Sequence
<220> FEATURE:
<223> OTHER INFORMATION: synthetic

<400> SEQUENCE: 79

```
catcggacag ctcttgcttg atatcttcaa aatgacgccg gctcatgtca tgtcaacttt      60
tgtcgtatct ggagcgatcc ttgacggatt cggcatttac gaccgttta  tcgaatttgc     120
cggtgccggg gctacagtcc cgattgtcag cttcggccac tctcttttgc acggcgcgat     180
gcaccaggct gagaaacatg gctttatcgg aatcggcatg gggatatttg aactgacatc     240
tgccggtata tctgccgcta tcttgttcgc ttttcttgtt gccgtgattt ttaaaccgaa     300
aggataaagg aaaatgccag caaaacgcaa ggtcattttg gtcacagacg gcgatatata     360
cgctgcaaaa gcaatcgaat atgcagcaag aaaaacgggt ggccgctgca tttcccaatc     420
ggcggggaat ccgagcgtta aaacaggacc ggagcttgta accatgatcc tgcaaacccc     480
tcatgatcct gtattcgtca tgtttgatga ttccggactt caaggtgaag gcccgggaga     540
gacagctatg aaatatgtag cgatgcatcc cgatatcgag gtgctcggag tcatcgccgt     600
cgcttcaaaa actcattatg cagagtggac gagagtcgat gtatcaatcg atgcagaagg     660
cgaactgaca gagtacggcg tcgataaaca cggggtcaaa gagttcgatg tcaaacgaat     720
gaatggtgat acagtctatt gccttgacca gctggatgtt ccgatcattg tcggaatcgg     780
tgatatcggt aagatgaaca gaaaagacga tgtggaaaaa ggttcgccga ttacaatgaa     840
agcggtcgag ctcatttttag aaaggagcgg gtatcatgag tgctcaaaag caagagaaga     900
cgaacgtatt ccttgatcct tctaagaatg aagcgtattt caagaagcgg gtcggcatgg     960
```

```
gagaaagctt tgaccttggc gtacggaagg tctttattct cggacatgaa gttcagcttt      1020
attatgtcaa cggattgtgc gacacacaat acatcattca cctgttaaga gaactggtgc      1080
atctgaatga taaagaaaaa gaatcgggcg aggtcgaaga catcgtcgaa acaggctttt      1140
tgaaccagca ggtttcaaaa gcggaaacgc ttgatgaagc tgtcgaccaa gtgttgtcag      1200
gactggttgc catcatcgtc gaagatgcgg gctttgcttt tatcatcgat gtcagaagct      1260
acccgggcag aacgccggaa gaacctgata cagaaaaagt cgtacgcggt gcaagggacg      1320
gactcgtcga gaacatcatc gtcaacacag ccctgattag acgccggatc agagatgagc      1380
gcttgcgcta caaaatgctt catatcggtg aacgctctaa aacagacatc tgcctctgct      1440
atttggaaga cgttgcagat cccgatcttg ttgaagtatt aaaaaaagaa attgaagatg      1500
tgaagatcga cgggctgccg atgtcggata atcggtaga ggaattcctg gtcggccaag       1560
gctacaatcc gtttccgctt gtcaggttta cggaaagggc agacgtagcc gcaagccata      1620
ttttagaggg gcatgtcatc gtgatcgtcg atacgtcgcc aagcgtcatc atcacaccga      1680
ccactttgtt tcaccatgtt cagcatgctg aggaatacag acagacgccg gctgttggga      1740 cgttttaag gtgggtgcgg ttttccggta ttttggcctc caccttttg ctgccgcttt        1800 ggctgctgtt tgtcattcat ccgtcgctct tgcctgataa tttatcgttt atcgggttga      1860
ataaagacac ccatattccg attatcatgc agattttcct ggcggatctc ggcgtcgaat      1920
ttttaagaat ggccgccatt catacgccga cggcgctttc gactgcaatg ggcctgatcg      1980
ccgctgtatt gatcggcgat atcgcgatca atgtcggctt gttttctccc gaagtcattt      2040
tatacgtttc cctctcggca atcggagcct acacgacacc aagctacgag ctgagcctgg      2100
cgaataaaat ggtgaagctg tttatgctga tattggtggc gcttttaaa gtggagggat       2160 ttgtcatcgg attaacgatc ttaactatag tgatgacttc gatcaggtca ttgcgaacgc      2220
cttacttatg gcctctcctc ccgttcaatg gaaaagcgtt ttggcatgtt ctcgtgcgca      2280
cgtccgttcc aggggaaaa gtcaggccga gcatcgttca tccgagaaac cgctccagac       2340
agccgtgaag ccggcattcg aagaggcttt tccccgggga aaagcctctt tttcaataat      2400
cgaattccgg tctttgagta ccgatgcctc tgtattcatt ggcagagatc gcgactgccc      2460
ggaggctgca gatgttgttc tgtcttctga tcggatagac gacatacagc atttcgcggc      2520
cgtacgggtc aatcgttgac gaatgaagga aaacctcagt tcctctcccgc caaaatctcg     2580 tattcgccgg agctgtaata atctgcccct cataaggctc ataaattctc tgttcataat     2640
gcgcagccgc ctgataaggg gcgtatacat cttcaggtgc atagccggga gcggggtgt       2700 agggatagcg atttggatac atatgataac ctctttccca cttcgttttt tggttttcat     2760
ctttaagatt atattcaggt aaatgcctat ttgtatgggc gaaaatctca gcttttcggc      2820
tcttttttta ttgaatggac gttgtgtatg cctatttcta tcaagcgctg ttttctgtta     2880
ttctataatc aatagaatgg attagttgtt tagggaatca tttcctttat aaatcaagaa      2940
aatttggaca aatggtggtt tagttttta aacgaaatgt tataatacaa cataagaatc       3000
gcactatcat gaagccggaa gatgcatcgg gcagcaaccg gagcgcccct tgcacctttg      3060
tcgatagaga aagagggaat gacaattgtt tttacacggt actagcagac aaaatgaaag      3120
agggcaccct gaaatcggcg gtgtcgatgt tctatcattg gcagaaagat acggaacacc      3180
tctttatgta tacgatgtcg cgctgattag agagcgcgcc cgaaaattcc agaaggcatt     3240
caaggaagcc ggtttaaaag cgcaggtagc gtatgcaagc aaggcgtttt catcggttgc      3300
```

```
catgattcag cttgccgaac aagaggggct gtctctggat gtggtatcgg gaggagagct   3360
tttcactgcg atcaaagcag ggttcccagc tgagcggatt cattttcacg gaaacaataa   3420
gagccctgaa gaactagcca tggcgctgga gcatcaaatc ggctgcatcg tgctcgataa   3480
cttcacgag atcgccatta cagaagatct ttgcaagcga tcaggacaaa ctgtagacgt   3540
tttgctcaga atcactccgg gagttgaagc gcacacgcac gattatatta cgacggggca   3600
ggaagattcc aaattcggtt ttgatctgca taatggacag gtcgaacaag ccatcgaaca   3660
agtcctccgc tcgtctgcgt ttaagctcct cggcgtgcac tgccacatcg gttcgcaaat   3720
ttttgatacg gcaggatttg tccttgcagc agacaagatt ttcgagaagc ttgcggaatg   3780
gcgggagact tactctttca ttccggaagt gctcaatctt ggcgggggct tcggcatccg   3840
ctatacaaaa gacgacgagc cgcttgcagc tgatgtttat gttgaaaaaa tcatcgaggc   3900
ggtcaaagca aatgccgagc atttcggctt tgacatccct gagatttgga tcgaaccagg   3960
ccggtctctc gtcggtgatg cggggactac gctgtacacg atcggttctc aaaaagaggt   4020
gccgggcatt cgcaaatatg tagccatcga cggcggcatg agcgataata tcaggccggc   4080
gctttatgag gcaaaatatg aagcagccgt cgccaacagg atgaacgatg cttgtcatga   4140
taccgcatca atcgcaggaa aatgctgcga aagcggagat atgctgattt gggatttgga   4200
aatccccgaa gttcgcgacg gagatgtgct cgccgttttc tgcaccggtg cgtacggcta   4260
cagcatggcc aacaactaca accgcattcc gcgcccggcc gtcgtctttg tcgaggacgg   4320
ggaagcgcag ctcgtcattc agagagagac gtatgaggat atcgtcaagc tggatctgcc   4380
gctgaaatcg aaagtcaaac aataaaaaaa tggagattcc ctaagagggg ggtctccatt   4440
tttaattcag cttttctttt ggaagaaaat atagggaaaa tggtacttgt taaaaattcg   4500
gaatatttat acaatatcat tgttttcaca ttgaagggg aggagaatca tgaaacaaca   4560
aaaacggctt tacgcccgat tgctgacgct gttatttgcg ctcatcttct tgctgcctca   4620
ttctgcagct tcagcagcag ctaaacccgc tgtaagcaac gcttatttag atgcttcaaa   4680
ccaggtgctg gttaaactta gccagccgtt aactcttggg gaaggcgcaa gcggctttac   4740
ggttcatgac gacacagcaa ataaggatat tccagtgaca tctgtgaagg atgcaagtct   4800
tggtcaagat gtaaccgctg ttttggcagg taccttccaa catatttttg gaggttccga   4860
ttgggcaccct gataatcaca gtactttatt aaaaaaggtg actaacaatc tctatcaatt   4920
ctcaggagat cttcctgaag gaaactacca atataaagtg gctttaaatg atagctggaa   4980
taatccgagt tacccatctg acaacattaa tttaacagtc cctgccggcg gtgcacacgt   5040
cacttttttcg tatattccgt ccactcatgc agtctatgac acaattaata atcctaatgc   5100
ggatttacaa gtgaaagcg gggttaaaac ggatctcgtg acggttactc taggggaaga   5160
tccagatgtg agccatactc tgtccattca aacagatggc tatcaggcaa agcaggtgat   5220
acctcgtaac gtgcttaatt catcacagta ctactattca ggagatgatc ttgggaatac   5280
ctatacacag aaagcaacaa cctttaaagt ctgggcacca acttctactc aagtaaatgt   5340
tcttctttat gacagtgcaa cgggttctgt aacaaaaatc gtacctatga cggcatcggg   5400
ccatggtgtg tgggaagcaa cggttaatca aaaccttgaa aattggtatt acatgtatga   5460
ggtaacaggc caaggctcta cccgaacggc tgttgatcct tatgcaactg cgattgcacc   5520
aaatggaacg agaggcatga ttgtggacct ggctaaaaca gatcctgctg gctggaacag   5580
tgataaacat attacgccaa agaatataga agatgaggtc atctatgaaa tggatgtccg   5640
tgacttttcc attgacccta attcgggtat gaaaaataaa gggaagtatt tggctcttac   5700
```

```
agaaaaagga acaaagggcc ctgacaacgt aaagacgggg atagattcct taaaacaact    5760
tgggattact catgttcagc ttatgcctgt tttcgcatct aacagtgtcg atgaaactga    5820
tccaacccaa gataatttggg gttatgaccc tcgcaactat gatgttcctg aagggcagta   5880
tgctacaaat gcgaatggta atgctcgtat aaaagagttt aaggaaatgg ttctttcact    5940
ccatcgtgaa cacattgggg ttaacatgga tgttgtctat aatcatacct ttgccacgca    6000
aatctctgac ttcgataaaa ttgtaccaga atattattac cgtacggatg atgcaggtaa    6060
ttataccaac ggatcaggta ctggaaatga aattgcagcc gaaaggccaa tggttcaaaa    6120
atttattatt gattccctta agtattgggt caatgagtat catattgacg cttccgttt    6180 tgacttaatg gcgctgcttg gaaaagacac gatgtccaaa gctgcctcgg agcttcatgc    6240
tattaatcca ggaattgcac tttacggtga gccatggacg ggtggaacct ctgcactgcc    6300
agatgatcag cttctgacaa aaggagctca aaaaggcatg ggagtagcgg tgtttaatga    6360
caatttacga aacgcgttgg acggcaatgt ctttgattct tccgctcaag gttttgcgac    6420
aggtgcaaca ggcttaactg atgcaattaa gaatggcgtt gaggggagta ttaatgactt    6480
tacctcttca ccaggtgaga caattaacta tgtcacaagt catgataact acacccttg     6540 ggacaaaata gccctaagca atcctaatga ttccgaagcg gatcggatta aaatggatga    6600
actcgcacaa gcagttgtta tgacctcaca aggcgttcca ttcatgcaag gcggggaaga    6660
aatgcttcgt acaaaaggcg gcaacgacaa tagttataat gcaggcgatg cggtcaatga    6720
gtttgattgg agcaggaaag ctcaaatatcc agatgttttc aactattata gcgggctaat    6780
ccaccttcgt cttgatcacc cagccttccg catgacgaca gctaatgaaa tcaatagcca    6840
cctccaattc ctaaatagtc cagagaacac agtggcctat gaattaactg atcatgttaa    6900
taaagacaaa tggggaaata tcattgttgt ttataaccca aataaaactg tagcaaccat    6960
caatttgccg agcgggaaat gggcaatcaa tgctacgagc ggtaaggtag gagaatccac    7020
ccttggtcaa gcagagggaa gtgtccaagt accaggtata tctatgatga tccttcatca    7080
agaggtaagc ccagaccacg gtaaaaagta aaagagcaga gaggacggat ttcctgaagg    7140
aaatccgttt ttttatttc aagcacgaaa acacttccc ggtgatcggg aggtgttttt       7200
tgttaaaaag atcatgacat gcatagaaca gcgaccgggc taattgtata taatattgtg    7260
aatttaacaa aaaatttaca aaggagatga taaaggcaat gaccagggtg aaaaggatga    7320
gatttgctga tttgttggat ttagaggcgg agtagatgaa accggccaaa gtatccctac    7380
tccaccgatt gctccagtgc ctgaagcaat gtgttgattg taacacagta aatcgtttta    7440
cagcaataaa catttttgtg aatattttat tgatttcggc tgtgatctca ttcccatatt    7500
ctgctgcggc ccatggcgca acacagtccg gcgatcaata ttcaagcttt gaagaattgg    7560
agcggaatga agatccagct tcttaccgaa ttacggagaa gaacgcaaga gtgccgatgc    7620
tcatcatggc catccatgga ggcggcatcg aacccggaac gagcgaaatc gccaatgaag    7680
tgtccaaaaa ctattccctg tacttgtttg aagggctgaa atcatcaggc aatacggacc    7740
ttcacattac aagcacgcgt tttgacgagc cagcggcgct cgcaattact gcaagccacc    7800
agtatgtcat gtcgctccac ggctattaca gtgaagaccg cgatattaaa gtaggcggca    7860
cagaccgcgc taaaatcaga atattggttg atgagctgaa ccgctcgggg tttgccgctg    7920
aaatgctggg gacagatgac aagtatgccg gaacccatcc gaataacatc gccaacaagt    7980
cgctttccgg gctgagcatt cagcttgaaa tgagcacggg tttccgcaaa tctttattcg    8040
```

| | | | | | |
|---|---|---|---|---|---|
| accggtttac | actaaaagac | agggcggcga | cgcaaaacga | aacgttttac | cgatttacaa | 8100 |
| agctgctgac | agattttatt | catgaaaact | atgaagaaga | cggaggggat | ttcccctctg | 8160 |
| caaaaataaa | acaccccctt | caagtgaaaa | aggaggtgtt | tcggcggttg | tgttaaccgt | 8220 |
| tggactctga | ggtgccgccg | ccggtgaata | cggaaacgat | ggcgttccac | agagacacaa | 8280 |
| agaagtcgat | cagttttttga | agaaagtttt | gtccttcttc | agaatccaag | aatttcgtga | 8340 |
| ttttatcctt | tgctttgtca | agctggtctc | caacctggtt | ccagtcgata | ttaatatttt | 8400 |
| tcatgttatt | aaataaagat | ataagagagt | ttttctgatc | ttctgtgagt | gtcacgccaa | 8460 |
| gttcggaagc | agccgaatca | atcgttttct | ccaattcctc | ttttgactcg | ggaactccgt | 8520 |
| ttttcgagat | ttcttccttg | actttggcca | tcagcgctga | cgcgttttca | ctgccgattt | 8580 |
| tctcgccaag | ctctgaagtg | gtgacaagct | cttcattcgc | gaccttttc | acatcttcgg | 8640 |
| aaatttttc | gcccgaagtc | gtttcatacg | cttttcatcaa | tccggttaaa | gcggctgtgc | 8700 |
| ctgacacttc | aaacggagcg | gtgacataga | ctttggcgtc | ttttacaccg | gccgtcatca | 8760 |
| gcgcgttcaa | atacatctca | tctgtaattc | tgctgatatt | gtgtgtctga | acttccaaac | 8820 |
| cggtgccttt | tttcgctacg | gtaattgaag | aagaagaaat | cgctcttgtt | ccgatttgtg | 8880 |
| ctttcggtat | ataatcccct | aaatatttat | gctcctcatc | atttgtcacc | tcgatgatgg | 8940 |
| tcgcattttc | aggcgcattc | atttctttta | atacttttg | tctgtcctgg | cttgacaagt | 9000 |
| cttttccccag | cgtgacgatg | acatcaccca | ctgcggcgtc | agcgaagctg | acctgcggga | 9060 |
| aaatgagcag | acacaatgct | gtaaagattc | ctagtatcga | ttttttcaag | ctcaatgccc | 9120 |
| tccttaaaaa | tgcaggcttc | aggcagaatt | gctgtacttt | taaagaagcc | tgccggaacg | 9180 |
| gaaataatgc | gttccgaaat | atagacggat | gaaagatgag | tgaggtttca | agaaaaaaaa | 9240 |
| gagagaattt | tctcttcaag | tcaaatgccc | tcccggcatc | gtatctcgcc | gctctttat | 9300 |
| cattcatgat | tttcacaggc | gattcaacct | tttttaaaa | tttttacaa | aaacgataca | 9360 |
| agagcggcgt | ttatttcggt | cgattggctc | tctgcttctt | caatatgata | taatgacccct | 9420 |
| tgtgaaatga | aaggagagaa | tcaagatggc | taaaaaagga | tacatacaac | tgacaaacgg | 9480 |
| caaaaaaatc | gagtttgaac | tatatccgga | tgcggcgccg | ggaactgtcg | ccaactttga | 9540 |
| aaaacttgca | aacgaagggt | tctatgacgg | gctgaagttc | caccgcgtca | tcccgggctt | 9600 |
| cgtcagccag | ggaggctgcc | cgcacggcac | cggaacaggc | ggacctggat | atacgattaa | 9660 |
| atgcgagaca | gaagggaatc | cgcacaaaca | cgaagccggt | tctctctcaa | tggctcacgc | 9720 |
| aggaaaagat | accggaggca | gccaatttt | tatcgtccat | gagcctcagc | cgcacttgaa | 9780 |
| cggcgttcac | accgttttcg | gaaaggtcac | atcaggcctt | gatgccgtca | cttcaatgga | 9840 |
| gcagggacaa | ggcatggaaa | aagtcgaagt | atttgatgca | taatcagaga | gcgcaaaaaa | 9900 |
| cagcccgctt | agccgggctg | tttttttgtc | tgtaacggtg | tttattttcc | aggtgcaaca | 9960 |
| ggacttgagg | ccgattcttc | gtccacatcc | tgataggaaa | taacgatgct | aataaataaa | 10020 |
| ataattgtga | aaaaatgacc | ctttatgtaa | aatatattca | agtgaagagc | tagatagaga | 10080 |
| acgcaatctg | taaaaaagga | aggggcgtaa | ggggtgagcg | taaaaatccc | atcgacggca | 10140 |
| gtcggcgtaa | aaattaatga | ctggtataac | gcgatacg | | | 10178 |

<210> SEQ ID NO 80
<211> LENGTH: 10270
<212> TYPE: DNA
<213> ORGANISM: Artificial Sequence
<220> FEATURE:
<223> OTHER INFORMATION: synthetic

<400> SEQUENCE: 80

```
ctagcgtgtc ctcgcatagt tcttagattg tcgctacggc atatacgatc cgtgagacgt    60
catcggacag ctcttgcttg atatcttcaa aatgacgccg gctcatgtca tgtcaacttt   120
tgtcgtatct ggagcgatcc ttgacggatt cggcatttac gaccgtttta tcgaatttgc   180
cggtgccggg gctacagtcc cgattgtcag cttcggccac tctcttttgc acggcgcgat   240
gcaccaggct gagaaacatg gctttatcgg aatcggcatg gggatatttg aactgacatc   300
tgccggtata tctgccgcta tcttgttcgc ttttcttgtt gccgtgattt ttaaaccgaa   360
aggataaagg aaaatgccag caaaacgcaa ggtcattttg gtcacagacg gcgatatata   420
cgctgcaaaa gcaatcgaat atgcagcaag aaaaacgggt ggccgctgca tttcccaatc   480
ggcgggaat ccgagcgtta aaacaggacc ggagcttgta accatgatcc tgcaaacccc   540
tcatgatcct gtattcgtca tgtttgatga ttccggactt caaggtgaag gcccgggaga   600
gacagctatg aaatatgtag cgatgcatcc cgatatcgag gtgctcggag tcatcgccgt   660
cgcttcaaaa actcattatg cagagtggac gagagtcgat gtatcaatcg atgcagaagg   720
cgaactgaca gagtacggcg tcgataaaca cggggtcaaa gagttcgatg tcaaacgaat   780
gaatggtgat acagtctatt gccttgacca gctggatgtt ccgatcattg tcggaatcgg   840
tgatatcggt aagatgaaca gaaaagacga tgtggaaaaa ggttcgccga ttacaatgaa   900
agcggtcgag ctcattttag aaaggagcgg gtatcatgag tgctcaaaag caagagaaga   960
cgaacgtatt ccttgatcct tctaagaatg aagcgtattt caagaagcgg gtcggcatgg  1020
gagaaagctt tgaccttggc gtacggaagg tctttattct cggacatgaa gttcagcttt  1080
attatgtcaa cggattgtgc gacacacaat acatcattca cctgttaaga gaactggtgc  1140
atctgaatga taaagaaaaa gaatcgggcg aggtcgaaga catcgtcgaa aacaggcttt  1200
tgaaccagca ggtttcaaaa gcggaaacgc ttgatgaagc tgtcgaccaa gtgttgtcag  1260
gactggttgc catcatcgtc gaagatgcgg gctttgcttt tatcatcgat gtcagaagct  1320
acccgggcag aacgccggaa gaacctgata cagaaaaagt cgtacgcggt gcaagggacg  1380
gactcgtcga gaacatcatc gtcaacacag ccctgattag acgccggatc agagatgagc  1440
gcttgcgcta caaaatgctt catatcggtg aacgctctaa aacagacatc tgcctctgct  1500
atttggaaga cgttgcagat cccgatcttg ttgaagtatt aaaaaaagaa attgaagatg  1560
tgaagatcga cgggctgccg atgtcggata atcggtaga ggaattcctg gtcggccaag  1620
gctacaatcc gtttccgctt gtcaggttta cggaaagggc agacgtagcc gcaagccata  1680
ttttagaggg gcatgtcatc gtgatcgtcg atacgtcgcc aagcgtcatc atcacaccga  1740
ccactttgtt tcaccatgtt cagcatgctg aggaatacag acagacgccg gctgttggga  1800
cgttttaag gtgggtgcgg ttttcggta ttttggcctc cacctttttg ctgccgcttt  1860
ggctgctgtt tgtcattcat ccgtcgctct gcctgataa tttatcgttt atcgggttga  1920
ataaagacac ccatattccg attatcatgc agattttcct ggcggatctc ggcgtcgaat  1980
ttttaagaat ggccgccatt catacgccga cggcgctttc gactgcaatg ggcctgatcg  2040
ccgctgtatt gatcggcgat atcgcgatca atgtcggctt gttttctccc gaagtcattt  2100
tatacgtttc cctctcggca atcggagcct acacgacacc aagctacgag ctgagcctgg  2160
cgaataaaat ggtgaagctg tttatgctga tattggtggc gcttttttaaa gtggagggat  2220
ttgtcatcgg attaacgatc ttaactatag tgatgacttc gatcaggtca ttgcgaacgc  2280
```

```
cttacttatg gcctctcctc ccgttcaatg gaaaagcgtt ttggcatgtt ctcgtgcgca   2340
cgtccgttcc aggggaaaa gtcaggccga gcatcgttca tccgagaaac cgctccagac    2400
agccgtgaag ccggcattcg aagaggcttt tccccgggga aaagcctctt tttcaataat   2460
cgaattccgg tctttgagta ccgatgcctc tgtattcatt ggcagagatc gcgactgccc   2520
ggaggctgca gatgttgttc tgtcttctga tcggatagac gacatacagc atttcgcggc   2580
cgtacgggtc aatcgttgac gaatgaagga aaacctcagt tcctctccgc caaaatctcg   2640
tattcgccgg agctgtaata atctgcccttt cataaggctc ataaattctc tgttcataat   2700
gcgcagccgg ctgataaggg gcgtatacat cttcaggtgc atagccggga gcggggtgt    2760 agggatagcg atttggatac atatgataac ctctttccca cttcgttttt tggttttcat   2820
ctttaagatt atattcaggt aaatgcctat ttgtatgggc gaaatctca gcttttcggc    2880 tctttttta ttgaatggac gttgtgtatg cctatttcta tcaagcgctg ttttctgtta    2940
ttctataatc aatagaatgg attagttgtt tagggaatca tttcctttat aaatcaagaa   3000
aatttggaca aatggtggtt tagttttttaa acgaaatgt tataatacaa cataagaatc   3060
gcactatcat gaagccggaa gatgcatcgg gcagcaaccg gagcgcccct tgcacctttg   3120
tcgatagaga aagagggaat gacaattgtt tttacacggt actagcagac aaaatgaaag   3180
agggcacctc gaaatcggcg gtgtcgatgt tctatcattg gcagaaagat acggaacacc   3240
tctttatgta tacgatgtcg cgctgattag agagcgcgcc cgaaaattcc agaaggcatt   3300
caaggaagcc ggtttaaaag cgcaggtagc gtatgcaagc aaggcgtttt catcggttgc   3360
catgattcag cttgccgaac aagaggggct gtctctggat gtggtatcgg gaggagagct   3420
tttcactgcg atcaaagcag ggttcccagc tgagcggatt cattttcacg gaaacaataa   3480
gagccctgaa gaactagcca tggcgctgga gcatcaaatc ggctgcatcg tgctcgataa   3540
ctttcacgag atcgccatta cagaagatct ttgcaagcga tcaggacaaa ctgtagacgt   3600
tttgctcaga atcactccgg gagttgaagc gcacacgcac gattatatta cgacggggca   3660
ggaagattcc aaaattcggtt ttgatctgca taatggacag gtcgaacaag ccatcgaaca   3720
agtcctccgc tcgtctgcgt ttaagctcct cggcgtgcac tgccacatcg gttcgcaaat   3780
ttttgatacg gcaggatttg tccttgcagc agacaagatt ttcgagaagc ttgcggaatg   3840 gcggagagact tactctttca ttccggaagt gctcaatctt ggcgggggct tcggcatccg   3900
ctatacaaaa gacgacgagc cgcttgcagc tgatgtttat gttgaaaaaa tcatcgaggc   3960
ggtcaaagca aatgccgagc atttcggctt tgacatccct gagatttgga tcgaaccagg   4020
ccggtctctc gtcggtgatg cggggactac gctgtacacg atcggttctc aaaaagaggt   4080
gccgggcatt cgcaaatatg tagccatcga cggcggcatg agcgataata tcaggccggc   4140
gctttatgag gcaaaatatg aagcagccgt cgccaacagg atgaacgatg cttgtcatga   4200
taccgcatca atcgcaggaa aatgctgcga aagcggagat atgctgattt gggatttgga   4260
aatccccgaa gttcgcgacg gagatgtgct cgccgttttc tgcaccggtg cgtacggcta   4320
cagcatggcc aacaactaca accgcattcc gcgcccggcc gtcgtctttg tcgaggacgg   4380
ggaagcgcag ctcgtcattc agagagagac gtatgaggat atcgtcaagc tggatctgcc   4440
gctgaaatcg aaagtcaaac aataaaaaaa tggagattcc ctaagagggg ggtctccatt   4500
tttaattcag cttttctttt ggaagaaaat atagggaaaa tggtacttgt taaaaattcg   4560
gaatatttat acaatatcat atgacagaat agtcttttaa gtaagtctac tctgaatttt   4620
tttaaaagga gagggtaaag aatgaaacaa caaaaacggc tttacgcccg attgctgacg   4680
```

```
ctgttatttg cgctcatctt cttgctgcct cattctgcag cttcagcagc agctaaaccc    4740
gctgtaagca acgcttattt agatgcttca aaccaggtgc tggttaaact tagccagccg    4800
ttaactcttg gggaaggcgc aagcggcttt acggttcatg acgacacagc aaataaggat    4860
attccagtga catctgtgaa ggatgcaagt cttggtcaag atgtaaccgc tgttttggca    4920
ggtaccttcc aacatatttt tggaggttcc gattgggcac ctgataatca cagtacttta    4980
ttaaaaaagg tgactaacaa tctctatcaa ttctcaggag atcttcctga aggaaactac    5040
caatataaag tggctttaaa tgatagctgg aataatccga gttacccatc tgacaacatt    5100
aatttaacag tccctgccgg cggtgcacac gtcactttt cgtatattcc gtccactcat     5160
gcagtctatg acacaattaa taatcctaat gcggatttac aagtagaaag cggggttaaa    5220
acggatctcg tgacggttac tctaggggaa gatccagatg tgagcccatac tctgtccatt   5280 caaacagatg gctatcaggc aaagcaggtg atacctcgta acgtgcttaa ttcatcacag    5340
tactactatt caggagatga tcttgggaat acctatacac agaaagcaac aacctttaaa    5400
gtctgggcac caacttctac tcaagtaaat gttcttcttt atgacagtgc aacgggttct    5460
gtaacaaaaa tcgtacctat gacggcatcg ggccatggtg tgtgggaagc aacggttaat    5520
caaaaccttg aaaattggta ttacatgtat gaggtaacag gccaaggctc tacccgaacg    5580
gctgttgatc cttatgcaac tgcgattgca ccaaatggaa cgagaggcat gattgtggac    5640
ctggctaaaa cagatcctgc tggctggaac agtgataaac atattacgcc aaagaatata    5700
gaagatgagg tcatctatga aatggatgtc cgtgactttt ccattgaccc taattcgggt    5760
atgaaaaata agggaagta tttggctctt acagaaaaag gaacaaaggg ccctgacaac    5820
gtaaagacgg ggatagattc cttaaaacaa cttgggatta ctcatgttca gcttatgcct    5880
gttttcgcat ctaacagtgt cgatgaaact gatccaaccc aagataattg gggttatgac    5940
cctcgcaact atgatgttcc tgaagggcag tatgctacaa atgcgaatgg taatgctcgt    6000
ataaaagagt ttaaggaaat ggttctttca ctccatcgtg aacacattgg ggttaacatg    6060
gatgttgtct ataatcatac ctttgccacg caaatctctg acttcgataa aattgtacca    6120
gaatattatt accgtacgga tgatgcaggt aattatacca acggatcagg tactggaaat    6180
gaaattgcag ccgaaaggcc aatggttcaa aaatttatta ttgattccct taagtattgg    6240
gtcaatgagt atcatattga cggcttccgt tttgacttaa tggcgctgct tggaaaagac    6300
acgatgtcca agctgcctc ggagcttcat gctattaatc caggaattgc actttacggt    6360
gagccatgga cgggtggaac ctctgcactg ccagatgatc agcttctgac aaaaggagct    6420
caaaaaggca tgggagtagc ggtgtttaat gacaatttac gaaacgcgtt ggacggcaat    6480
gtctttgatt cttccgctca aggttttgcg acaggtgcaa caggcttaac tgatgcaatt    6540
aagaatggcg ttgaggggag tattaatgac tttacctctt caccaggtga gacaattaac    6600
tatgtcacaa gtcatgataa ctacacccct tgggacaaaa tagccctaag caatcctaat    6660
gattccgaag cggatcggat taaaatggat gaactcgcac aagcagttgt tatgacctca    6720
caaggcgttc cattcatgca aggcgggaa gaaatgcttc gtacaaaagg cggcaacgac    6780
aatagttata atgcaggcga tgcggtcaat gagtttgatt ggagcaggaa agctcaatat    6840
ccagatgttt tcaactatta tagcgggcta atccaccttc gtcttgatca cccagccttc    6900
cgcatgacga cagctaatga aatcaatagc cacctccaat tcctaaatag tccagagaac    6960
acagtggcct atgaattaac tgatcatgtt aataaagaca aatggggaaa tatcattgtt    7020
```

```
gtttataacc caaataaaac tgtagcaacc atcaatttgc cgagcgggaa atgggcaatc    7080
aatgctacga gcggtaaggt aggagaatcc acccttggtc aagcagaggg aagtgtccaa    7140
gtaccaggta tatctatgat gatccttcat caagaggtaa gcccagacca cggtaaaaag    7200
taaaagagca gagaggacgg atttcctgaa ggaaatccgt ttttttattt tcaagcacga    7260
aaaacacttc ccggtgatcg ggaggtgttt tttgttaaaa agatcatgac atgcatagaa    7320
cagcgaccgg gctaattgta tataatattg tgaatttaac aaaaaattta caaaggagat    7380
gataaaggca atgaccaggg tgaaaaggat gagatttgct gatttgttgg atttagaggc    7440
ggagtagatg aaaccggcca aagtatccct actccaccga ttgctccagt gcctgaagca    7500
atgtgttgat tgtaacacag taaatcgttt tacagcaata acattttttg tgaatatttt    7560
attgatttcg gctgtgatct cattcccata ttctgctgcg gcccatggcg caacacagtc    7620
cggcgatcaa tattcaagct ttgaagaatt ggagcggaat gaagatccag cttcttaccg    7680
aattacggag aagaacgcaa gagtgccgat gctcatcatg gccatccatg gaggcggcat    7740
cgaacccgga acgagcgaaa tcgccaatga agtgtccaaa actattccc tgtacttgtt    7800 tgaagggctg aaatcatcag gcaatacgga ccttcacatt acaagcacgc gttttgacga    7860
gccagcggcg ctcgcaatta ctgcaagcca ccagtatgtc atgtcgctcc acggctatta    7920
cagtgaagac cgcgatatta agtaggcgg cacagaccgc gctaaaatca gaatattggt    7980
tgatgagctg aaccgctcgg ggtttgccgc tgaaatgctg gggacagatg acaagtatgc    8040
cggaacccat ccgaataaca tcgccaacaa gtcgctttcc gggctgagca ttcagcttga    8100
aatgagcacg ggtttccgca aatctttatt cgaccggttt acactaaaag acagggcggc    8160
gacgcaaaac gaaacgtttt accgatttac aaagctgctg acagatttta ttcatgaaaa    8220
ctatgaagaa gacggagggg atttcccctc tgcaaaaata aaacaccccc ttcaagtgaa    8280 aaggaggtg tttcggcggt tgtgttaacc gttggactct gaggtgccgc cgccggtgaa    8340
tacgaaaacg atggcgttcc acagagacac aaagaagtcg atcagttttt gaagaaagtt    8400
ttgtccttct tcagaatcca agaatttcgt gattttatcc tttgctttgt caagctggtc    8460
tccaacctgg ttccagtcga tattaatatt tttcatgtta ttaaataaag atataagaga    8520 gttttttctga tcttctgtga gtgtcacgcc aagttcggaa gcagccgaat caatcgtttt    8580
ctccaattcc tcttttgact cgggaactcc gttttttcgag atttcttcct tgactttggc    8640
catcagcgct gacgcgtttt cactgccgat tttctcgcca agctctgaag tggtgacaag    8700
ctcttcattc gcgaccttt tcacatcttc ggaattttt tcgcccgaag tcgtttcata    8760
cgctttcatc aatccggtta aagcggctgt gcctgacact tcaaacggag cggtgacata    8820
gactttggcg tcttttacac cggccgtcat cagcgcgttc aaatacatct catctgtaat    8880
tctgctgata ttgtgtgtct gaacttccaa accggtgcct ttttcgcta cggtaattga    8940 agaagaagaa atcgctcttg ttccgatttg tgctttcggt atataatccc ctaaatattt    9000
atgctcctca tcatttgtca cctcgatgat ggtcgcattt tcaggcgcat tcatttctttt    9060 taatactttt tgtctgtcct ggcttgacaa gtctttcccc agcgtgacga tgacatcacc    9120
cactgcggcg tcagcgaagc tgacctgcgg gaaaatgagc agacacaatg ctgtaaagat    9180
tcctagtatc gatttttttca agctcaatgc cctccttaaa aatgcaggct tcaggcagaa    9240
ttgctgtact tttaaagaag cctgccggaa cggaaataat gcgttccgaa atatagacgg    9300
atgaaagatg agtgaggttt caagaaaaaa aagagagaat tttctcttca agtcaaatgc    9360
cctcccggca tcgtatctcg ccgctctttt atcattcatg attttcacag gcgattcaac    9420
```

```
cttttttttaa aattttttac aaaaacgata caagagcggc gtttatttcg gtcgattggc    9480
tctctgcttc ttcaatatga tataatgacc cttgtgaaat gaaaggagag aatcaagatg    9540
gctaaaaaag gatacataca actgacaaac ggcaaaaaaa tcgagtttga actatatccg    9600
gatgcggcgc cgggaactgt cgccaacttt gaaaaacttg caaacgaagg gttctatgac    9660
gggctgaagt tccaccgcgt catcccgggc ttcgtcagcc agggaggctg cccgcacggc    9720
accggaacag gcggacctgg atatacgatt aaatgcgaga cagaagggaa tccgcacaaa    9780
cacgaagccg ttctctctc aatggctcac gcaggaaaag ataccggagg cagccaattt    9840
tttatcgtcc atgagcctca gccgcacttg aacggcgttc acaccgtttt cggaaaggtc    9900
acatcaggcc ttgatgccgt cacttcaatg gagcagggac aaggcatgga aaaagtcgaa    9960
gtatttgatg cataatcaga gagcgcaaaa acagcccgc ttagccgggc tgttttttg    10020 tctgtaacgg tgtttatttt ccaggtgcaa caggacttga ggccgattct tcgtccacat   10080
cctgatagga ataacgatg ctaataaata aaataattgt gaaaaaatga ccctttatgt    10140
aaaatatatt caagtgaaga gctagataga gaacgcaatc tgtaaaaaag gaaggggcgt    10200 aagggggtgag cgtaaaaaatc ccatcgacgg cagtcggcgt aaaaattaat gactggtata   10260
acgcgatacg                                                           10270
```

<210> SEQ ID NO 81
<211> LENGTH: 10270
<212> TYPE: DNA
<213> ORGANISM: Artificial Sequence
<220> FEATURE:
<223> OTHER INFORMATION: synthetic

<400> SEQUENCE: 81

```
ctagcgtgtc ctcgcatagt tcttagattg tcgctacggc atatacgatc cgtgagacgt      60
catcggacag ctcttgcttg atatcttcaa aatgacgccg gctcatgtca tgtcaacttt     120
tgtcgtatct ggagcgatcc ttgacggatt cggcatttac gaccgtttta tcgaatttgc     180
cggtgccggg gctacagtcc cgattgtcag cttcggccac tctcttttgc acggcgcgat     240
gcaccaggct gagaaacatg gctttatcgg aatcggcatg gggatatttg aactgacatc     300
tgccggtata tctgccgcta tcttgttcgc ttttcttgtt gccgtgattt ttaaaccgaa     360
aggataaagg aaaatgccag caaaacgcaa ggtcattttg gtcacagacg gcgatatata     420
cgctgcaaaa gcaatcgaat atgcagcaag aaaaacgggt ggccgctgca tttcccaatc     480
ggcggggaat ccgagcgtta aaacaggacc ggagcttgta accatgatcc tgcaaaccc     540 tcatgatcct gtattcgtca tgtttgatga ttccggactt caaggtgaag gcccgggaga     600
gacagctatg aaatatgtag cgatgcatcc cgatatcgag gtgctcggag tcatcgccgt     660
cgcttcaaaa actcattatg cagagtggac gagagtcgat gtatcaatcg atgcagaagg     720
cgaactgaca gagtacggcg tcgataaaca cggggtcaaa gagttcgatg tcaaacgaat     780
gaatggtgat acagtctatt gccttgacca gctggatgtt ccgatcattg tcggaatcgg     840
tgatatcggt aagatgaaca gaaaagacga tgtggaaaaa ggttcgccga ttacaatgaa     900
agcggtcgag ctcatttttag aaaggagcgg gtatcatgag tgctcaaaag caagagaaga     960
cgaacgtatt ccttgatcct tctaagaatg aagcgtattt caagaagcgg gtcggcatgg    1020
gagaaagctt tgaccttggc gtacggaagg tcttttattct cggacatgaa gttcagcttt    1080
attatgtcaa cggattgtgc gacacacaat acatcattca cctgttaaga gaactggtgc    1140
```

```
atctgaatga taaagaaaaa gaatcgggcg aggtcgaaga catcgtcgaa aacaggcttt    1200
tgaaccagca ggtttcaaaa gcggaaacgc ttgatgaagc tgtcgaccaa gtgttgtcag    1260
gactggttgc catcatcgtc gaagatgcgg gctttgcttt tatcatcgat gtcagaagct    1320
acccgggcag aacgccggaa gaacctgata cagaaaaagt cgtacgcggt gcaagggacg    1380
gactcgtcga gaacatcatc gtcaacacag ccctgattag acgccggatc agagatgagc    1440
gcttgcgcta caaaatgctt catatcggtg aacgctctaa aacagacatc tgcctctgct    1500
atttggaaga cgttgcagat cccgatcttg ttgaagtatt aaaaaaagaa attgaagatg    1560
tgaagatcga cgggctgccg atgtcggata aatcggtaga ggaattcctg gtcggccaag    1620
gctacaatcc gtttccgctt gtcaggttta cggaaagggc agacgtagcc gcaagccata    1680
ttttagaggg gcatgtcatc gtgatcgtcg atacgtcgcc aagcgtcatc atcacaccga    1740
ccactttgtt tcaccatgtt cagcatgctg aggaatacag acagacgccg gctgttggga    1800 cgttttaag gtgggtgcgg ttttcggta ttttggcctc cacctttttg ctgccgcttt    1860
ggctgctgtt tgtcattcat ccgtcgctct tgcctgataa tttatcgttt atcggggttga   1920 ataaagacac ccatattccg attatcatgc agattttcct ggcggatctc ggcgtcgaat    1980
ttttaagaat ggccgccatt catacgccga cggcgctttc gactgcaatg ggcctgatcg    2040
ccgctgtatt gatcggcgat atcgcgatca atgtcggctt gttttctccc gaagtcattt    2100
tatacgtttc cctctcggca atcggagcct acacgcacac aagctacgag ctgagcctgg    2160
cgaataaaat ggtgaagctg tttatgctga tattggtggc gcttttaaa gtggagggat    2220 ttgtcatcgg attaacgatc ttaactatag tgatgacttc gatcaggtca ttgcgaacgc    2280
cttacttatg gcctctcctc ccgttcaatg gaaaagcgtt ttggcatgtt ctcgtgcgca    2340
cgtccgttcc aggggaaaa gtcaggccga gcatcgttca tccgagaaac cgctccagac    2400
agccgtgaag ccggcattcg aagaggcttt tccccgggga aaagcctctt tttcaataat    2460
cgaattccgg tctttgagta ccgatgcctc tgtattcatt ggcagagatc gcgactgccc    2520
ggaggctgca gatgttgttc tgtcttctga tcggatagac gacatacagc atttcgcggc    2580
cgtacgggtc aatcgttgac gaatgaagga aaacctcagt tcctctccgc caaaatctcg    2640
tattcgccgg agctgtaata atctgcccct cataaggctc ataaattctc tgttcataat    2700
gcgcagccgc ctgataaggg gcgtatacat cttcaggtgc atagccggga gcggggtgt     2760 agggatagcg atttggatac atatgataac ctctttccca cttcgttttt tggttttcat    2820
ctttaagatt atattcaggt aaatgcctat ttgtatgggc gaaaatctca gcttttcggc    2880
tcttttttta ttgaatggac gttgtgtatg cctatttcta tcaagcgctg ttttctgtta    2940
ttctataatc aatagaatgg attagttgtt tagggaatca tttcctttat aaatcaagaa    3000
aatttggaca aatggtggtt tagttttta aacgaaatgt tataatacaa cataagaatc    3060
gcactatcat gaagccggaa gatgcatcgg gcagcaaccg gagcgcccct tgcacctttg    3120
tcgatagaga aagagggaat gacaattgtt tttacacggt actagcagac aaaatgaaag    3180
agggcacctc gaaatcggcg gtgtcgatgt tctatcattg gcagaaagat acggaacacc    3240
tctttatgta tacgatgtcg cgctgattag agagcgcgcc cgaaaattcc agaaggcatt    3300
caaggaagcc ggtttaaaag cgcaggtagc gtatgcaagc aaggcgtttt catcggttgc    3360
catgattcag cttgccgaac aagagggct gtctctggat gtggtatcgg gaggagagct    3420
tttcactgcg atcaaagcag ggttcccagc tgagcggatt cattttcacg gaaacaataa    3480
gagccctgaa gaactagcca tggcgctgga gcatcaaatc ggctgcatcg tgctcgataa    3540
```

```
ctttcacgag atcgccatta cagaagatct ttgcaagcga tcaggacaaa ctgtagacgt    3600
tttgctcaga atcactccgg gagttgaagc gcacacgcac gattatatta cgacgggca     3660 ggaagattcc aaattcggtt ttgatctgca taatggacag gtcgaacaag ccatcgaaca    3720
agtcctccgc tcgtctgcgt ttaagctcct cggcgtgcac tgccacatcg gttcgcaaat    3780
ttttgatacg gcaggatttg tccttgcagc agacaagatt ttcgagaagc ttgcggaatg    3840
gcgggagact tactctttca ttccggaagt gctcaatctt ggcggggggct tcggcatccg    3900 ctatacaaaa gacgacgagc cgcttgcagc tgatgtttat gttgaaaaaa tcatcgaggc    3960
ggtcaaagca aatgccgagc atttcggctt tgacatccct gagatttgga tcgaaccagg    4020
ccggtctctc gtcggtgatg cggggactac gctgtacacg atcggttctc aaaaagaggt    4080
gccgggcatt cgcaaatatg tagccatcga cggcggcatg agcgataata tcaggccggc    4140
gctttatgag gcaaaatatg aagcagccgt cgccaacagg atgaacgatg cttgtcatga    4200
taccgcatca atcgcaggaa aatgctgcga aagcggagat atgctgattt gggatttgga    4260
aatccccgaa gttcgcgacg gagatgtgct cgccgttttc tgcaccggtg cgtacggcta    4320
cagcatggcc aacaactaca accgcattcc gcgcccggcc gtcgtctttg tcgaggacgg    4380
ggaagcgcag ctcgtcattc agagagagac gtatgaggat atcgtcaagc tggatctgcc    4440
gctgaaatcg aaagtcaaac aataaaaaaa tggagattcc ctaagagggg ggtctccatt    4500
tttaattcag ctttttcttt ggaagaaaat atagggaaaa tggtacttgt taaaaattcg    4560
gaatatttat acaatatcat tgtacagaat agtctttaa gtaagtctac tctgaattt     4620 tttaaaagga gagggtaaag aatgaaacaa caaaaacggc tttacgcccg attgctgacg    4680
ctgttatttg cgctcatctt cttgctgcct cattctgcag cttcagcagc agctaaaccc    4740
gctgtaagca acgcttattt agatgcttca aaccaggtgc tggttaaact tagccagccg    4800
ttaactcttg gggaaggcgc aagcggcttt acggttcatg acgacacagc aaataaggat    4860
attccagtga catctgtgaa ggatgcaagt cttggtcaag atgtaaccgc tgttttggca    4920
ggtaccttcc aacatatttt tggaggttcc gattgggcac ctgataatca cagtacttta    4980 ttaaaaagg tgactaacaa tctctatcaa ttctcaggag atcttcctga aggaaactac    5040
caatataaag tggctttaaa tgatagctgg aataatccga gttacccatc tgacaacatt    5100
aatttaacag tccctgccgg cggtgcacac gtcactttttt cgtatattcc gtccactcat    5160
gcagtctatg acacaattaa taatcctaat gcggatttac aagtagaaag cggggttaaa    5220
acggatctcg tgacgttac tctaggggaa gatccagatg tgagccatac tctgtccatt    5280
caaacagatg gctatcaggc aaagcaggtg ataccctcgta acgtgcttaa ttcatcacag    5340
tactactatt caggagatga tcttgggaat acctatacac agaaagcaac aacctttaaa    5400
gtctgggcac caacttctac tcaagtaaat gttcttcttt atgacagtgc aacgggttct    5460
gtaacaaaaa tcgtacctat gacggcatcg ggccatggtg tgtgggaagc aacggttaat    5520
caaaaccttg aaaattggta ttacatgtat gaggtaacag gccaaggctc tacccgaacg    5580
gctgttgatc cttatgcaac tgcgattgca ccaaatggaa cgagaggcat gattgtggac    5640
ctggctaaaa cagatcctgc tggctggaac agtgataaac atattacgcc aaagaatata    5700
gaagatgagg tcatctatga aatggatgtc cgtgactttt ccattgaccc taattcgggt    5760
atgaaaaata aagggaagta tttggctctt acagaaaaag gaacaaaggg ccctgacaac    5820
gtaaagacgg ggatagattc cttaaaacaa cttgggatta ctcatgttca gcttatgcct    5880
```

```
gttttcgcat ctaacagtgt cgatgaaact gatccaaccc aagataattg gggttatgac    5940
cctcgcaact atgatgttcc tgaagggcag tatgctacaa atgcgaatgg taatgctcgt    6000
ataaaagagt ttaaggaaat ggttctttca ctccatcgtg aacacattgg ggttaacatg    6060
gatgttgtct ataatcatac ctttgccacg caaatctctg acttcgataa aattgtacca    6120
gaatattatt accgtacgga tgatgcaggt aattatacca acggatcagg tactggaaat    6180
gaaattgcag ccgaaaggcc aatggttcaa aaatttatta ttgattccct taagtattgg    6240
gtcaatgagt atcatattga cggcttccgt tttgacttaa tggcgctgct tggaaaagac    6300
acgatgtcca aagctgcctc ggagcttcat gctattaatc aggaattgc actttacggt     6360
gagccatgga cgggtggaac ctctgcactg ccagatgatc agcttctgac aaaaggagct    6420
caaaaaggca tgggagtagc ggtgtttaat gacaatttac gaaacgcgtt ggacggcaat    6480
gtctttgatt cttccgctca aggttttgcg acaggtgcaa caggcttaac tgatgcaatt    6540
aagaatggcg ttgaggggag tattaatgac tttacctctt caccaggtga gacaattaac    6600
tatgtcacaa gtcatgataa ctacacccctt tgggacaaaa tagccctaag caatcctaat   6660
gattccgaag cggatcggat taaaatggaa gaactcgcac aagcagttgt tatgacctca    6720
caaggcgttc cattcatgca aggcggggaa gaaatgcttc gtacaaaagg cggcaacgac    6780
aatagttata atgcaggcga tgcggtcaat gagtttgatt ggagcaggaa agctcaatat    6840
ccagatgttt tcaactatta tagcgggcta atccacttc gtcttgatca cccagccttc     6900
cgcatgacga cagctaatga aatcaatagc cacctccaat tcctaaatag tccagagaac    6960
acagtggcct atgaattaac tgatcatgtt aataaagaca atggggaaa tatcattgtt     7020
gtttataacc caaataaaac tgtagcaacc atcaatttgc cgagcgggaa atgggcaatc    7080
aatgctacga gcgtaaggt aggagaatcc acccttggtc aagcagaggg aagtgtccaa     7140
gtaccaggta tatctatgat gatccttcat caagaggtaa gcccagacca cggtaaaaag    7200
taaaagagca gagaggacgg atttcctgaa ggaaatccgt ttttttattt tcaagcacga    7260
aaaacacttc ccggtgatcg ggaggtgttt tttgttaaaa agatcatgac atgcatagaa    7320
cagcgaccgg gctaattgta tataatattg tgaatttaac aaaaaattta caaggagat    7380
gataaaggca atgaccaggg tgaaaaggat gagatttgct gatttgttgg atttagaggc    7440
ggagtagatg aaaccggcca aagtatccct actccaccga ttgctccagt gcctgaagca    7500
atgtgttgat tgtaacacag taaatcgttt tacagcaata acatttttg tgaatatttt     7560
attgatttcg gctgtgatct cattcccata ttctgctgcg gcccatggcg caacacagtc    7620
cggcgatcaa tattcaagct ttgaagaatt ggagcggaat gaagatccag cttcttaccg    7680
aattacggag aagaacgcaa gagtgccgat gctcatcatg gccatccatg gaggcggcat    7740
cgaacccgga acgagcgaaa tcgccaatga agtgtccaaa aactattccc tgtacttgtt    7800
tgaagggctg aaatcatcag gcaatacgga ccttcacatt acaagcacgc gttttgacga    7860
gccagcggcg ctcgcaatta ctgcaagcca ccagtatgtc atgtcgctcc acggctatta    7920
cagtgaagac cgcgatatta agtaggcgg cacagaccgc gctaaaatca gaatattggt     7980
tgatgagctg aaccgctcgg ggtttgccgc tgaaatgctg gggacagatg acaagtatgc    8040
cggaacccat ccgaataaca tcgccaacaa gtcgctttcc gggctgagca ttcagcttga    8100
aatgagcacg ggtttccgca aatctttatt cgaccggttt acactaaaag acagggcggc    8160
gacgcaaaac gaaacgtttt accgatttac aaagctgctg acagatttta ttcatgaaaa    8220
ctatgaagaa gacggagggg atttcccctc tgcaaaaata aaacacccc ttcaagtgaa     8280
```

```
aaaggaggtg tttcggcggt tgtgttaacc gttggactct gaggtgccgc cgccggtgaa    8340
tacggaaacg atggcgttcc acagagacac aaagaagtcg atcagttttt gaagaaagtt    8400
ttgtccttct tcagaatcca agaatttcgt gattttatcc tttgctttgt caagctggtc    8460
tccaacctgg ttccagtcga tattaatatt tttcatgtta ttaaataaag atataagaga    8520 gttttttctga tcttctgtga gtgtcacgcc aagttcggaa gcagccgaat caatcgtttt    8580
ctccaattcc tcttttgact cgggaactcc gttttttcgag atttcttcct tgactttggc    8640
catcagcgct gacgcgtttt cactgccgat tttctcgcca agctctgaag tggtgacaag    8700
ctcttcattc gcgaccttt tcacatcttc ggaattttt tcgcccgaag tcgtttcata    8760
cgctttcatc aatccggtta aagcggctgt gcctgacact caaacggag cggtgacata    8820 gactttggcg tcttttacac cggccgtcat cagcgcgttc aaatacatct catctgtaat    8880
tctgctgata ttgtgtgtct gaacttccaa accggtgcct ttttttcgcta cggtaattga    8940 agaagaagaa atcgctcttg ttccgatttg tgctttcggt atataatccc ctaaatattt    9000
atgctcctca tcatttgtca cctcgatgat ggtcgcattt tcaggcgcat tcatttcttt    9060
taatactttt tgtctgtcct ggcttgacaa gtctttcccc agcgtgacga tgacatcacc    9120
cactgcggcg tcagcgaagc tgacctgcgg gaaaatgagc agacacaatg ctgtaaagat    9180
tcctagtatc gattttttca agctcaatgc cctccttaaa aatgcaggct tcaggcagaa    9240
ttgctgtact tttaaagaag cctgccggaa cggaaataat gcgttccgaa atatagacgg    9300
atgaaagatg agtgaggttt caaagaaaaa aagagagaat tttctcttca agtcaaatgc    9360
cctcccggca tcgtatctcg ccgctctttt atcattcatg atttttcacag gcgattcaac    9420 ctttttttaa aatttttac aaaaacgata caagagcggc gtttatttcg gtcgattggc    9480
tctctgcttc ttcaatatga tataatgacc cttgtgaaat gaaggagag aatcaagatg    9540 gctaaaaaag gatacataca actgacaaac ggcaaaaaaa tcgagtttga actatatccg    9600
gatgcggcgc cgggaactgt cgccaacttt gaaaaacttg caaacgaagg gttctatgac    9660
gggctgaagt tccaccgcgt catccccggc ttcgtcagcc agggaggctg cccgcacggc    9720
accggaacag gcggacctgg atatacgatt aaatgcgaga cagaagggaa tccgcacaaa    9780
cacgaagccg gttctctctc aatggctcac gcaggaaaag ataccggagg cagccaattt    9840
tttatcgtcc atgagcctca gccgcacttg aacggcgttc acaccgtttt cggaaaggtc    9900
acatcaggcc ttgatgccgt cacttcaatg gagcagggac aaggcatgga aaaagtcgaa    9960
gtatttgatg cataatcaga gagcgcaaaa acagcccgc ttagccgggc tgttttttg    10020 tctgtaacgg tgtttatttt ccaggtgcaa caggacttga ggccgattct tcgtccacat    10080
cctgatagga aataacgatg ctaataaata aaataattgt gaaaaatga ccctttatgt    10140 aaaatatatt caagtgaaga gctagataga gaacgcaatc tgtaaaaaag gaagggcgt    10200 aaggggtgag cgtaaaaatc ccatcgacgg cagtcggcgt aaaaattaat gactggtata    10260
acgcgatacg                                                          10270
```

<210> SEQ ID NO 82
<211> LENGTH: 74
<212> TYPE: DNA
<213> ORGANISM: Bacillus licheniformis

<400> SEQUENCE: 82

```
gcttttcttt tggaagaaaa tatagggaaa atggtacttg ttaaaaattc ggaatattta      60
```

```
tacaatatca tatg                                                      74

<210> SEQ ID NO 83
<211> LENGTH: 74
<212> TYPE: DNA
<213> ORGANISM: Artificial Sequence
<220> FEATURE:
<223> OTHER INFORMATION: synthetic

<400> SEQUENCE: 83
gcttttcttt tggaagaaaa tatagggaaa atggtacttg ttaaaaattc ggaatattta    60
tacaatatca ttgt                                                      74

<210> SEQ ID NO 84
<211> LENGTH: 26
<212> TYPE: DNA
<213> ORGANISM: Bacillus licheniformis

<400> SEQUENCE: 84
tttcacattg aaagggagg agaatc                                          26

<210> SEQ ID NO 85
<211> LENGTH: 58
<212> TYPE: DNA
<213> ORGANISM: Bacillus subtilis

<400> SEQUENCE: 85
acagaatagt cttttaagta agtctactct gaattttttt aaaaggagag ggtaaaga      58
```

PROMOTER SEQUENCES AND METHODS THEREOF FOR ENHANCED PROTEIN PRODUCTION IN *BACILLUS* CELLS

FIELD

The present disclosure is generally related to the fields of bacteriology, microbiology, molecular biology, genetics, enzymology, industrial protein production and the like. More particularly, certain embodiments of the disclosure are related to novel promoter sequences and methods thereof for obtaining enhanced protein production phenotypes in *Bacillus* sp. (host) cells. As set forth herein, the novel promoter sequences of the disclosure, when operably linked to a gene (or open reading frame) encoding a protein of interest, are particularly well suited for use in large scale production of industrially relevant proteins.

CROSS-REFERENCE TO RELATED APPLICATIONS

The present application is a U.S. National Stage Application under 35 U.S.C. § 371 of International Application No. PCT/US2019/062955, filed Nov. 25, 2019, which claims priority to U.S. Provisional Patent Application No. 62/772,363, filed Nov. 28, 2018, all of which are incorporated herein by reference in their entirety.

REFERENCE TO A SEQUENCE LISTING

The contents of the electronic submission of the text file Sequence Listing, named "NB41318-WO-PCT_Sequence-Listing.txt" was created on Nov. 21, 2019 and is 176 KB in size, which is hereby incorporated by reference in its entirety.

BACKGROUND

Gram-positive bacteria such as *Bacillus subtilis, B. licheniformis, B. amyloliquefaciens* and the like are frequently used as microbial factories for the production of industrial relevant proteins, due to their excellent fermentation properties and high yields (e.g., up to 25 grams per liter culture; Van Dijl and Hecker, 2013). For example, *B. subtilis* is well known for its production of α-amylases (Jensen et al., 2000; Raul et al., 2014) and proteases (Brode et al., 1996) necessary for food, textile, laundry, medical/dental instrument (cleaning), membrane (cleaning), pharmaceutical industries and the like (Westers et al., 2004). Because these non-pathogenic Gram-positive bacteria produce proteins that completely lack toxic by-products (e.g., lipopolysaccharides; LPS, also known as endotoxins) they have obtained the "Qualified Presumption of Safety" (QPS) status of the European Food Safety Authority, and many of their products gained a "Generally Recognized as Safe" (GRAS) status from the US Food and Drug Administration (Olempska-Beer et al., 2006; Earl et al., 2008; Caspers et al., 2010).

Thus, the production of proteins (e.g., enzymes, antibodies, receptors, peptides, etc.) in microbial host cells is of particular interest in the biotechnological arts. Likewise, the optimization of host cells for the production and/or secretion of one or more protein(s) of interest is of high relevance, particularly in the industrial biotechnology setting, wherein small improvements in protein yield are quite significant when the protein is produced in large industrial quantities. More particularly, *B. licheniformis* and *B. subtilis* are exemplary *Bacillus* sp. (host) cells of high industrial importance, and as such, the ability to genetically modify and engineer such host cells for enhanced/increased protein expression/production is highly desirable for construction of new and improved *Bacillus* sp. production strains.

For example, the recombinant production of a protein of interest (e.g., an enzyme) encoded by a gene (or open reading frame; ORF) is generally accomplished by constructing expression cassettes (i.e., constructs/vectors/cassettes suitable for use in a given host cell) in which the polynucleotide (sequence) coding for the protein of interest is placed downstream (3') and operably linked to a promoter (nucleic acid) sequence. Thus, the promoter sequence is placed upstream (5') and operably linked to a gene (or ORF) which is downstream (3') of the promoter sequence (i.e., in operable combination).

Likewise, expression cassettes are introduced into host cells by various techniques (e.g., transformation), wherein the expression/production of the desired protein of interest (POI) may be achieved by cultivating the (transformed) host cell under suitable conditions necessary for the expression/production of the POI. For example, International PCT Publication No. WO2013/086219, generally discloses promoters, expression vectors, microorganisms, and methods for the production of polynucleotides coding for proteins of interest comprising ribosomal promoters derived from *B. subtilis*.

While numerous promoters for use in the expression of genes in host cells are generally known, there remain ongoing and unmet needs in the art for novel promoter (nucleic acid) sequences. More particularly, such ongoing and unmet needs include, but are not limited to, the identification of novel promoter (nucleic acid) sequences, enhanced promoter functionalities thereof, increased promoter activities thereof, enhanced protein production phenotypes and the like. As presented, described and exemplified hereinafter, the instant disclosure is related to such highly desirable and unmet needs of obtaining novel promoter sequences and constructing *Bacillus* sp. host cells thereof (e.g., protein production (host) cells, cell factories) comprising enhanced protein production phenotypes and the like.

SUMMARY

The instant disclosure is generally related to compositions and methods for producing and constructing *Bacillus* sp. cells (e.g., protein production host cells, cell factories) having increased protein production phenotypes, and the like. More particularly, certain embodiments of the disclosure are related to novel promoter (nucleic acid) sequences, expression cassettes comprising such novel promoters and modified *Bacillus* sp. (daughter) cells thereof comprising enhanced protein productivity phenotypes.

Thus, certain embodiments of the disclosure are related promoter nucleic acid sequences. In certain embodiments, a promoter nucleic acid sequence comprises at least 90% sequence identity to SEQ ID NO: 39 and comprising at least one mutation selected from the group consisting of a thymine (T) at nucleotide position 30 of SEQ ID NO: 39, a thymine (T) at nucleotide position 89 of SEQ ID NO: 39, a guanine (G) at nucleotide position 90 of SEQ ID NO: 39 and a thymine (T) at nucleotide position 91 of SEQ ID NO: 39. In other embodiments, a promoter nucleic acid sequence of the disclosure comprises at least two mutations selected from the group consisting a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39. In other embodiments, a promoter nucleic acid sequence comprises at least three mutations selected from the group consisting a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39. In certain other embodiments, a promoter nucleic acid sequence comprises at least four mutations comprising a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39. In other embodiments, a promoter nucleic acid sequence comprises SEQ ID NO: 40. In other embodiments, a promoter nucleic acid sequence of the disclosure comprises a gene or open reading frame (ORF) encoding a protein of interest (POI) positioned downstream (3') and operably linked to the promoter. In certain embodiments, protein of interest (POI) is an enzyme. In other embodiments, the enzyme is a hydrolase. In yet other embodiments, the promoter sequence comprises one or more nucleotides upstream (5') and operably linked thereto. In certain embodiments, the promoter sequence is operably linked to a (3') downstream native aprE 5'-UTR sequence, or a modified aprE 5'-UTR sequence thereof. In certain embodiments, the native aprE 5'-UTR sequence comprises SEQ ID NO: 85.

Thus, certain other embodiments of the disclosure are related are a promoter nucleic acid sequence comprising SEQ ID NO: 40, SEQ ID NO: 58 or SEQ ID NO: 59. In particular embodiments, a promoter nucleic acid sequence comprising SEQ ID NO: 40, SEQ ID NO: 58 or SEQ ID NO: 59 further comprises a gene or ORF encoding a protein of interest (POI) positioned (3') downstream and operably linked to the promoter. In certain embodiments, the POI is an enzyme. In other embodiments, the enzyme is a hydrolase. In another embodiment, a promoter nucleic acid sequence comprising SEQ ID NO: 40, SEQ ID NO: 58 or SEQ ID NO: 59 further comprises one or more nucleotides upstream (5') and operably linked thereto. In another embodiment, a promoter nucleic acid sequence comprising SEQ ID NO: 40, SEQ ID NO: 58 or SEQ ID NO: 59 is operably linked to a (3') downstream native aprE 5'-UTR sequence, or a modified aprE 5'-UTR sequence thereof. In another embodiment, the native aprE 5'-UTR sequence comprises SEQ ID NO: 85.

Certain other embodiments of the disclosure are directed to a polynucleotide sequence which hybridizes under stringent hybridization conditions with SEQ ID NO: 60, wherein the polynucleotide sequence which hybridizes comprises at least one mutation at nucleotide position selected from 30, 89, 90 or 91, relative to equivalent nucleotide positions 30, 89, 90 or 91 of SEQ ID NO: 39. In certain embodiments, a polynucleotide sequence which hybridizes under stringent hybridization conditions comprises SEQ ID NO: 40. In another embodiment, a polynucleotide sequence which hybridizes under stringent hybridization conditions comprises SEQ ID NO: 58. In other embodiments, a polynucleotide sequence which hybridizes under stringent hybridization conditions comprises SEQ ID NO: 59. In certain other embodiments, a polynucleotide sequence which hybridizes under stringent hybridization conditions with SEQ ID NO: 60 further comprises a gene or ORF encoding a protein of interest (POI) positioned downstream (3') and operably linked to the promoter. In certain embodiments, the POI is an enzyme. In other embodiments, the enzyme is a hydrolase. In other embodiments, the polynucleotide further comprises one or more nucleotides upstream (5') and operably linked thereto. In certain other embodiments, a polynucleotide sequence which hybridizes under stringent hybridization conditions with SEQ ID NO: 60 is operably linked to a (3') downstream native aprE 5'-UTR sequence, or a modified aprE 5'-UTR sequence thereof. In particular embodiments, a native aprE 5'-UTR sequence comprises SEQ ID NO: 85.

Thus, certain other embodiments are related to genetically modified *Bacillus* sp. cells comprising a novel promoter sequence disclosed herein. Certain other embodiments are related to genetically modified *Bacillus* sp. cells comprising a novel polynucleotide sequence disclosed herein. Other embodiments relate to an expression cassette comprising a novel promoter of the disclosure, or an expression cassette comprising a novel polynucleotide of the disclosure. Yet other embodiments relate to modified *Bacillus* sp. cells comprising an expression cassette of the disclosure.

Thus, certain other embodiments are related to a mutant *B. subtilis* cell comprising a promoter nucleic acid sequence which hybridizes under stringent hybridization conditions with SEQ ID NO: 60, wherein the mutant promoter sequence comprises at least one mutation at nucleotide position selected from 30, 89, 90 or 91, relative to equivalent nucleotide positions 30, 89, 90 or 91 of SEQ ID NO: 39.

In other embodiments, the disclosure is related to a promoter region nucleic acid sequence comprising an (5') upstream promoter sequence operably linked to a (3') downstream 5'-UTR sequence, wherein the promoter sequence comprises at least 90% sequence identity to SEQ ID NO: 82 and comprises a thymine (T) at nucleotide position 72 of SEQ ID NO: 82, a guanine (G) at nucleotide position 73 of SEQ ID NO: 82 and a thymine (T) at nucleotide position 74 of SEQ ID NO: 82. In certain embodiments, the promoter region nucleic acid sequence comprise a native 5'-UTR sequence or a modified 5'-UTR sequence. In certain embodiments, the 5'-UTR sequence is a native amyL 5'-UTR sequence of SEQ ID NO: 84, or a variant amyL 5'-UTR sequence thereof. In another embodiment, the promoter region nucleic acid sequence comprises a native aprE 5'-UTR sequence of SEQ ID NO: 85, or a variant aprE 5'-UTR sequence thereof.

Thus, other embodiments are directed to a promoter region nucleic acid sequence comprising SEQ ID NO: 65. Another embodiment is directed to a promoter region nucleic acid sequence comprising SEQ ID NO: 67. In another embodiment, a promoter region nucleic acid sequence comprising SEQ ID NO: 65 further comprises a gene or open reading frame (ORF) encoding a protein of interest (POI) positioned downstream (3') and operably linked to the promoter region. In certain embodiments, the POI is an enzyme. In another embodiment, the enzyme is a hydrolase. In other embodiments, the promoter region sequence further comprises one or more nucleotides upstream (5') and operably linked thereto.

In certain other embodiments, the disclosure is related to a modified *B. licheniformis* amyL promoter derived from a native *B. licheniformis* amyL promoter comprising a nucleotide sequence of SEQ ID NO: 82, wherein the modified promoter comprises at least 90% sequence identity to SEQ ID NO: 82 and comprises a thymine (T) at nucleotide position 72 of SEQ ID NO: 82, a guanine (G) at nucleotide position 73 of SEQ ID NO: 82 and a thymine (T) at nucleotide position 74 of SEQ ID NO: 82. In another embodiment, the modified amyL promoter comprises a gene or open reading frame (ORF) encoding a protein of interest (POI) positioned downstream (3') and operably linked to the promoter. In a particular embodiment, the POI is an enzyme.

In other embodiments the enzyme is a hydrolase. In another embodiment, the promoter further comprises one or more nucleotides upstream (5') and operably linked thereto.

Thus, certain other embodiments are related to a polynucleotide sequence which hybridizes under stringent hybridization conditions with a polynucleotide sequence of SEQ ID NO: 65, or the complimentary sequence thereof. Other embodiments are therefore related to a polynucleotide sequence which hybridizes under stringent hybridization conditions with SEQ ID NO: 67, or the complimentary sequence thereof. Another embodiment is related to a polynucleotide sequence which hybridizes under stringent hybridization conditions with SEQ ID NO: 83, or the complimentary sequence thereof.

Other embodiments are related to modified *Bacillus* sp. cells comprising a novel promoter region of the disclosure.

Certain embodiments are related to a modified *Bacillus* sp. cell comprising a modified promoter of SEQ ID NO: 83.

Certain other embodiments are therefore related to an expression cassette comprising a novel promoter region of the disclosure. In certain embodiments, an expression cassette comprises a modified *B. licheniformis* amyL promoter.

Thus, certain other embodiments of the disclosure are directed to methods for enhanced protein production in a modified *Bacillus* sp. cell comprising (a) introducing a polynucleotide expression cassette into a parental *Bacillus* sp. cell, wherein the cassette comprises a promoter sequence positioned upstream (5') and operably linked to a gene or open reading frame (ORF) encoding a protein of interest (POI), wherein the promoter comprises at least 90% identity to SEQ ID NO: 39 and comprises at least one modification selected from the group consisting of a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39, (b) isolating a modified cell from step (a) comprising the introduced expression construct, and (c) fermenting the modified cell of step (b) under suitable conditions for the production of the POI, wherein the modified cell of step (c) produces an increased amount of the POI relative to an equivalent *Bacillus* sp. cell comprising a polynucleotide expression cassette comprising a promoter sequence positioned upstream (5') and operably linked to the same gene or ORF encoding the same POI, wherein the promoter comprises SEQ ID NO: 39. In certain embodiments, the promoter comprises at least two mutations selected from the group consisting a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39. In other embodiments, the promoter comprises at least three mutations selected from the group consisting a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39. In another embodiment, the promoter comprises at least four mutations comprising a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39. In other embodiments of the methods, the POI is an enzyme. In another embodiment of the methods, the enzyme is a hydrolase. In another embodiment of the methods, the promoter further comprising one or more nucleotides upstream (5') and operably linked thereto. In certain embodiments, the promoter sequence is operably linked to a (3') downstream native aprE 5'-UTR sequence, or a modified aprE 5'-UTR sequence thereof. In other embodiments of the methods, the native aprE 5'-UTR sequence comprises SEQ ID NO: 85.

Certain other embodiments of the disclosure are related to methods for enhanced protein production in a modified *Bacillus* sp. cell comprising (a) introducing a polynucleotide expression cassette into a parental *Bacillus* sp. cell, wherein the cassette comprises an upstream promoter region comprising at least 90% sequence identity to SEQ ID NO: 65 and having a thymine (T) at nucleotide position 72 of SEQ ID NO: 65, a guanine (G) at nucleotide position 73 of SEQ ID NO: 65 and a thymine (T) at nucleotide position 74 of SEQ ID NO: 65, wherein the upstream promoter region is operably linked to a gene or open reading frame (ORF) encoding a protein of interest (POI), (b) isolating a modified cell from step (a) comprising the introduced expression cassette, and (c) fermenting the modified cell of step (b) under suitable conditions for the production of the POI, wherein the modified cell of step (c) produces an increased amount of the POI relative to an equivalent *Bacillus* sp. cell comprising an introduced polynucleotide expression cassette comprising an upstream promoter region comprising at least 90% sequence identity to SEQ ID NO: 65 and having an adenine (A) at nucleotide position 72 of SEQ ID NO: 65, a thymine (T) at nucleotide position 73 of SEQ ID NO: 65 and a guanine (G) at nucleotide position 74 of SEQ ID NO: 65, wherein the upstream promoter region is operably linked to the same gene or ORF encoding the same POI. In certain embodiments of the methods, the POI is an enzyme. In other embodiments the enzyme is a hydrolase.

In another embodiment, the disclosure is related to methods for enhanced protein production in a modified *Bacillus* sp. cell comprising (a) introducing a polynucleotide expression cassette into a parental *Bacillus* sp. cell, wherein the cassette comprises an upstream promoter region comprising at least 90% sequence identity to SEQ ID NO: 67 and having a thymine (T) at nucleotide position 72 of SEQ ID NO: 65, a guanine (G) at nucleotide position 73 of SEQ ID NO: 65 and a thymine (T) at nucleotide position 74 of SEQ ID NO: 65, wherein the upstream promoter region is operably linked to a gene or open reading frame (ORF) encoding a protein of interest (POI), (b) isolating a modified cell from step (a) comprising the introduced expression cassette, and (c) fermenting the modified cell of step (b) under suitable conditions for the production of the POI, wherein the modified cell of step (c) produces an increased amount of the POI relative to an equivalent *Bacillus* sp. cell comprising an introduced polynucleotide expression cassette comprising an upstream promoter region comprising at least 90% sequence identity to SEQ ID NO: 67 and having an adenine (A) at nucleotide position 72 of SEQ ID NO: 65, a thymine (T) at nucleotide position 73 of SEQ ID NO: 65 and a guanine (G) at nucleotide position 74 of SEQ ID NO: 65, wherein the upstream promoter region is operably linked to the same gene or ORF encoding the same POI. In certain embodiments of the methods, the POI is an enzyme. In other embodiments the enzyme is a hydrolase.

In another embodiment, the disclosure is related to methods for enhanced protein production in a modified *Bacillus* sp. cell comprising (a) introducing a polynucleotide expression cassette into a parental *Bacillus* sp. cell, wherein the cassette comprises an upstream promoter comprising at least 90% sequence identity to SEQ ID NO: 83 and having a thymine (T) at nucleotide position 72 of SEQ ID NO: 83, a guanine (G) at nucleotide position 73 of SEQ ID NO: 83 and a thymine (T) at nucleotide position 74 of SEQ ID NO: 83, wherein the upstream promoter is operably linked to a gene or open reading frame (ORF) encoding a protein of interest (POI), (b) isolating a modified cell from step (a) comprising the introduced expression cassette, and (c) fermenting the modified cell of step (b) under suitable conditions for the production of the POI, wherein the modified cell of step (c) produces an increased amount of the POI relative to an equivalent *Bacillus* sp. cell comprising an introduced polynucleotide expression cassette comprising an upstream promoter comprising at least 90% sequence identity to SEQ ID NO: 83 and having an adenine (A) at nucleotide position 72 of SEQ ID NO: 83, a thymine (T) at nucleotide position 73 of SEQ ID NO: 83 and a guanine (G) at nucleotide position 74 of SEQ ID NO: 83, wherein the upstream promoter is operably linked to the same gene or ORF encoding the same POI. In certain embodiments of the methods, the POI is an enzyme. In other embodiments the enzyme is a hydrolase.

BRIEF DESCRIPTION OF DRAWINGS

FIG. 1 presents nucleic acid sequence alignments of a native *B. subtilis* rrnIp2 promoter (SEQ ID NO: 39), a novel (synthetic) rrnIp2-1 promoter (SEQ IDNO: 40), a novel (synthetic) rrnIp2-2 promoter (SEQ IDNO: 58) and a novel (synthetic) rrnIp2-3 promoter (SEQ IDNO: 59). As shown in FIG. 1, the -35 and -10 promoter sequence regions are indicated with underlined nucleotides, the putative transcription start site (TSS) is indicated with bold underlined nucleotides, with a double-underlined "G" nucleotide to assist in visualizing the TSS.

FIG. 2 presents the native rrnIp2 promoter (SEQ ID NO: 39) and its complimentary sequence (SEQ ID NO: 60; FIG. 2A), the synthetic rrnIp2-1 promoter (SEQ ID NO: 40) and its complimentary sequence (SEQ ID NO: 61; FIG. 2B), the synthetic rrnIp2-2 promoter (SEQ ID NO: 58) and its complimentary sequence (SEQ ID NO: 62; FIG. 2C) and the rrnIp2-3 promoter (SEQ ID NO: 59) and its complimentary sequence (SEQ ID NO: 63; FIG. 2D).

FIG. 3 presents nucleic acid sequence alignments of a native *B. licheniformis* amyL promoter region (PamyL-1; SEQ ID NO: 64) and a novel (synthetic) amyL promoter region (PamyL-2; SEQ ID NO: 65). As shown in FIG. 3, the -35 and -10 promoter sequence regions are indicated with underlined nucleotides, the 5'-UTR sequence is indicated with italicized nucleotides, and the putative transcription start site (TSS) is indicated with bold nucleotides and a double-underlined "G" nucleotide to assist in visualizing the TSS of PamyL-1 relative to PamyL-2.

FIG. 4 shows an alignment of the native *B. licheniformis* amyL promoter sequence (SEQ ID NO: 82) and the synthetic amyL promoter sequence (SEQ ID NO: 83), wherein the putative transcription start-site (TSS) is indicated with bold nucleotides and an underlined "G" nucleotide to assist in visualizing the TSS of native amyL promoter relative to the synthetic amyL promoter.

FIG. 5 presents nucleic acid sequence alignments of a synthetic PamyL-3 promoter region (SEQ ID NO: 66) and synthetic Pamyl-4 promoter region (SEQ ID NO: 67). As shown in FIG. 5, the putative transcription start-site (TSS) is indicated with bold nucleotides followed by the 5'-UTR sequence indicated with italicized nucleotides and a double-underlined "G" nucleotide to assist in visualizing the TSS of PamyL-3 relative to PamyL-4.

BRIEF DESCRIPTION OF THE BIOLOGICAL SEQUENCES

SEQ ID NO: 1 is a synthetic nucleic acid sequence encoding a Cas9 protein.

SEQ ID NO: 2 is an amino acid sequence of an N-terminal Nuclear Localization Signal (NLS) sequence.

SEQ ID NO: 3 is an amino acid sequence of a C-terminal NLS sequence.

SEQ ID NO: 4 is an amino acid sequence comprising a deca-histidine (10-H) tag.

SEQ ID NO: 5 is a nucleic acid sequence comprising a *B. subtilis* aprE promoter.

SEQ ID NO: 6 is an Cas9 forward primer nucleic acid sequence.

SEQ ID NO: 7 is an Cas9 reverse primer nucleic acid sequence.

SEQ ID NO: 8 is a nucleic acid sequence of plasmid pKB320 backbone.

SEQ ID NO: 9 is a nucleic acid sequence of plasmid pKB320.

SEQ ID NO: 10 is a pKB320 forward primer nucleic acid sequence.

SEQ ID NO: 11 is a pKB320 reverse primer nucleic acid sequence.

SEQ ID NO: 12 is a Cas9 "reverse sequencing primer 1" nucleic acid sequence.

SEQ ID NO: 13 is a Cas9 "reverse sequencing primer 2" nucleic acid sequence.

SEQ ID NO: 14 is a Cas9 "forward sequencing primer 1" nucleic acid sequence.

SEQ ID NO: 15 is a Cas9 "forward sequencing primer 2" nucleic acid sequence.

SEQ ID NO: 16 is a Cas9 "forward sequencing primer 3" nucleic acid sequence.

SEQ ID NO: 17 is a Cas9 "forward sequencing primer 4" nucleic acid sequence.

SEQ ID NO: 18 is a Cas9 "forward sequencing primer 5" nucleic acid sequence.

SEQ ID NO: 19 is a Cas9 "forward sequencing primer 6" nucleic acid sequence.

SEQ ID NO: 20 is a Cas9 "forward sequencing primer 7" nucleic acid sequence.

SEQ ID NO: 21 is a synthetic pRF694 nucleic acid sequence.

SEQ ID NO: 22 is a synthetic pRF748 nucleic acid sequence.

SEQ ID NO: 23 is a synthetic double terminator nucleic acid sequence.

SEQ ID NO: 24 is an *E. coli* rpsL promoter (nucleic acid) sequence.

SEQ ID NO: 25 is a synthetic nucleic acid sequence encoding Cas9 endonuclease recognition domain.

SEQ ID NO: 26 is a lambda phage t0 terminator nucleic acid sequence.

SEQ ID NO: 27 is a *B. subtilis* yhfN gene.

SEQ ID NO: 28 is a *B. subtilis* yhfN target site.

SEQ ID NO: 29 is a synthetic nucleic acid encoding a yhfN VT domain.

SEQ ID NO: 30 is a *B. subtilis* yhfN target site PAM sequence.

SEQ ID NO: 31 is a synthetic yhfN guide RNA (gRNA) sequence.

SEQ ID NO: 32 is a synthetic polynucleotide sequence (DNA) encoding yhfN gRNA.

SEQ ID NO: 33 is a synthetic yhfN gRNA polynucleotide (DNA) expression cassette.

SEQ ID NO: 34 is a synthetic pRF793 nucleic acid sequence.

SEQ ID NO: 35 is a polynucleotide sequence comprising a *B. subtilis* yhfN locus.

SEQ ID NO: 36 is a synthetic pRF748 forward primer sequence.

SEQ ID NO: 37 is a synthetic pRF748 reverse primer sequence

SEQ ID NO: 38 is a *B. subtilis* nucleic acid (sequence) flanking region 5' of the yhfN gene locus.

SEQ ID NO: 39 is a native *B. subtilis* rrnIp2 promoter nucleic acid sequence.

SEQ ID NO: 40 is a synthetic rrnIp2-1 promoter nucleic acid sequence.

SEQ ID NO: 41 is a synthetic *B. amyloliquefaciens* apr terminator sequence.

SEQ ID NO: 42 is a *B. subtilis* nucleic acid (sequence) flanking region 3' of the yhfN gene locus.

SEQ ID NO: 43 is a *B. subtilis* comK gene.

SEQ ID NO: 44 is a synthetic rrnIp2_α-amylase cassette.

SEQ ID NO: 45 is a synthetic rrnIp2-1_α-amylase cassette.

SEQ ID NO: 46 is a *B. licheniformis* 5' lysA homology arm.

SEQ ID NO: 47 is a synthetic modified aprE 5' UTR.

SEQ ID NO: 48 is a *B. licheniformis* lat signal sequence.

SEQ ID NO: 49 is a synthetic DNA sequence encoding a variant *Cytophaga* sp. α-amylase.

SEQ ID NO: 50 is a *B. licheniformis* lat terminator sequence.

SEQ ID NO: 51 is a *B. licheniformis* 3' lysA homology arm.

SEQ ID NO: 52 is a synthetic lysA forward primer.

SEQ ID NO: 53 is a synthetic lysA reverse primer.

SEQ ID NO: 54 is synthetic DNA 1032.

SEQ ID NO: 55 is synthetic DNA 1033.

SEQ ID NO: 56 is synthetic DNA 1034.

SEQ ID NO: 57 is synthetic DNA 1035.

SEQ ID NO: 58 is a synthetic rrnIp2-2 promoter sequence.

SEQ ID NO: 59 is a synthetic rrnIp2-3 promoter sequence.

SEQ ID NO: 60 is a complimentary sequence of the native rrnIp2 promoter sequence (SEQ ID NO: 39).

SEQ ID NO: 61 is a complimentary sequence of the synthetic rrnIp2-1 promoter sequence (SEQ ID NO: 40).

SEQ ID NO: 62 is a complimentary sequence of the synthetic rrnIp2-2 promoter sequence (SEQ ID NO: 58).

SEQ ID NO: 63 is a complimentary sequence of the synthetic rrnIp2-3 promoter sequence (SEQ ID NO: 59).

SEQ ID NO: 64 is a native *B. licheniformis* amyL promoter region herein named PamyL-1, comprising a native *B. licheniformis* amyL promoter sequence (SEQ ID NO: 82) and a native *B. licheniformis* amyL 5'-UTR sequence (SEQ ID NO: 84).

SEQ ID NO: 65 is a synthetic amyL promoter region herein named PamyL-2, comprising a synthetic amyL promoter sequence (SEQ ID NO: 83) operably linked to a native *B. licheniformis* amyL 5'-UTR sequence (SEQ ID NO: 84).

SEQ ID NO: 66 is a synthetic amyL promoter region herein named PamyL-3, comprising a native *B. licheniformis* amyL promoter sequence (SEQ ID NO: 82) operably linked to a native *B. subtilis* aprE 5'-UTR sequence (SEQ ID NO: 85).

SEQ ID NO: 67 is a synthetic amyL promoter region herein named PamyL-4, comprising a synthetic amyL promoter sequence (SEQ ID NO: 83) operably linked to a native *B. subtilis* aprE 5'-UTR sequence (SEQ ID NO: 85).

SEQ ID NO: 68 is a native DNA sequence encoding a mature and truncated *B. deramificans* pullulanase.

SEQ ID NO: 69 is a synthetic primer sequence.

SEQ ID NO: 70 is a synthetic primer sequence.

SEQ ID NO: 71 is a synthetic primer sequence.

SEQ ID NO: 72 is a synthetic primer sequence.

SEQ ID NO: 73 is a synthetic primer sequence.

SEQ ID NO: 74 is a synthetic primer sequence.

SEQ ID NO: 75 is a synthetic primer sequence.

SEQ ID NO: 76 is a synthetic primer sequence.

SEQ ID NO: 77 is a synthetic primer sequence.

SEQ ID NO: 78 is a PamyL-1_pullulnase expression cassette.

SEQ ID NO: 79 is a PamyL-2_pullulnase expression cassette.

SEQ ID NO: 80 is a PamyL-3_pullulnase expression cassette

SEQ ID NO: 81 is a PamyL-4_pullulnase expression cassette

SEQ ID NO: 82 is a native *B. licheniformis* amyL promoter sequence.

SEQ ID NO: 83 is a synthetic amyL promoter sequence.

SEQ ID NO: 84 is a native *B. licheniformis* amyL 5'-UTR sequence.

SEQ ID NO: 85 is native *B. subtilis* aprE 5'-UTR sequence.

DETAILED DESCRIPTION

The instant disclosure is generally related to compositions and methods for constructing/producing *Bacillus* sp. (host) cells (e.g., protein production host cells, cell factories) having enhanced protein productivity phenotypes and the like. More particularly, certain embodiments of the disclosure are related to novel promoter (nucleic acid) sequences, novel expression constructs thereof, modified *Bacillus* (daughter) cells and the like.

Thus, certain embodiments of the disclosure are related to modified (or mutant) *Bacillus* sp. cells. Other embodiments are related to modified *Bacillus* sp. cells comprising one or more novel promoter (nucleic acid) sequences introduced therein (e.g., a "modified" or "synthetic" promoter sequence). In other embodiments, the one or more promoter sequences are operably linked to a gene or an open reading frame encoding a protein of interest. In other embodiments, a modified *Bacillus* sp. (daughter) cell of the disclosure comprises an enhanced protein productivity phenotype relative to a (parental) *Bacillus* sp. cell from which it was derived. Certain other embodiments are related to parental *Bacillus* sp. cell comprising an endogenous (native) promoter (nucleic acid) sequence, wherein a modified *Bacillus* sp. daughter cell derived therefrom comprises a modified (non-native) promoter sequence thereof.

I. Definitions

In view of the modified cells producing one or more heterologous and/or endogenous proteins of interest, and methods thereof described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein, "host cell" refers to a cell that has the capacity to act as a host or expression vehicle for a newly introduced DNA sequence. Thus, in certain embodiments of the disclosure, the host cells are for example *Bacillus* sp. cells or *E. coli* cells.

As defined herein, a "parental cell" or a "parental (host) cell" may be used interchangeably and refer to "unmodified" cells.

As used herein, a "modified cell" or a "modified (host) cell" may be used interchangeably and refer to recombinant (host) cells that comprise at least one genetic modification which is not present in the "parental" host cell from which the modified cells are derived.

In certain embodiments, a parental (un-modified) cell may be referred to as a "control cell", particularly when being compared with, or relative to, a modified daughter cell.

As used herein, when the expression and/or production of a protein of interest (POI) in an parental (un-modified) cell (e.g., a control cell) is being compared to the expression and/or production of the same POI in a modified (daughter) cell, it will be understood that the "modified" and "un-modified" cells are grown/cultivated/fermented under the same conditions (e.g., the same conditions such as media, temperature, pH and the like).

As used herein, the "genus *Bacillus*" or "*Bacillus* sp." cells include all species within the genus "*Bacillus*" as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*".

As used herein, the terms "wild-type" and "native" are used interchangeably and refer to genes, promoters, proteins, protein mixes, cells or strains, as found in nature.

The term "promoter" as used herein generally refers to a nucleic acid sequence capable of controlling the transcription of a coding sequence (or functional RNA). In general, a coding sequence is located downstream (3') to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions and to different levels of RNA transcript produced. Promoters which cause a gene to be expressed in most cell types at most times at similar levels are commonly referred to as "constitutive promoters". It is further recognized that since in most cases the exact boundaries of regulatory sequences have not been completely defined, DNA fragments of different lengths may have identical promoter activity.

As used herein, terms such as "functional promoter" and "promoter function" particularly refer to a nucleic acid sequence capable of controlling the transcription of a coding sequence (or functional RNA) when placed (5') upstream and in operable combination with the coding sequence. For example, promoter function may readily be evaluated, estimated, tested, measured, and the like by means of promoter function/promoter activity assays known by those of skill in the art.

As used herein, the term "promoter activity" refers to a qualitative or a quantitative estimation of promoter function. For example, promoter activity of an unknown (candidate/test) promoter (nucleic acid) sequence may be assessed and compared to the promoter activity of a known (control) promoter sequence (e.g., using one or more promoter activity assays generally known in the art). Such promoter activity measurements/assays may therefore be used to interrogate the rate of expression, temporal expression, spatial expression and the like. Methods to test/measure promoter activity are often based on the expression of a reporter gene (e.g., a green fluorescent protein; GFP), wherein a promoter sequence of interest is placed upstream (5') and operably linked to the reporter gene (e.g., GFP). For example, a promoter sequence of interest (or multiple variants thereof, e.g., comprising one or more mutations, deletions, substitutions) may be tested by operably linking the promoter sequence of interest upstream (5') of the reporter gene (e.g., GFP) and detecting/measuring changes in the reporter gene. Thus, fluorescent reporter genes such as GFP, RFP, and the like allow one of skill in the art to measure promoter activity; e.g., by detection of changes in the fluorescent signal (Solberg and Krauss, 2013).

In certain embodiments of the disclosure, promoter function (or activity) is assessed by the introduction of expression cassettes (constructs) into a suitable host cell (e.g., a *Bacillus* sp. cell). For example, in certain embodiments a suitable host cell comprises either (a) candidate (test) expression cassette or (b) a control expression cassette. More particularly, (a) the candidate (test) expression cassette comprises a candidate (test) promoter sequence positioned upstream (5') and operably linked to an open reading frame (ORF) encoding a protein of interest (e.g., an enzyme) and (b) the control cassette comprises a control promoter sequence positioned upstream (5') and operably linked to an open reading (ORF) encoding the same protein of interest (e.g., the same enzyme). Thus, the control promoter sequence selected for direct comparison with a candidate (test) promoter sequence may be any promoter sequence of known function or activity. In certain embodiments, a control promoter sequence comprises a nucleic acid sequence of SEQ ID NO: 39. For example, in certain embodiments, a suitable host cell of the disclosure comprises either (a) an introduced "control" expression cassette or (b) an introduced "candidate" (test) expression cassette, wherein the two host cells are subsequently cultivated (i.e., under identical conditions) and the amount of the protein of interest expressed/produced directly compared between the two host cells (i.e., candidate vs. control cells).

As used herein, a "native *Bacillus* sp. rrnIp2 promoter" (abbreviated hereinafter, "rrnIp2" promoter) comprises a nucleotide sequence set forth in SEQ ID NO: 39.

As used herein, phrases such as a "modified rrnIp2" promoter, a "synthetic rrnIp2" promoter, a "variant rrnIp2" promoter, a "mutant rrnIp2" promoter, a "mutated rrnIp2" promoter and the like refer to genetically modified promoter sequences derived from a "native rrnIp2" promoter of SEQ ID NO: 39. For example, in certain embodiments, a modified (non-native) rrnIp2 promoter of the disclosure comprises at least one modified nucleotide position with reference to the native rrnIp2 promoter of SEQ ID NO: 39 (positions 1-91), wherein the at least a one (1) modified nucleotide position is selected from positions 1, 89, 90 or 91 of SEQ ID NO: 39.

In other embodiments, a modified (non-native) rrnIp2 promoter of the disclosure comprises at least two (2) modified nucleotide positions with reference to the native rrnIp2 promoter of SEQ ID NO: 39 (positions 1-91), wherein the at least a two modified nucleotide positions are selected from positions 1, 89, 90 or 91 of SEQ ID NO: 39.

In other embodiments, a modified (non-native) rrnIp2 promoter of the disclosure comprises at least three (3) modified nucleotide positions with reference to the native rrnIp2 promoter of SEQ ID NO: 39 (positions 1-91), wherein the at least three modified nucleotide positions are selected from positions 1, 89, 90 or 91 of SEQ ID NO: 39.

In other embodiments, a modified (non-native) rrnIp2 promoter of the disclosure comprises at least four (4) modified nucleotide positions with reference to the native rrnIp2 promoter of SEQ ID NO: 39 (positions 1-91), wherein the at least four modified nucleotide positions are 1, 89, 90 and 91 of SEQ ID NO: 39.

As used herein, a "rrnIp2-1" promoter comprises at least 90% sequence identity to SEQ ID NO: 40 and comprises a thymine (T) at nucleotide position 30, a thymine (T) at nucleotide position 89, a guanine (G) at nucleotide position 90 and thymine (T) at nucleotide position 91 of SEQ ID NO: 40. In certain other embodiments, a "rrnIp2-1" promoter comprises at least 90% to about 99% sequence identity to SEQ ID NO: 40 and comprises a thymine (T) at nucleotide position 30, a thymine (T) at nucleotide position 89, a guanine (G) at nucleotide position 90 and thymine (T) at nucleotide position 91 of SEQ ID NO: 40.

As used herein, a "rrnIp2-2" promoter comprises at least 90% sequence identity to SEQ ID NO: 58 and comprises a Tat nucleotide position 89, a G at nucleotide position 90 and a Tat nucleotide position 91 of SEQ ID NO: 58. In certain other embodiments, a "rrnIp2-2" promoter comprises at least 90% to about 99% sequence identity to SEQ ID NO: 58 and comprises a T at nucleotide position 89, a G at nucleotide position 90 and a Tat nucleotide position 91 of SEQ ID NO: 58.

As used herein, a "rrnIp2-3" promoter comprises at least 90% sequence identity to SEQ ID NO: 59 and comprises a T at nucleotide position 30 of SEQ ID NO: 59. In certain other embodiments, a "rrnIp2-3" promoter comprises at least 90% to about 99% sequence identity to SEQ ID NO: 59.

As used herein, terms such as a "synthetic" rrnIp2-1 promoter, a "synthetic" rrnIp2-2 promoter, a "synthetic" rrnIp2-3 promoter, "modified" rrnIp2-1 promoter, "modified" rrnIp2-2 promoter, "modified" rrnIp2-3 promoter and the like, refer to one or more (non-native) rrnIp2 promoter sequences (i.e., in contrast to the native rrnIp2 promoter sequence; SEQ ID NO: 39).

Thus, in certain embodiments, a synthetic, variant, or modified rrnIp2 promoter of the disclosure (e.g., a rrnIp2-1, rrnIp2-2, rrnIp2-3) comprises an enhanced promoter function or activity (e.g., an enhanced protein productivity phenotype) when operably linked to a gene or ORF encoding a protein of interest. In certain related embodiments, the synthetic, variant, or modified rrnIp2 promoter of the disclosure comprises an enhanced promoter function or activity relative to a native rrnIp2 promoter sequence of SEQ ID NO: 39.

Thus, in certain other embodiments, a parental *Bacillus* sp. cell comprising an endogenous native rrnIp2 promoter is modified according to the methods of the disclosure, wherein the modified *Bacillus* sp. (daughter) cell derived therefrom comprises a mutated (non-native) rrnIp2 promoter of the disclosure.

As used herein, with regard to a native rrnIp2 promoter, or a variant (modified) rrnIp2 promoter derived therefrom (e.g., a rrnIp2-1, rrnIp2-2, rrnIp2-3), the "position" of a nucleotide in a given "nucleic acid sequence" (i.e., a rrnIp2 promoter sequence disclosed herein) is numbered by reference to the native *B. subtilis* rrnIp2 promoter of SEQ ID NO: 39 (read in the 5' to 3' direction), which promoter sequence comprises nucleotides 1-91 (e.g., as presented in FIG. 1A-FIG. 1C).

For example, as shown in FIG. 1A-FIG. 1C, a candidate (test) promoter (nucleic acid) sequence described herein may be aligned with the native *B. subtilis* rrnIp2 promoter sequence (SEQ ID NO: 39; nucleotide positions 1-91) using alignment algorithms described herein and/or alignment algorithms known in the relevant arts, wherein the nucleotide positions in the candidate (test) sequence that align with the native promoter sequence of SEQ ID NO: 39, can be numbered by reference to the corresponding nucleotide position(s) in the native sequence. For example, as presented in FIG. 1A, a novel (synthetic) rrnIp2-1 promoter sequence of the disclosure (i.e., SEQ ID NO: 40) is aligned with the native *Bacillus* sp. rrnIp2 promoter sequence (i.e., SEQ ID NO: 39), wherein four (4) nucleotides at positions 30, 89, 90 and 91 differ between the native rrnIp2 promoter (SEQ ID NO: 39) and the novel rrnIp2-1 promoter (SEQ ID NO: 40). Thus, to establish sequence homology (or identity) to the native rrnIp2 promoter sequence of SEQ ID NO: 39, one skilled in the art may readily compare the native rrnIp2 promoter sequence with one or more candidate (test) promoter sequences of interest, using sequence alignment algorithms, software and methods thereof know to one skilled in the art.

In certain embodiments, a novel variant rrnIp2 promoter comprises a nucleic acid sequence which hybridizes (under stringent hybridization conditions) with a native rrnIp2 promoter sequence of SEQ ID NO: 39 or its complimentary sequence of SEQ ID NO: 60. For example, in certain embodiments, a novel variant rrnIp2 promoter comprises a nucleic acid sequence which hybridizes (under stringent hybridization conditions) with a complimentary rrnIp2 promoter sequence comprising SEQ ID NO: 60, wherein the variant sequence which hybridizes comprises at least one nucleotide substitution at a position selected from 30, 89, 90 or 91, relative to the same positions in the native rrnIp2 promoter sequence of SEQ ID NO: 39. Thus, in other embodiments, a novel variant rrnIp2 promoter sequence of the disclosure which hybridizes (under stringent hybridization conditions) comprises a T at nucleotide position 89, a G nucleotide position 90 and a T at nucleotide position 91 (i.e., relative to SEQ ID NO: 39, comprising an A, A, A at nucleotide positions 89-91). In other embodiments, a novel variant rrnIp2 promoter which hybridizes (under stringent hybridization conditions) comprises SEQ ID NO: 40, 58 or 59.

As used herein, a native *Bacillus licheniformis* "amyL promoter region" abbreviated hereinafter, "PamyL-1", comprises a nucleotide sequence set forth in SEQ ID NO: 64.

As used herein, a modified (synthetic) "amyL promoter region" abbreviated hereinafter, "PamyL-2", comprises a nucleotide sequence set forth in SEQ ID NO: 65.

In certain embodiments, a modified (synthetic) PamyL-2 sequence comprises at least 90% to about 99% sequence identity to SEQ ID NO: 64 and comprises a thymine (T) at nucleotide position 72 of SEQ ID NO: 64, a guanine (G) at nucleotide position 73 of SEQ ID NO: 64 and a thymine (T) at nucleotide position 74 of SEQ ID NO: 64.

As used herein, with regard to the native PamyL-1 sequence and the modified (synthetic) PamyL-2 sequence, the "position" of a nucleotide in a given "nucleic acid sequence" is numbered by reference to the to the native *B. licheniformis* amyL promoter region PamyL-1 of SEQ ID NO: 64 (read in the 5' to 3' direction), which native PamyL-1 promoter region sequence comprises nucleotide positions 1-100 of SEQ ID NO: 64 (i.e., 5' to 3', as presented in FIG. 3).

For example, as shown in FIG. 3, the native PamyL-1 promoter region comprises a native amyL promoter sequence comprising nucleotide positions 1-74 of SEQ ID NO: 64 and a native amyL 5'-UTR sequence comprising nucleotide positions 75-100 of SEQ ID NO: 64; and the modified (synthetic) PamyL-2 promoter region comprises a modified amyL promoter sequence comprising nucleotide positions 1-74 of SEQ ID NO: 65 operably linked to a native amyL 5'-UTR sequence comprising nucleotide positions 75-100 of SEQ ID NO: 65.

As used herein, a native *B. licheniformis* "amyL promoter" sequence comprises the nucleotide sequence set forth in SEQ ID NO: 82.

As used herein, a modified (synthetic) "amyL promoter" sequence comprises a nucleotide sequence set forth in SEQ ID NO: 83, and comprises a thymine (T) at nucleotide position 72 of SEQ ID NO: 83, a guanine (G) at nucleotide position 73 of SEQ ID NO: 83 and a thymine (T) at nucleotide position 74 of SEQ ID NO: 83. In certain embodiments, a modified (synthetic) amyL promoter sequence comprises a nucleotide sequence comprising at least 90% to about 99% sequence identity to SEQ ID NO: 82, and comprises a thymine (T) at nucleotide position 72 of SEQ ID NO: 82, a guanine (G) at nucleotide position 73 of SEQ ID NO: 82 and a thymine (T) at nucleotide position 74 of SEQ ID NO: 82.

As used herein, with regard to the native *B. licheniformis* amyL promoter sequence and a modified amyL promoter sequence, the "position" of a nucleotide in a given "nucleic acid sequence" is numbered by reference to the to the native *B. licheniformis* amyL promoter sequence of SEQ ID NO: 82 (read in the 5' to 3' direction), which native amyL promoter sequence comprises nucleotide positions 1-74 of SEQ ID NO: 82 (i.e 5' to 3', as presented in FIG. 4). For example, as shown in FIG. 4, the native amyL promoter sequence (SEQ ID NO: 82) comprises nucleotides A, T, and G at 72, 73 and 74, respectively, and the modified amyL promoter sequence (SEQ ID NO: 83) comprises nucleotides T, G, and T, at nucleotide positions 72, 73 and 74, respectively.

As used herein, a native *B. licheniformis* "amyL 5'-UTR" sequence comprises the nucleotide sequence set forth in SEQ ID NO: 84.

As used herein, a native *B. subtilis* "aprE 5'-UTR" comprises the nucleotide sequence set forth in SEQ ID NO: 85.

As used herein, a modified (synthetic) "amyL promoter region" abbreviated hereinafter "PamyL-3", comprises a nucleotide sequence set forth in SEQ ID NO: 66.

As used herein, a modified (synthetic) "amyL promoter region" abbreviated hereinafter "PamyL-4", comprises a nucleotide sequence set forth in SEQ ID NO: 67.

In certain embodiments, a modified (synthetic) PamyL-4 sequence comprises at least 90% to about 99% sequence identity to SEQ ID NO: 66 and comprises a thymine (T) at nucleotide position 72 of SEQ ID NO: 66, a guanine (G) at nucleotide position 73 of SEQ ID NO: 66 and a thymine (T) at nucleotide position 74 of SEQ ID NO: 66.

Thus, as used herein with regard to the synthetic PamyL-3 promoter region and the synthetic PamyL-4 promoter region, the "position" of a nucleotide in a given "nucleic acid sequence" is numbered by reference to the to the synthetic PamyL-3 promoter region of SEQ ID NO: 66 (read in the 5' to 3' direction), which PamyL-3 promoter region sequence comprises nucleotide positions 1-132 of SEQ ID NO: 66 (i.e., 5' to 3', as presented in FIG. 5).

For example, as shown in FIG. 5, the synthetic PamyL-3 promoter region (SEQ ID NO: 66) comprises a native amyL promoter sequence (e.g., SEQ ID NO: 82) comprising nucleotide positions 1-74 of SEQ ID NO: 66 operably linked to a native *B. subtilis* aprE 5'-UTR sequence (e.g., SEQ ID NO: 85) comprising nucleotide positions 75-132 of SEQ ID NO: 66. Likewise, as presented in FIG. 5, the synthetic PamyL-4 promoter region (SEQ ID NO: 67) comprises a modified amyL promoter sequence (e.g., SEQ ID NO: 83) comprising nucleotide positions 1-74 of SEQ ID NO: 67 operably linked to a native *B. subtilis* aprE 5'-UTR sequence (e.g., SEQ ID NO: 85) comprising nucleotide positions 75-132 of SEQ ID NO: 67.

Thus, as shown in FIG. 5, the PamyL-3 promoter region (SEQ ID NO: 66) comprises nucleotides A, T, and G, at nucleotide positions 72, 73 and 74, respectively, and the PamyL-4 promoter region (SEQ ID NO: 67) comprises nucleotides T, G, and T, at nucleotide positions 72, 73 and 74, respectively.

As used herein, with regard to the PamyL-1 promoter region (SEQ ID NO: 64), the PamyL-2 promoter region (SEQ ID NO: 65), the PamyL-3 promoter region (SEQ ID NO: 66) and the PamyL-4 promoter region (SEQ ID NO: 67), the terms "promoter region" or "promoter region sequence" refer to a nucleic acid sequence comprising at least an upstream (5') promoter sequence operably linked to a downstream (3') 5-UTR sequence.

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand.

As used herein, the term "3'-untranslated region" is abbreviated "3'-UTR and the term "5'-untranslated region" is abbreviated "5'-UTR.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the transcription of that coding sequence (i.e., that the coding sequence is under the transcriptional control of the promoter). Coding sequences can be operably linked to regulatory sequences in sense or anti-sense orientation. A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites or seamless assembly methods. If such sites do not exist, the synthetic oligonucleotide adaptors or linkers are used in accordance with conventional practice.

As used herein, "suitable regulatory sequences" refer to nucleotide sequences located upstream (5', non-coding sequences), within, or downstream (3', non-coding sequences) of a coding sequence, and which influence transcription, RNA processing or stability, or translation of the associated coding sequence. Regulatory sequences may include promoters, translation leader sequences, RNA processing site(s), effector binding site(s), stem-loop structures and other RNA stability motifs.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As used herein, the combined term "expresses/produces", as used in phrases such as a "Bacillus sp. (daughter) cell expresses/produces an 'increased' amount of a protein of interest (POI)" (i.e., relative to the parental cell), the term "expresses/produces" is meant to include any steps involved in the expression and production of a protein in such Bacillus sp. (daughter) cells of the disclosure.

As used herein, the terms "increased expression", "enhanced expression", "increased expression of a POI", "increased production", "increased production of a POI" and the like refer to a "modified" Bacillus (daughter) cell, wherein the "increase" is always relative (vis-à-vis) to an "unmodified" Bacillus (parental) cell expressing/producing the same POI.

Likewise, as used herein, an "increased amount", when used in phrases such as "a modified host cell 'expresses/produces an increased amount' of one or more proteins of interest relative to the (unmodified) parental host cell", particularly refers to an "increased amount" of any protein of interest (POI) expressed/produced in the modified host cell, which "increased amount" is always relative to the (unmodified) parental Bacillus cells expressing/producing the same POI, wherein the modified and unmodified cells are grown/cultured/fermented under the same conditions (e.g., the same conditions such as media, temperature, pH and the like). For example, an increased amount of a POI may be an endogenous POI or a heterologous POI expressed in a modified Bacillus cell of the disclosure.

Thus, as used herein, "increasing" protein production or "increased" protein production is meant an increased amount of protein produced (e.g., a protein of interest). The protein may be produced inside the host cell, or secreted (or transported) into the culture medium. In certain embodiments, the protein of interest is produced (secreted) into the culture medium. Increased protein production may be detected for example, as higher maximal level of protein or enzymatic activity (e.g., such as protease activity, amylase activity, cellulase activity, hemicellulase activity and the like), or total extracellular protein produced as compared to the parental host cell.

As used herein, a modified cell comprising an "enhanced protein productivity phenotype" includes, but is not limited to, a modified cell comprising an enhanced/increased volumetric productivity, a modified cell comprising an enhanced/increased carbon conversion efficiency, a modified cell comprising an enhanced/increased protein yield, a modified cell comprising an enhanced/increased specific protein productivity and the like.

As used herein, the phrases "enhanced protein productivity phenotype" and "increased protein productivity phenotype", may be used interchangeably.

As used herein, when describing an "enhanced/increased protein productivity phenotype" in an unmodified (parental) cell vis-à-vis a modified (variant/daughter) cell, it will be understood that the "parental" and "variant" cells are grown/cultivated/fermented under the same conditions (e.g., the same conditions such as media, temperature, pH and the like). \

As used herein, the term "introducing", as used in phrases such as "introducing into a cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection and the like.

It is understood that the polynucleotides (or nucleic acid molecules) described herein include "genes", "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a bacterial cell" or "introducing into a *Bacillus* cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein "an incoming sequence" refers to a DNA sequence that is introduced into the *Bacillus* chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, the non-functional sequence may be inserted into a gene to disrupt function of the gene. In another embodiment, the incoming sequence includes a selective marker. In a further embodiment the incoming sequence includes two homology boxes (e.g., up-stream and down-stream homology arms).

As used herein, "homology box" refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking regions of a chromosomal locus of interest according to the invention. These sequences direct where in the *Bacillus* chromosome a DNA construct is integrated and directs what part, if any, of the *Bacillus* chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box (homology arms) wherein the homology box comprises nucleic acid sequences immediately flanking the coding region of the gene.

In still another embodiment of the disclosure, the deletion, disruption, inactivation or down-regulation of a gene active at an inappropriate time, as determined by DNA array analysis (e.g., transcriptome analysis, as described herein) provides enhanced expression of a protein of interest. As used herein, "transcriptome analysis" refers to the analysis of gene transcription.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, the marker can be an antimicrobial resistance marker (e.g., amp$^R$, phleo$^R$, spec$^R$, kan$^R$, ery$^R$, tet$^R$, cmp$^R$ and neo"). In some embodiments, the present invention provides a chloramphenicol resistance gene (e.g., the gene present on pC194, as well as the resistance gene present in the *Bacillus licheniformis* genome). This resistance gene is particularly useful in the present invention, as well as in embodiments involving chromosomal amplification of chromosomally integrated cassettes and integrative plasmids. Other markers useful in accordance with the invention include, but are not limited to auxotrophic markers, such as serine, lysine, tryptophan; and detection markers, such as β-galactosidase.

As defined herein, a host cell "genome", a bacterial (host) cell "genome", or a *Bacillus* (host) cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A used herein, a "transformation cassette" refers to a specific vector comprising a gene (or ORF thereof), and having elements in addition to the foreign gene that facilitate transformation of a particular host cell.

As used herein, the term "vector" refers to any nucleic acid that can be replicated (propagated) in cells and can carry new genes or DNA segments into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously or can integrate into a chromosome of a host organism).

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is well within the knowledge of those having skill in the art.

As used herein, the term "plasmid" refers to a circular double-stranded (ds) DNA construct used as a cloning vector, and which forms an extrachromosomal self-replicating, conditionally self-replicating, or non-replicating genetic element in many bacteria and some eukaryotes. In some embodiments, plasmids become incorporated into the genome of the host cell.

As used herein, the term "protein of interest" or "POI" refers to a polypeptide of interest that is desired to be expressed in a modified *Bacillus* (daughter) cell, wherein the POI is preferably expressed at enhanced/increased levels (i.e., relative to the "unmodified" (parental) cell). Thus, as used herein, a POI may be an enzyme, a substrate-binding protein, a surface-active protein, a structural protein, a receptor protein, an antibody and the like Similarly, as defined herein, a "gene of interest" or "GOT" refers a nucleic acid sequence (e.g., a polynucleotide, a gene or an ORF) which encodes a POI. A "gene of interest" encoding a "protein of interest" may be a naturally occurring gene, a mutated gene or a synthetic gene.

In certain embodiments, a modified cell of the disclosure produces an increased amount of a heterologous POI or an endogenous POI relative to the parental cell. In particular embodiments, an increased amount of a POI produced by a modified cell of the disclosure is at least a 0.05% increase, at least 0.10%, at least a 1.0% increase, at least a 5.0% increase, or a greater than 5.0% increase, relative to the parental cell. As a non-limiting example, in certain embodiments, the POI is an enzyme (e.g., hydrolase), wherein an increased level of the POI produced by the modified cell (i.e., relative to its unmodified parent) is detected or measured as an increase in enzymatic activity and/or an increase specific productivity (Qp).

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains) or occur spontaneously.

As used herein, in the context of a polypeptide or a sequence thereof, the term "substitution" means the replacement (i.e., substitution) of one amino acid with another amino acid.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer. As used herein, the term "foreign" gene(s) comprise native genes (or ORFs) inserted into a non-native organism and/or chimeric genes inserted into a native or non-native organism.

As defined herein, a "heterologous" nucleic acid construct or a "heterologous" nucleic acid sequence has a portion of the sequence which is not native to the cell in which it is expressed.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "derived" encompasses the terms "originated" "obtained," "obtainable," and "created," and generally indicates that one specified material or composition finds its origin in another specified material or composition, or has features that can be described with reference to the another specified material or composition.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wis., USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As defined herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the term "ComK polypeptide" is defined as the product of a comK gene; a transcription factor that acts as the final auto-regulatory control switch prior to competence development; involved with activation of the expression of late competence genes involved in DNA-binding and uptake and in recombination (Liu and Zuber, 1998, Hamoen et al., 1998). A plasmid (pBL.comK) comprising and expressing the comK nucleic acid sequence is set forth in SEQ ID NO: 43.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "orthologue" and "orthologous genes" refer to genes in different species that have evolved from a common ancestral gene (i.e., a homologous gene) by speciation. Typically, orthologues retain the same function during the course of evolution. Identification of orthologues finds use in the reliable prediction of gene function in newly sequenced genomes.

As used herein, "paralog" and "paralogous genes" refer to genes that are related by duplication within a genome. While orthologues retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, Wis.) and Devereux et. al., 1984).

As used herein, an "analogous sequence" is one wherein the function of the gene is essentially the same as the gene derived from a *Bacillus* cell. Additionally, analogous genes include at least 60%, 65%, 70%, 75%, 80%, 85%, 90%, 95%, 97%, 98%, 99% or 100% sequence identity with the sequence of the *Bacillus* sp. cell. Analogous sequences are determined by known methods of sequence alignment. A commonly used alignment method is BLAST, although there are other methods that also find use in aligning sequences.

As used herein, the term "hybridization" refers to the process by which a strand of nucleic acid joins with a complementary strand through base pairing, as known in the art. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$ −5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/ml denatured carrier DNA, followed by washing two times in 2×SSC and 0.5% SDS at room temperature (RT) and two additional times in 0.1×SSC and 0.5% SDS at 42° C. An example of moderate stringent conditions including overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination", "recombining" or generating a "recombined" nucleic acid is generally the assembly of two or more nucleic acid fragments wherein the assembly gives rise to a chimeric gene.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In other embodiments, the 5' and 3' ends of a selective marker are flanked by a polynucleotide sequence comprising a section of the inactivating chromosomal segment. In some embodiments, a flanking sequence is present on only a single side (either 3' or 5'), while in other embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a non-critical target for a cell to initiate DNA uptake.

II. Ribosomal RNA Promoter Sequences

As generally set forth above, certain embodiments of the disclosure are related to novel promoter (nucleic acid) sequences described herein. In certain embodiments, these novel promoter sequences are operably linked to a gene or ORF encoding a POI, wherein they are particularly well suited for use in large scale production of industrially relevant proteins. In certain embodiments, such novel promoter sequences are synthetic variants of a native *Bacillus* sp. ribosomal RNA (rrn) promoter (nucleic acid) sequence.

For example, as presented in the Background section above, International PCT Publication No. WO2013/086219, generally discloses promoters, expression vectors, microorganisms, and methods for the production of polynucleotides coding for proteins of interest comprising ribosomal promoters derived from *Bacillus subtilis*, which ribosomal promoter sequences described therein are useful for enhanced protein production in Gram positive microbial cells. These ribosomal RNA and ribosomal protein promoter sequences included certain *B. subtilis* ribosomal RNA promoters (abbreviated "rrn"), such as rrnB, rrnI, and rrnE and certain *B. subtilis* ribosomal protein promoters (abbreviated "rps"), such as rpsD and rpsJ.

In contrast, as presented and described in the Examples section below, Applicant has identified novel mutant/variant promoter sequences derived from such rrn promoter (nucleic acid) sequences. More particularly during routine synthesis of DNA for assembly into *Bacillus* expression constructs, Applicant altered the sequence of the rrn promoter to facilitate DNA assembly of the constructs, during these alterations applicant identified certain *B. subtilis* rrnIp2 promoter mutants that expressed/produced increased amounts of the operably linked reporter gene compared with the native rrnIp2 promoter sequence (e.g., variant/mutated rrnIp2 promoter sequences such as SEQ ID NOs: 40, 58 and 59).

For example, as presented and described in Example 1, Applicant constructed an aprE Cas9 targeting vector for the introduction of expression cassettes into the aprE locus of *B. subtilis*. Thus, to create a guide RNA (gRNA) expression cassette, the DNA encoding the gRNA was operably linked to a promoter sequence and terminator sequence operable in *Bacillus* sp. cells, such that the promoter was positioned upstream (5') of the DNA encoding the gRNA and the terminator was positioned downstream (3') of the DNA encoding the gRNA. In addition, Example 2 of the disclosure further describes the construction of *Bacillus* sp. (daughter) cells comprising introduced hydrolase expressions cassettes. More particularly, such *Bacillus* sp. cells comprise hydrolase expression cassettes having (1) a DNA sequence homologous to flanking region 5' of the yhfN gene (SEQ ID NO: 38) operably linked to either (2a) a DNA sequence encoding a native *B. subtilis* rrnIp2 promoter (SEQ ID NO: 39) or (2b) a novel (synthetic) variant rrnIp2-1 promoter (SEQ ID NO: 40), which promoter DNA sequences are (3) operably linked to a DNA sequence encoding an exemplary protein of interest (i.e., a hydrolase), which is (4) operably fused to a DNA sequence encoding a *B. amyloliquefaciens* apr terminator sequence (SEQ ID NO: 41), wherein the promoter is positioned upstream (5') of the DNA sequence encoding the hydrolase and the terminator is positioned downstream (3') of the DNA encoding the hydrolase. Additionally, such expression cassettes were operably fused to the DNA sequence homologous to the flanking region 3' of the yhfN gene (SEQ ID NO: 42). For example, a *Bacillus* sp. (daughter) cell colony comprising the hydrolase expression cassette with the native rrnIp2 promoter (SEQ ID NO: 39) was stored and named strain "SS066", and a *Bacillus* sp. (daughter) cell colony comprising the hydrolase expression cassette with the modified rrnIp2-1 promoter (SEQ ID NO: 40) was stored and named strain "SS065".

Example 3 of the disclosure further describes *Bacillus* sp. cells comprising a hydrolase expression cassette (i.e., Example 3; a protease) with either a native rrnIp2 promoter (e.g., *Bacillus* cells SS066) or a modified rrnIp2-1 promoter (e.g., *Bacillus* cells SS065) were assessed for hydrolase (i.e., protease) production under small scale conditions. More particularly, after forty (40) hours of growth, the protease concentration in the whole cell broth was determined using the suc-AAPF-pNA assay. For example, Table 5 (Example 3) shows the (normalized) relative protease expression of the SS065 cells (i.e., comprising rrnIp2-1 promoter; SEQ ID NO: 40) relative to the SS066 cells (i.e., comprising native rrnIp2 promoter; SEQ ID NO: 39), demonstrating an approximately 2-fold increase in protease activity.

Likewise, Example 4 of the disclosure presents *Bacillus* sp. cells comprising exemplary hydrolase expression cassettes (i.e., Example 4; an amylase). More specifically, the amylase expression cassettes described in Example 4 were introduced into *B. licheniformis* cells, comprising an amylase expression cassette either (1) under the control of the native rrnIp2 promoter (SEQ ID NO: 39) or (2) under the control of the a modified rrnIp2-1 promoter (SEQ ID NO: 40). More particularly, halo positive transformants for the native rrnIp2 amylase cassette and modified rrnIp2-1 amylase cassette were streak purified on L agar containing 1% (w/v) insoluble starch to purify single colonies, wherein a colony with a sequence verified cassette of the rrnIp2_amylase cassette was stored and named "BF399" and a colony with a sequence verified cassette of the rrnIp2-1_amylase cassette was stored and named "BF401".

Example 5 of the disclosure further assayed the *Bacillus* sp. cells (i.e., cells BF399 and BF401) comprising the amylase expression cassettes constructed in Example 4. For example, as presented in Table 9, the amylase expression cassette comprising the native rrnIp2 promoter (i.e., cassette SEQ ID NO: 44) and the amylase expression cassette comprising the variant rrnIp2-1 promoter (i.e., cassette SEQ ID NO: 45), were tested for expression/production of the amylase to determine the influence these different promoters have on amylase production in *Bacillus* sp. cells. More particularly, as presented in Table 9, the *Bacillus* sp. cells comprising the variant rrnIp2-1 promoter (SEQ ID NO: 40; i.e., cassette SEQ ID NO: 45) produce on average 30% more amylase than the *Bacillus* sp. cells comprising the native rrnIp2 promoter (i.e., cassette SEQ ID NO: 44).

Thus, as generally described herein, certain embodiments of the disclosure are related to compositions and methods for producing/constructing *Bacillus* sp. cells (e.g., protein production host cells, cell factories) having increased protein production phenotypes and the like.

III. *Bacillus Licheniformis* amyL Promoter Region Sequences

As generally set forth above, certain embodiments of the disclosure are related to novel promoter (nucleic acid) sequences described herein. Thus, in certain embodiments, novel promoter sequences described herein are operably linked to a gene or ORF encoding a POI, which novel promoter sequences are particularly well suited for use in large scale production of industrially relevant proteins. For example, certain embodiments are related to novel promoter sequence regions comprising upstream promoter sequences operably linked to downstream 5'-UTR sequences, as generally described herein. In certain embodiments, such novel promoter sequences regions are synthetic (modified) variants of a native *B. licheniformis* amyL promoter (nucleic acid) sequence.

For example, as generally set forth in Section II above (e.g., see, FIG. 1), when the 3' adenines (A) at nucleotide positions 89, 90 and 91 of the native rrnIp2 promoter sequence (SEQ ID NO: 39) were changed to a thymine (T) at nucleotide position 89, a guanine (G) at nucleotide position 90 and thymine (T) at nucleotide position 91 of the rrnIp2-1 promoter sequence (SEQ ID NO: 40; SEQ ID NO: 58), the expression of genes of interest under the control of the (TGT) modified rrnIp2-1 promoter (SEQ ID NO: 40; SEQ ID NO: 58) were significantly enhanced relative to the expression of the same genes of interest expressed under the control of the native rrnIp2 promoter (SEQ ID NO: 39). Based on these surprising and unexpected observations of the modified rrnIp2 promoter sequences, Applicant contemplated introducing similar 3' nucleotide modifications into a native *B. licheniformis* amyL promoter region.

More specifically, as described below in the Example 6, in certain embodiments Applicant modified a native *B. licheniformis* amyL promoter region (named PamyL-1; SEQ ID NO: 64), which native PamyL-1 promoter region comprises a native *B. licheniformis* amyL promoter sequence (SEQ ID NO: 82) and a native *B. licheniformis* amyL 5'-UTR sequence (SEQ ID NO: 84), whereas the modified amyL promoter region (named PamyL-2; SEQ ID NO: 65) comprises a modified (synthetic) amyL promoter sequence (SEQ ID NO: 83) operably linked to a native *B. licheniformis* amyL 5'-UTR sequence (SEQ ID NO: 84), for example, see FIG. 3 and FIG. 4. In certain other embodiments, Applicant constructed synthetic (hybrid) promoter regions named PamyL-3 (SEQ ID NO: 66) and PamyL-4 (SEQ ID NO: 67), wherein the hybrid PamyL-3 promoter region (SEQ ID NO: 66) comprises native *B. licheniformis* amyL promoter sequence (SEQ ID NO: 82) operably linked to a native *B. subtilis* aprE 5'-UTR sequence (SEQ ID NO: 85) and the hybrid PamyL-4 promoter region (SEQ ID NO: 67) comprises modified *B. licheniformis* amyL promoter sequence (SEQ ID NO: 83) operably linked to a native *B. subtilis* aprE 5'-UTR sequence (SEQ ID NO: 85). For example, as shown in the FIG. 5 nucleic acid sequence alignments, the putative transcription start-site (TSS) is indicated with bold nucleotides followed by the 5'-UTR sequence indicated with italicized nucleotides and a double-underlined "G" nucleotide to assist in visualizing the TSS of PamyL-3 relative to PamyL-4.

Thus, as generally set forth in Example 6, heterologous (truncated) pullulanase expression cassettes were introduced into *B. licheniformis* cells. More specifically, the (truncated) pullulanase expression cassettes were introduced into *B. licheniformis* cells, wherein the cells comprised either (a) an expression cassette under the control of the native *B. licheniformis* amyL promoter region (i.e., PamyL-1; SEQ ID NO: 64), (b) an expression cassette under the control of modified promoter region PamyL-2 (SEQ ID NO: 65), (c) an expression cassette under the control of modified promoter region PamyL-3; (SEQ ID NO: 66), or (d) an expression cassette under the control of modified promoter region PamyL-4 (SEQ ID NO: 67). For example, as described in Example 6, a colony with a sequence verified cassette of the PamyL-1 pullulanase cassette (SEQ ID NO: 78) was streak purified, stored and named "PamyL-Pulltr.", a colony with a sequence verified cassette of the PamyL-2 pullulanase cassette (SEQ ID NO: 79) was streak purified, stored and named "LDN461", a colony with a sequence verified cassette of the PamyL-3 pullulanase cassette (SEQ ID NO: 80) was streak purified, stored and named "LDN462", and a colony with a sequence verified cassette of the PamyL-4 pullulanase cassette (SEQ ID NO: 81) was streak purified, stored and named "LDN463".

More particularly, as further described in Example 7, Applicant assayed *Bacillus* cells (strains) comprising the introduced (truncated) pullulanase expression cassettes to determine the influence these different promoter regions have on such heterologous pullulanase protein production. For example, the data presented in Example 7 demonstrate that the *Bacillus* strain comprising the PamyL-2 pullulanase cassette (SEQ ID NO: 79; e.g., strain LDN461) produced on average 78% more pullulanase than the *Bacillus* strain comprising the PamyL-1 pullulanase cassette (SEQ ID NO: 78; strain PamyL-Pulltr.). Likewise, the data presented in Example 7 demonstrate that the *Bacillus* strain comprising the PamyL-4 pullulanase cassette (SEQ ID NO: 81; strain LDN463) produced on average 16% more pullulanase than the *Bacillus* strain comprising the PamyL-3 pullulanase cassette (SEQ ID NO: 80; strain LDN462).

Thus, as generally described herein, certain embodiments of the disclosure are related to compositions and methods for producing/constructing *Bacillus* sp. cells (e.g., protein production host cells, cell factories) having increased protein production phenotypes and the like.

IV. Molecular Biology

As generally set forth above, certain embodiments of the disclosure are related to modified *Bacillus* sp. (daughter) cells derived from parental *Bacillus* sp. cells. More particularly, certain other embodiments are related to modified *Bacillus* sp. (daughter) cells and methods thereof for producing and constructing such modified *Bacillus* sp. cells (e.g., protein production host cells, cell factories) having increased protein productivity phenotypes and the like. Thus, certain other embodiments are related to mutants of parental *Bacillus* sp. cells comprising one or more genetic modifications (i.e., relative to the parental cell).

As presented herein, such novel promoter (nucleic acid) sequences are particularly useful for the expression of a gene or ORF encoding a protein of interest in a *Bacillus* sp. cell. Other embodiments are related to such to novel promoter (nucleic acid) sequences comprised within novel expression cassettes thereof. Thus, certain other embodiments are related to modified *Bacillus* sp. cells comprising one or more heterologous expression constructs introduced therein. Certain other embodiments are related to an isolated protein of interest (POI) produced by a modified *Bacillus* sp. cell of the disclosure. Thus, in certain embodiments, one or more promoter sequences are operably linked to a gene or ORF encoding a POI. In certain other embodiments, the one or more promoter sequences further comprise nucleotides upstream (5') and operably linked thereto. In other embodiments, the gene or ORF further comprises nucleotides downstream (3') and operably linked thereto.

Thus, certain embodiments of the disclosure are directed to methods for genetically modifying *Bacillus* sp. cells (e.g., via the introduction, substitution, and/or removal of one or more nucleotides in a gene, ORF, promoter, terminator, 5'-UTR, 3'-UTR and the like). Thus, methods for genetically modifying *Bacillus* sp. cells include, but are not limited to (a) the introduction, substitution, and/or removal of one or more nucleotides in a given nucleic acid sequence, (b) gene disruption, (c) gene conversion, (d) gene deletion, (e) gene down-regulation, (f) Cas9 mediated editing, (g) site specific mutagenesis and/or (h) random mutagenesis. Thus, in certain embodiments, a parental *Bacillus* sp. cell is modified using methods well known in the art, for example, insertions, disruptions, replacements, or deletions and the like in a polynucleotide sequence of interest.

For example, in certain embodiments, a portion of a gene to be modified may be a coding region or a regulatory element required for expression of the coding region. In certain embodiments, a *Bacillus* sp. nucleic acid sequence (e.g., a gene, an ORF, a promoter, a 5'-UTR and the like) is modified using methods known in the art. In certain embodiments, a promoter (nucleic acid) sequence is modified using methods known in the art. In other embodiments, a promoter derived from a native *Bacillus* sp. is modified using methods known in the art. In certain other embodiments, a variant *Bacillus* sp. promoter of the disclosure is a synthetic sequence (e.g., rrnIp2-1 promoter; SEQ ID NO: 40).

Thus, in certain embodiments a modified *Bacillus* sp. cell is constructed by gene deletion. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art may readily identify nucleotide regions in the gene's coding sequence and/or the gene's non-coding sequence suitable for complete or partial deletion.

In other embodiments, a modified *Bacillus* sp. cell of the disclosure is constructed by introducing, substituting, or removing one or more nucleotides in the gene or a regulatory element required for the transcription or translation thereof. For example, as described herein, certain modified promoter (nucleic acid) sequences of the disclosure comprise nucleotide substitutions (e.g., nucleotide positions 30, 89, 90 and 91). Such a modification may be accomplished techniques known in the art, such as site-directed mutagenesis or PCR generated mutagenesis in accordance with methods known in the art (e.g., see, Botstein and Shortie, 1985; Lo et al., 1985; Higuchi et al., 1988; Shimada, 1996; Ho et al., 1989; Horton et al., 1989 and Sarkar and Sommer, 1990).

In another embodiment, a modified *Bacillus* sp. cell is constructed by the process of gene conversion (e.g., see Iglesias and Trautner, 1983). For example, in the gene conversion method, a nucleic acid sequence corresponding to the gene(s) is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Bacillus* sp. cell is produced/constructed via CRISPR-Cas9 editing. For example, a *Bacillus* sp. promoter sequence of the disclosure can be edited (or disrupted, deleted, down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to modify the promoter sequence (e.g., see, Example 1). Thus, the gene encoding the nucleic acid guided endonuclease (for this purpose Cas9 from *S. pyogenes*) or a codon optimized gene encoding the Cas9 nuclease is operably linked to a promoter active in the *Bacillus* sp. cell and a terminator active in *Bacillus* cell, thereby creating a *Bacillus* Cas9 expression cassette. Likewise, one or more target sites unique to the promoter of interest are readily identified by a person skilled in the art. For example, to build a DNA construct encoding a gRNA-directed to a target promoter site of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells. In certain embodiments, the DNA break induced by the endonuclease is repaired/replaced with an incoming sequence.

For example, to precisely repair the DNA break generated by the Cas9 expression cassette and the gRNA expression cassette described above, a nucleotide editing template is provided, such that the DNA repair machinery of the cell can utilize the editing template. For example, about 500 bp upstream (5') of targeted promoter can be fused to about 500 bp downstream (3') of the targeted promoter to generate an editing template, which template is used by the *Bacillus* host's machinery to repair the DNA break generated by the RGEN. The Cas9 expression cassette, the gRNA expression cassette and the editing template can be co-delivered to the cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN. These fragments are then sequenced using a sequencing primer to identify edited colonies.

In yet other embodiments, a modified *Bacillus* sp. cell is constructed by random or specific mutagenesis using methods well known in the art, including, but not limited to, chemical mutagenesis (see, e.g., Hopwood, 1970) and transposition (see, e.g., Youngman et al., 1983). Modification of the gene or promoter may be performed by subjecting the parental cell to mutagenesis and screening for mutant cells in which expression of the gene has been altered. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

International PCT Publication No. WO2003/083125 (incorporated herein by reference in its entirety) discloses methods for modifying *Bacillus* cells, such as the creation of *Bacillus* deletion strains and DNA constructs using PCR fusion to bypass *E. coli*. International PCT Publication No. WO2002/14490 (incorporated herein by reference in its entirety) discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double crossover integrations, (6) site directed mutagenesis and (7) marker-less deletion.

Those of skill in the art are well aware of suitable methods for introducing polynucleotide sequences into bacterial cells (e.g., *E. coli* and *Bacillus* sp.; see e.g., Ferrari et al., 1989; Saunders et al., 1984; Hoch et al., 1967; Mann et al., 1986; Holubova, 1985; Chang et al., 1979; Vorobjeva et al., 1980; Smith et al., 1986; Fisher et. al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984 and Palmeros et al., 2000). In some embodiments, resolution of the vector from a host chromosome leaves the flanking regions in the chromosome, while removing the indigenous chromosomal region.

Methods for screening and creating promoter libraries with a range of activities (promoter strength) in *Bacillus* cells is describe in International PCT Publication No. WO2003/089604.

V. Culturing *Bacillus* Cells for Production of a Protein of Interest

In other embodiments of the disclosure, the *Bacillus* sp. cells constructed and described herein comprise enhanced protein productivity phenotypes. More specifically, the modified *Bacillus* sp. (daughter) cells of the disclosure comprise enhanced protein productivity phenotypes relative to the parental *Bacillus* sp. cells from which there were derived, when the parental and daughter cells are cultivated under the same conditions. Thus, certain embodiments of the disclosure are related to methods of expressing/producing a protein of interest (POI), which generally comprises fermenting/cultivating such cells.

Fermentation methods well known in the art can be applied to ferment the modified and unmodified *Bacillus* sp. cells of the disclosure. In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Thus, in certain embodiments, a POI produced by a transformed (modified) host cell may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate. The precipitated proteins are then solubilized and may be purified by a variety of chromatographic procedures, e.g., ion exchange chromatography, gel filtration.

VI. Proteins of Interest Produced by Modified Cells

As briefly stated in the preceding section, the present cells, strains, polynucleotides, promoters, expression constructs and methods thereof find use in the production of commercially important proteins. A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

For example, in certain embodiments, a modified *Bacillus* sp. (daughter) cell comprises an increased protein titer relative to a parental *Bacillus* sp. cell from which it was derived, wherein protein titer is defined as the amount of protein per volume (g/L). For example, titers can be measured by methods known in the art (e.g., ELISA, HPLC, Bradford assay, LC/MS and the like). Thus, in certain embodiments, a modified *Bacillus* sp. (daughter) cell comprises a protein titer increase of at least about 0.1%, at least about 1%, at least about 5%, at least about 6%, at least about 7%, at least about 8%, at least about 9%, or at least about 10% or more, relative to the parental *Bacillus* sp. cell from which it was derived.

In certain embodiments, a modified *Bacillus* sp. (daughter) cell exhibits an increased volumetric productivity relative to a parental *Bacillus* sp. cell from which it was derived, wherein volumetric productivity is defined as the amount of protein produced (g) during the fermentation per nominal volume (L) of the bioreactor per total fermentation time (h). For example, volumetric productivities can be measured by methods know in the art (e.g., ELISA, HPLC, Bradford assay, LC/MS and the like). Thus, in certain embodiments, a modified *Bacillus* sp. (daughter) cell comprises a volumetric productivity increase of at least about 0.1%, at least about 1%, at least about 5%, at least about 6%, at least about 7%, at least about 8%, at least about 9%, or at least about 10% or more, relative to the parental *Bacillus* sp. cell from which it was derived.

In certain other embodiments, a modified *Bacillus* sp. (daughter) cell exhibits an increased total protein yield relative to a parental *Bacillus* sp. cell from which it was derived, wherein total protein yield is defined as the amount of protein produced (g) per gram of carbohydrate fed. Thus, as used herein, total protein yield (g/g) may be calculated using the following equation:

$$Y_f = T_p/T_c$$

wherein "$Y_f$" is total protein yield (g/g), "$T_p$" is the total protein produced during the fermentation (g) and "$T_c$" is the total carbohydrate (g) fed during the fermentation (bioreactor) run. In certain embodiments, the increase in total protein yield of the modified *Bacillus* sp. (daughter) cell, relative to parental *Bacillus* sp. cell from which it was derived, is an increase of at least about 0.1%, at least about 1%, at least about 5%, at least about 6%, at least about 7%, at least about 8%, at least about 9%, or at least about 10% or more.

Total protein yield may also be described as carbon conversion efficiency/carbon yield, for example, as in the percentage (%) of carbon fed that is incorporated into total protein. Thus, in certain embodiments, a modified *Bacillus* sp. (daughter) cell comprises an increased carbon conversion efficiency (e.g., an increase in the percentage (%) of carbon fed that is incorporated into total protein) relative to the parental *Bacillus* sp. cell from which it was derived. In certain embodiments, the increase in carbon conversion efficiency of the modified cell (i.e., relative to the parental cell) is an increase of at least about 0.1%, at least about 1%, at least about 5%, at least about 6%, at least about 7%, at least about 8%, at least about 9%, or at least about 10% or more.

In certain embodiments, a modified *Bacillus* sp. (daughter) cell exhibits an increased specific productivity (Qp) of a POI relative to the parental *Bacillus* sp. cell from which it was derived. For example, the detection of specific productivity (Qp) is a suitable method for evaluating rate of protein production. The specific productivity (Qp) can be determined using the following equation:

$$"Qp = gP/gDCW \cdot hr"$$

wherein, "gP" is grams of protein produced in the tank; "gDCW" is grams of dry cell weight (DCW) in the tank and "hr" is fermentation time in hours from the time of inoculation, which includes the time of production as well as growth time. Thus, in certain embodiments, a modified *Bacillus* sp. (daughter) cell comprises a specific productivity (Qp) increase of at least about 0.1%, at least about 1%, at least about 5%, at least about 6%, at least about 7%, at least about 8%, at least about 9%, or at least about 10% or more, relative to the parental *Bacillus* sp. cell from which it was derived.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannanases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

In certain embodiments, a POI or a variant POI thereof is selected from an Enzyme Commission (EC) Number selected from the group consisting of EC 1, EC 2, EC 3, EC 4, EC 5 or EC 6.

For example, in certain embodiments a POI is an oxidoreductase enzyme, including, but not limited to, an EC1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase), EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.1.26.5 (e.g., ribonuclease P), EC 3.1.3.X (e.g., phosphoric monoester hydrolase), EC 3.1.30.1 (e.g., *Aspergillus* nuclease S1), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-β-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetyl-glucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.- (e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase).

These and other aspects and embodiments of the present strains and methods will be apparent to the skilled person in view of the present description and the following Examples.

EXAMPLES

Certain aspects of the present invention may be further understood in light of the following examples, which should Example 1

Construction of aprE Cas9 Targeting Vector

A synthetic polynucleotide encoding the Cas9 protein from *S. pyogenes* (SEQ ID NO: 1), comprising an N-terminal nuclear localization sequence (NLS, "APKKKRKV"; SEQ ID NO:2), a C-terminal NLS ("KKKKLK"; SEQ ID NO: 3) and a deca-histidine tag ("HHHHHHHHHH"; SEQ ID NO: 4), was operably linked to the aprE promoter (P-aprE) from *B. subtilis* (SEQ ID NO: 5) and amplified using Q5 DNA polymerase (NEB) per manufacturer's instructions with the forward (SEQ ID NO: 6) and reverse (SEQ ID NO: 7) primer pair set forth below in TABLE 1.

TABLE 1

| | FORWARD AND REVERSE PRIMER PAIR | |
|---|---|---|
| Forward | ATATATGAGTAAACTTGGTCTGACA GAATTCCTCCATTTTCTTCTGCTAT | SEQ ID NO: 6 |
| Reverse | TGCGGCCGCGAATTCGATTACGAAT GCCGTCTCCC | SEQ ID NO: 7 |

The backbone (SEQ ID NO: 8) of plasmid pKB320 (SEQ ID NO: 9) was amplified using Q5 DNA polymerase (NEB) per manufacturer's instructions with the forward (SEQ ID NO: 10) and reverse (SEQ ID NO: 11) primer pair set forth below in TABLE 2.

TABLE 2

| | FORWARD AND REVERSE PRIMER PAIR | |
|---|---|---|
| Forward | GGGAGACGGCATTCGTAATCGAATT CGCGGCCGCA | SEQ ID NO: 10 |
| Reverse | ATAGCAGAAGAAAATGGAGGAATTC TGTCAGACCAAGTTTACTCATATAT | SEQ ID NO: 11 |

The PCR products were purified using Zymo clean and concentrate 5 columns per manufacturer's instructions. Subsequently, the PCR products were assembled using prolonged overlap extension PCR (POE-PCR) with Q5 Polymerase (NEB) mixing the two fragments at equimolar ratio. The POE-PCR reactions were cycled: 98° C. for five (5) seconds, 64° C. for ten (10) seconds, 72° C. for four (4) minutes and fifteen (15) seconds for 30 cycles. Five (5) μl of the POE-PCR (DNA) was transformed into Top10 *E. coli* (Invitrogen) per manufacturer's instructions and selected on lysogeny (L) Broth (Miller recipe; 1% (w/v) Tryptone, 0.5% Yeast extract (w/v), 1% NaCl (w/v)), containing fifty (50) μg/ml kanamycin sulfate and solidified with 1.5% Agar. Colonies were allowed to grow for eighteen (18) hours at 37° C. Colonies were picked and plasmid DNA prepared using Qiaprep DNA miniprep kit per manufacturer's instructions and eluted in fifty-five (55) μl of ddH₂O. The plasmid DNA was Sanger sequenced to verify correct assembly, using the sequencing primers (SEQ ID NOs: 12-20) set forth below in TABLE 3.

TABLE 3

| | SEQUENCING PRIMERS | |
|---|---|---|
| Reverse | CCGACTGGAGCTCCTATATTACC | SEQ ID NO: 12 |
| Reverse | GCTGTGGCGATCTGTATTCC | SEQ ID NO: 13 |
| Forward | GTCTTTTAAGTAAGTCTACTCT | SEQ ID NO: 14 |
| Forward | CCAAAGCGATTTTAAGCGCG | SEQ ID NO: 15 |
| Forward | CCTGGCACGTGGTAATTCTC | SEQ ID NO: 16 |
| Forward | GGATTTCCTCAAATCTGACG | SEQ ID NO: 17 |
| Forward | GTAGAAACGCGCCAAATTACG | SEQ ID NO: 18 |
| Forward | GCTGGTGGTTGCTAAAGTCG | SEQ ID NO: 19 |
| Forward | GGACGCAACCCTCATTCATC | SEQ ID NO: 20 |

The correctly assembled plasmid, pRF694 (SEQ ID NO: 21), was used to assemble the intermediate plasmid, pRF748 (SEQ ID NO: 22). The construction of plasmid pRF748 was created by cloning an interrupted synthetic gRNA cassette into the NcoI/SalI sites of plasmid pRF694. This cassette was produced synthetically by IDT and contains the *B. subtilis* rrnIp2 promoter (SEQ ID NO: 39), a synthetic double terminator (SEQ ID NO: 24), the *E. coli* rpsL gene (SEQ ID NO: 25), the DNA encoding the Cas9 endonuclease recognition domain (SEQ ID NO: 26), and the lambda phage T0 terminator (SEQ ID NO: 27).

The DNA fragment containing the gRNA expression cassette can be assembled into pRF694 using standard molecular biology techniques generating plasmid pRF748, generating an *E. coli-B. subtilis* shuttle plasmid containing a Cas9 expression cassette and a gRNA expression cassette.

The intermediate plasmid, pRF748 was used to assemble the plasmid for the introduction of the expression cassettes into the aprE locus of *B. subtilis*. More particularly, the yhfN gene (SEQ ID NO: 28) in the aprE locus of *B. subtilis* contains a Cas9 target site (SEQ ID NO: 29). The target site can be converted into a DNA sequence encoding a variable targeting (VT) domain (SEQ ID NO: 30) by removing the PAM sequence (SEQ ID NO: 31). The DNA sequence encoding the VT domain (SEQ ID NO: 30) can be operably fused to the DNA sequence encoding the Cas9 Endonuclease Recognition domain (CER; SEQ ID NO: 26) such that when transcribed by RNA polymerase in the cell, it produces a functional gRNA (SEQ ID NO: 32). The DNA encoding the gRNA (SEQ ID NO: 33) can be operably linked to a promoter operable in *Bacillus* sp. cells (e.g., *B. subtilis* rrnIp2 promoter; SEQ ID NO: 39) and a terminator operable in *Bacillus* sp. cells (e.g., the lambda phage t0 terminator; SEQ ID NO: 26), such that the promoter is positioned 5' of the DNA encoding the gRNA and the terminator is positioned 3' of the DNA encoding the gRNA, to create a gRNA expression cassette (SEQ ID NO: 34).

Plasmid pRF793 (SEQ ID NO: 35), targeting the yhfN gene (SEQ ID NO:36) of *B. subtilis* was created by amplifying plasmid pRF748 (SEQ ID NO: 22), using Q5 according to the manufacturer's instructions and the forward (SEQ ID NO: 37) and reverse (SEQ ID NO: 37) primer pairs set forth in TABLE 4.

TABLE 4

| | FORWARD AND REVERSE PRIMER PAIR | |
|---|---|---|
| Forward | TTCAGGATTTGGCCGTGACGGTTTT AGAGCTAGAAATAGCAAGTT | SEQ ID NO: 37 |
| Reverse | CGTCACGGCCAAATCCTGAATTTAT TACTATAACATTTAGCTTCTTTTAA | SEQ ID NO: 38 |

These primers amplify the entire plasmid (pRF748) except for the variable targeting region of the gRNA creating a fragment in which the 5' and 3' ends overlap and containing the yhfN variable targeting domain. This PCR product was used for an intramolecular assembly reaction using NEBuilder (New England Biolabs) per the manufacturer's instructions, to create plasmid pRF793 (SEQ ID NO: 35), generating an E. coli-B. subtilis shuttle plasmid containing a Cas9 expression cassette and a gRNA expression cassette that encoding a gRNA targeting yhfN.

Example 2

Generation of Bacillus Cells Comprising Exemplary Expression Cassettes

In the present example, Applicant introduced protease expression cassettes (e.g., an exemplary POI) into B. subtilis cells. More specifically, the expression cassettes comprise (1) a DNA sequence homologous to flanking region upstream (5') of the yhfN gene (SEQ ID NO: 39) operably fused to either (2a) a DNA sequence encoding a native B. subtilis rrnIp2 promoter (SEQ ID NO: 39) or (2b) a genetically modified rrnIp2 sequence thereof, herein named the "rrnIp2-1 promoter (SEQ ID NO: 40), which native and modified promoter DNA sequences were (3) operably fused to a DNA sequence encoding a mature (subtilisin) protease, which was (4) operably fused to a DNA sequence encoding a B. amyloliquefaciens apr terminator sequence (SEQ ID NO: 41), wherein the promoter was positioned 5' of the DNA sequence encoding the protease and the terminator was positioned 3' of the DNA sequence encoding the protease. Lastly, the expression cassettes set forth above were operably fused to the DNA sequence homologous to the flanking region downstream (3') of the yhfN gene (SEQ ID NO: 42).

Thus, in the instant example, parental B. subtilis cells comprising the B. subtilis comK gene (SEQ ID NO: 44; introduced at the amyE locus using the PxylA inducible promoter), were grown overnight at 37° C. and 250 RPM in fifteen (15) ml of L broth (1% w·v$^{-1}$ Tryptone, 0.5% Yeast extract w·v$^{-1}$, 1% NaCl w·v$^{-1}$), in a one hundred and twenty-five (125) ml baffled flask. The overnight culture was diluted to 0.2 (OD$_{600}$ units) in ten (10) ml fresh L broth in a one hundred twenty-five (125) ml baffle flask.

Cells were grown until the culture reached 0.9 (OD$_{600}$ units) at 37° C. (250 RPM). D-xylose was added to 0.3% (w/v) from a 30% (w/v) stock. Cells were grown for an additional two and a half (2.5) hours at 37° C. (250 RPM) and pelleted at 1700×g for seven (7) minutes. The cells were resuspended in one fourth (¼) volume of original culture using the spent medium. One hundred (100) µl of concentrated cells were mixed with approximately one (1) µg of either (a) the protease expression cassette comprising the native rrnIp2 promoter (SEQ ID NO: 39) or (b) the protease expression cassette comprising the modified rrnIp2-1 promoter (SEQ ID NO: 40) and the pRF793 plasmid (SEQ ID NO: 34) described in Example 1, was amplified using rolling circle amplification (Syngis) for eighteen (18) hours according to the manufacturer's instructions. Cell/DNA transformation mixes were plated onto L-broth (miller) containing ten (10) µg/mL kanamycin, 1.6% (w/v) skim milk and solidified with 1.5% (w/v) agar. Colonies were allowed to form at 37° C.

Colonies that grew on L agar containing kanamycin and skim milk, and produced a visible clearing zone in the area adjacent to the colonies (i.e., indicative of proteolytic activity), were picked and streaked onto agar plates containing 1.6% (w/v) skim milk. A colony containing the protease expression cassette with the native rrnIp2 promoter was stored and named strain "SS066". A colony containing the protease expression cassette with the modified rrnIp2-1 promoter was stored and named strain "SS065".

Example 3

Protease Expression Under the Control of a Modified Promoter in Bacillus Cells

In the present example two (2) Bacillus cells (i.e., strains SS066 and SS065) comprising protease expression cassettes with either the native rrnIp2 promoter (SEQ ID NO: 39) or the modified rrnIp2-1 promoter (SEQ ID NO: 40) were assessed for protease production under small scale conditions. The two strains were streak purified on L agar plates containing 1.6% (w/v) skim milk and grown for approximately twenty-four (24) hours at 37° C. A single halo positive colony was inoculated into 25 ml of L Broth (1% w·v$^{-1}$ Tryptone, 0.5% Yeast extract w·v$^{-1}$, 1% NaCl w·v$^{-1}$) and grown at 37° C. (250 RPM) for five (5) hours. This pre-culture was diluted to 0.2 (OD$_{600}$ units) into 25 ml of MPS2 medium (10% w·v$^{-1}$ 10×MOPS based medium (8.4% w·v$^{-1}$ MOPS, 2.9% w·v$^{-1}$ Sodium Chloride, 1.2% w·v$^{-1}$ Potassium Hydroxide, 1% w·v$^{-1}$ Potassium Sulfate, 15 w·v$^{1}$ Magnesium Chloride, 0.7% w·v$^{-1}$ Tricine); 10% w·v$^{-1}$ Maltrin M150, 10% w·v$^{-1}$ micronutrients; 6% w·v$^{-1}$ soytone, 0.78% w·v$^{1}$ Dipotassium phosphate, 0.3% w·v$^{-1}$ urea, 0.2% Monopotassium phosphate, pH7.4 with Potassium hydroxide) and grown at 37° C. (250 RPM). The micronutrients were made up as a 100× stock solution in one (1) liter, 400 mg FeSO$_4$ 7H$_2$O, 100 mg MnSO$_4$H$_2$O, 100 mg ZnSO$_4$ 7H$_2$O, 50 mg CuCl$_2$ 2H$_2$O, 100 mg CoCl$_2$ 6H$_2$O, 100 mg NaMoO$_4$ 2H$_2$O, 100 mg Na$_2$B$_4$O$_7$ 10H$_2$O, 10 ml of 1M CaCl$_2$, and 10 ml of 0.5 M sodium citrate. After forty (40) hours for growth, the protease concentration in the whole cell broth was determined using the suc-AAPF-pNA assay.

For example, the suc-AAPF-pNA protease assay involves incubating the whole culture broth with a chromogenic peptide substrate under defined conditions and measuring the color development. The substrate is N-succinyl-L-Ala-L-Ala-L-Pro-L-Phe-p-nitroanilide (suc-AAPF-pNA). Upon hydrolysis of the peptide substrate by the protease, the 4-nitroanilide is cleaved and yields 4-nitroaniline, which is a yellow chromophore. Thus, the absorbance at 405 nm is measured and directly correlates to the level of protease in the analyzed sample. The equipment used for this set of assays includes a SpectraMAX MTP Reader (type 340-Molecular Devices). More particularly, in this assay system, the reagent and solutions used were: (1) N-succinyl-L-Ala-L-Ala-L-Pro-L-Phe-p-nitroanilide (Sigma); (2) Dilution buffer: 100 mM Tris-HCl, 10 mM CaCl$_2$, 0.005% TWEEN® 80 buffer, pH 8.6; and (3) Tris buffer: 100 mM Tris-HCl, 0.005% TWEEN® 80 buffer, pH 8.6.

Thus, a vial containing 100 mg of the suc-AAPF-pNA substrate was dissolved in one (1) ml of DMSO and a one (1) mg/ml working stock was made by adding one (1) ml of suc-AAPF-pNA to 100 mL of Tris buffer. The protease samples (whole cell broth) were diluted 1000× with dilution buffer. The assay was performed by adding ten (10) µl of diluted protease solution into the wells of a MTP, followed by the addition of one hundred and ninety (190) µl of the 1 mg/ml working suc-AAPF-pNA substrate solution. The solutions were mixed, and the absorbance was read at (λ) 405 nm in an MTP-Reader. A non-protease control was used to correct for background absorbance values. To calculate the protease concentration (mg/L), a dilution series of purified (variant) protease was used as a standard (control sample) and incorporated into the experiment. The relative protease activities are presented below in TABLE 5, showing the (normalized) relative protease expression of the SS065 cells (comprising the modified rrnIp2-1 promoter) relative to the SS066 cells (comprising the native rrnIp2 promoter), demonstrating an approximately 2-fold increase in protease activity.

TABLE 5

SMALL SCALE PRODUCTION OF PROTEASE

| B. subtilis cells | Promoter | Relative expression ± SEM |
|---|---|---|
| SS066 | Native rrnIp2 | 1.00 ± 0.07 |
| SS065 | Variant rrnIp2-1 | 2.09 ± 0.08 |

Example 4

Introducing Heterologous Amylase Expression Cassettes into Bacillus Cells

In the present example, a (heterologous) α-amylase expression cassette was introduced into parental B. licheniformis cells. More specifically, the α-amylase expression cassettes set forth below were introduced into B. licheniformis cells, wherein the cells comprised either (a) an expression cassette under the control of the native rrnIp2 promoter (SEQ ID NO: 39) or (b) an expression cassette under the control of the modified rrnIp2-1 promoter (SEQ ID NO: 40). Thus, in the instant example, B. licheniformis cells comprising a plasmid carrying a xylose-inducible comK expression cassette (SEQ ID NO: 43) were grown overnight at 37° C. and 250 RPM in fifteen (15) ml of L broth (1% (w/v) tryptone, 0.5% (w/v) yeast extract, 1% (w/v) NaCl), containing one hundred (100) µg/ml spectinomycin dihydrochloride in a one hundred twenty-five (125) ml baffle flask. The overnight culture was diluted to 0.7 ($OD_{600}$ units) in 25 ml fresh L broth containing one hundred (100) µg/ml spectinomycin dihydrochloride in a two hundred fifty (250) ml baffle flask. Cells were grown for one (1) hour at 37° C. and 250 RPM. D-xylose was added to 0.1% (w/v) from a 25% (w/v) stock, and the cells were grown for an additional four (4) hours at 37° C. and 250 RPM. Cells were pelleted at 1700·g for seven (7) minutes. The cells were resuspended in one fourth (¼) volume of original culture using spent medium. One hundred (100) µl of concentrated cells were mixed with approximately one (1) µg of either (a) the native rrnIp2 promoter expression construct (SEQ ID NO: 44) or (b) the modified rrnIp2-1 promoter expression construct (SEQ ID NO: 45).

For example, each cassette comprises (in the 5' to 3' direction) the same 5' lysA locus homology ARM (SEQ ID NO: 46), either the native rrnIp2 promoter (SEQ ID NO: 39) or the modified rrnIp2-1 promoter (SEQ ID NO: 40) operably linked to a modified aprE 5'-UTR (SEQ ID NO: 47). More particularly, the modified aprE 5'-UTR of SEQ ID NO: 47 is further described in International PCT Application No. PCT/US2018/049470 (filed Sep. 5, 2018; incorporated herein by reference in its entirety). In addition, the modified 5'-UTR was operably linked to a DNA sequence encoding the lat signal sequence (SEQ ID NO: 48), followed by a DNA sequence encoding a (variant) Cytophaga sp. α-amylase (SEQ ID NO: 49) which was operably linked to the lat terminator sequence (SEQ ID NO: 50), which was linked to the 3' lysA locus homology ARM (SEQ ID NO: 51).

Transformation reactions were incubated at 37° C. 1400 RPM for ninety (90) minutes. Cells were washed twice in 1% (w/v) KCl and plated on TSS agar (50 mM Tris, 37 mM $NH_4Cl$, 1.5 mM $K_2HPO_4.3H_2O$ pH 7.4, 0.5% (w/v) dextrose, 1 mM $MgSO_4.7H_2O$, 0.004% (w/v) $FeCl_3$, 0.004% (w/v) trisodium citrate) containing 1% (w/v) insoluble starch. Transformants were recovered at 37° C.

Halo positive transformants for the rrnIp2_α-amylase (SEQ ID NO: 44) and the rrnIp2-1_α-amylase (SEQ ID NO: 45) expression cassettes were streak purified on L agar containing 1% (w/v) insoluble starch to purify single colonies. The sequence of the expression cassette in purified halo-positive colonies was determined by amplifying the expression cassette using standard PCR techniques, using the primers set forth in TABLE 6.

TABLE 6

| FORWARD AND REVERSE PRIMER PAIR | | |
|---|---|---|
| lysA-F | GATTTGGGATTTGGAAATCC | SEQ ID NO: 52 |
| lysA-R | CAACACATTGCTTCAGGC | SEQ ID NO: 53 |

PCR products were sanger sequenced using standard techniques to verify the sequence of the expression cassette using the primers set forth in TABLE 7.

TABLE 7

| SEQUENCING PRIMERS | | |
|---|---|---|
| 1032 | TCAGAGAGAGACGTATGAGG | SEQ ID NO: 54 |
| 1033 | GCATGGACAGGCTTCAACTT | SEQ ID NO: 55 |
| 1034 | GGATGTCATTGGCTGGACGA | SEQ ID NO: 56 |
| 1035 | TCTACTCCGCCTCTAAATCC | SEQ ID NO: 57 |

A colony with a sequence verified cassette of the rrnIp2_α-amylase cassette (SEQ ID NO: 44) was stored and named "BF399" and a colony with a sequence verified cassette of the rrnIp2-1_α-amylase cassette (SEQ ID NO: 45) was stored and named "BF401".

Example 5

Heterologous Amylase Production in Bacillus Cells Comprising Amylase Expression Cassettes In the present example Applicant assayed Bacillus strains comprising the α-amylase expression cassettes described in Example 4. Thus, as presented below in TABLE 8, the native rrnIp2 promoter (i.e., the rrnIp2_α-amylase cassette; SEQ ID NO: 44) and the modified rrnIp2-1 promoter (i.e., the rrnIp2-1_α-amylase cassette; SEQ ID NO: 45) were tested for production of α-amylase to determine the influence these different promoters have on such heterologous protein production.

TABLE 8

STRAINS USED IN ASSAY FOR α-AMYLASE PRODUCTION

| Strain | Expression cassette | SEQ ID NO |
|---|---|---|
| BF399 | rrnIp2_α-amylase | SEQ ID NO: 44 |
| BF401 | rrnIp2-1_α-amylase | SEQ ID NO: 45 |

Strains were streaked on L broth (1% (w/v) tryptone, 0.5% (w/v) yeast extract, 1% (w/v) NaCl solidified with 1.5% (w/v) Bacto Agar containing 1% (w/v) insoluble starch and grown at 37° C. for 24 hours. A single colony was inoculated in 4 independent TSB (2% (w/v) non-animal origin peptone, 0.25% (w/v) dextrose, 0.5% (w/v) NaCl, 0.25% (w/v) $K_2HPO_4$). Cultures were grown at 37° C., 250 RPM and 80% humidity for twenty-four (24) hours. Cultures were pelleted at 4000 RPM for seven (7) minutes. Ten (10) μl of each clarified culture supernatant was measured for total protein production using the method of Bradford in duplicate, using a bovine serum albumin (BSA) standard. The relative amylase production for each strain was determined by performance relative to the strain comprising the rrnIp2_α-amylase cassette (SEQ ID NO: 44). More particularly, the relative production of the strains comprising either the native (promoter) rrnIp2_α-amylase cassette (SEQ ID NO: 44) or the modified (promoter) rrnIp2-1_α-amylase cassette (SEQ ID NO: 45) are shown below in TABLE 9, which data demonstrate that the strains comprising the modified rrnIp2-1_α-amylase cassette (SEQ ID NO: 45) produce on average 30% more amylase than strains comprising the native rrnIp2_α-amylase cassette (SEQ ID NO: 44).

TABLE 9

RELATIVE AMYLASE PRODUCTION OF STRAINS COMPRISING A SINGLE COPY OF rrnIp2_α-AMYLASE CASSETTE OR rrnIp2-1_α-AMYLASE CASSETTE

| Strain | Expression Cassette | SEQ ID NO | Relative protein production ± SEM |
|---|---|---|---|
| BF399 | rrnIp2_α-amylase cassette | SEQ ID NO: 44 | 1.00 ± 0.06 |
| BF400 | rrnIp2-1_α-amylase cassette | SEQ ID NO: 45 | 1.33 ± 0.03 |

Example 6

Introducing Heterologous Pullulanase Expression Cassettes into Bacillus Cells

In the present example, a heterologous (truncated) pullulanase expression cassette was introduced into B. licheniformis cells. More specifically, the truncated pullulanase expression cassettes set forth below were introduced into B. licheniformis cells, wherein the cells comprised either (a) an expression cassette under the control of the native B. licheniformis amyL promoter region (i.e., PamyL-1; SEQ ID NO: 64), (b) an expression cassette under the control of modified promoter region PamyL-2 (SEQ ID NO: 65), (c) an expression cassette under the control of modified promoter region PamyL-3; (SEQ ID NO: 66) or (d) an expression cassette under the control of modified promoter region PamyL-4 (SEQ ID NO: 67).

Thus, in the instant example, B. licheniformis cells comprising a plasmid carrying a xylose-inducible comK expression cassette (SEQ ID NO: 43) were grown overnight at 37° C. and 250 RPM in fifteen (15) ml of L broth (1% (w/v) tryptone, 0.5% (w/v) yeast extract, 1% (w/v) NaCl), containing one hundred (100) μg/ml spectinomycin dihydrochloride in a one hundred twenty-five (125) ml baffle flask. The overnight culture was diluted to 0.7 ($OD_{600}$ units) in 25 ml fresh L broth containing one hundred (100) μg/ml spectinomycin dihydrochloride in a two hundred fifty (250) ml baffle flask. Cells were grown for one (1) hour at 37° C. and 250 RPM. D-xylose was added to 0.1% (w/v) from a 25% (w/v) stock, and the cells were grown for an additional four (4) hours at 37° C. and 250 RPM. Cells were pelleted at 1700·g for seven (7) minutes. The cells were resuspended in one fourth (¼) volume of original culture using spent medium. One hundred (100) μl of concentrated cells were mixed with approximately one (1) μg of either the PamyL-1 expression cassette (SEQ ID NO: 78), the PamyL-2 expression cassette (SEQ ID NO: 79), the PamyL-3 expression cassette (SEQ ID NO: 80), or the PamyL-4 expression cassette (SEQ ID NO: 81).

For example, each cassette comprises (in the 5' to 3' direction) the same 5' lysA locus homology ARM (SEQ ID NO: 46), either the native B. licheniformis promoter region PamyL-1 (SEQ ID NO: 64), or one of the modified promoter region sequences PamyL-2 (SEQ ID NO: 65), PamyL-3 (SEQ ID NO: 66), or PamyL-4 (SEQ ID NO: 67) operably linked to a DNA sequence encoding the lat signal sequence (SEQ ID NO: 48), followed by a DNA sequence encoding a mature and truncated B. deramificans pullulanase (SEQ ID NO: 68) which was operably linked to the lat terminator sequence (SEQ ID NO: 50), which was linked to the 3' lysA locus homology ARM (SEQ ID NO: 51).

Transformation reactions were incubated at 37° C. 1400 RPM for ninety (90) minutes. Cells were washed twice in 1% (w/v) KCl and plated on Minimal agar (50 mM Tris, 37 mM $NH_4Cl$, 1.5 mM $K_2HPO_4 \cdot 3H_2O$ pH 7.4, 0.5% (w/v) dextrose, 1 mM $MgSO_4 \cdot 7H_2O$, 0.004% (w/v) $FeCl_3$, 0.004% (w/v) trisodium citrate) containing 0.5% (w/v) Remazol brilliant blue dyed starch. Transformants were recovered at 37° C.

Transformants for the PamyL-1 pullulanase cassette (SEQ ID NO: 78), PamyL-2 pullulanase cassette (SEQ ID NO: 79), PamyL-3 pullulanase cassette (SEQ ID NO: 80) and PamyL-4 pullulanase cassette (SEQ ID NO: 81) were streak purified on HI agar to purify single colonies. The sequence of the expression cassette in purified colonies was determined by amplifying the expression cassette using standard PCR techniques, using the primers set forth in TABLE 10.

TABLE 10

| | FORWARD AND REVERSE PRIMER PAIR | |
|---|---|---|
| 447 | CTACAGCATGGCCAACAACTA | SEQ ID NO: 69 |
| 674 | GTCATGATCTTTTTAACAAAAAAC | SEQ ID NO: 70 |

PCR products were sanger sequenced using standard techniques to verify the sequence of the expression cassette using the primers set forth in TABLE 11.

TABLE 11

SEQUENCING PRIMERS

| 447 | CTACAGCATGGCCAACAACTA | SEQ ID NO: 69 |
|---|---|---|
| 674 | GTCATGATCTTTTTAACAAAAAAC | SEQ ID NO: 70 |
| 766 | GATTGCTGACGCTGTTATTTGC | SEQ ID NO: 71 |
| 1694 | GTAGAAGTTGGTGCCCAGAC | SEQ ID NO: 72 |
| 1695 | GGAATACCTATACACAGAAAGCAAC | SEQ ID NO: 73 |
| 1697 | CATTCGCATTTGTAGCATACTGCC | SEQ ID NO: 74 |
| 1766 | CACGCAAATCTCTGACTTCG | SEQ ID NO: 75 |
| 1767 | CAAGCAGCGCCATTAAGTC | SEQ ID NO: 76 |
| 1768 | GCAACGACAATAGTTATAATG | SEQ ID NO: 77 |

A colony with a sequence verified cassette of the PamyL-1 pullulanase cassette (SEQ ID NO: 78), PamyL-2 pullulanase cassette (SEQ ID NO: 79), PamyL-3 pullulanase cassette (SEQ ID NO: 80) and PamyL-4 pullulanase (SEQ ID NO: 81) expression cassettes were streak purified, stored and named "PamyL-Pulltr.", "LDN461", "LDN462", and "LDN463", respectively.

Example 7

Heterologous Truncated Pullulanase Production in *Bacillus* Cells Comprising Truncated Pullulanase Expression Cassettes In the present example Applicant assayed *Bacillus* strains comprising the truncated pullulanase expression cassettes described in Example 6. Thus, as presented below in TABLE 12, the PamyL-1 pullulanase cassette (SEQ ID NO: 78) and the PamyL-2 pullulanase cassette (SEQ ID NO: 79) were tested for production of (truncated) pullulanase to determine the influence these different promoters and 5'-UTRs have on such heterologous pullulanase protein production.

TABLE 12

STRAINS USED IN ASSAY FOR TRUNCATED PULLULANASE PRODUCTION

| Strain | Expression cassette | SEQ ID NO |
|---|---|---|
| PamyL-Pulltr. | PamyL-1 pullulanase | SEQ ID NO: 78 |
| LDN461 | PamyL-2 pullulanase | SEQ ID NO: 79 |

Likewise, as presented below in TABLE 13, the PamyL-3 pullulanase cassette (SEQ ID NO: 80) and the PamyL-4 pullulanase cassette (SEQ ID NO: 81) were tested for production of (truncated) pullulanase to determine the influence these different promoters and 5'-UTRs have on such heterologous pullulanase protein production.

TABLE 13

STRAINS USED IN ASSAY FOR TRUNCATED PULLULANASE PRODUCTION

| Strain | Expression cassette | SEQ ID NO |
|---|---|---|
| LDN462 | PamyL-3 pullulanase | SEQ ID NO: 80 |
| LDN463 | PamyL-4 pullulanase | SEQ ID NO: 81 |

Strains were streaked on L broth (1% (w/v) tryptone, 0.5% (w/v) yeast extract, 1% (w/v) NaCl) solidified with 1.5% (w/v) Bacto Agar and grown at 37° C. for 24 hours. Three colonies were inoculated in TSB (2% (w/v), grown overnight at 37° C., 250 RPM, and 1:10 (v/v) transferred to non-defined MOPS buffer based media, and incubated for 68 hours, at 37° C., 250 RPM. Cultures were harvested and directly used to measure for total protein production using the method of Megazyme (PULLULANASE/LIMIT-DEXTRINASE ASSAY PROCEDURE (PullG6 METHOD)).

The relative (truncated) pullulanase production for strain LDN461 (PamyL-2 pullulanase; SEQ ID NO: 79) was determined by performance relative to strain PamyL-Pulltr (PamyL-1 pullulanase cassette; SEQ ID NO: 78). More particularly, the relative production of the PamyL-Pulltr strain (PamyL-1 pullulanase cassette; SEQ ID NO: 78) and the LDN461 strain (PamyL-2 pullulanase cassette; SEQ ID NO: 79) are shown below in TABLE 14, which data demonstrate that the LDN461 strain produces on average 78% more pullulanase than the PamyL-Pulltr. strain (PamyL-1 pullulanase cassette; SEQ ID NO: 78).

TABLE 14

RELATIVE PULLULANASE PRODUCTION OF STRAINS COMPRISING A SINGLE COPY OF PamyL-1 PULLULANASE CASSETTE OR PamyL-2 PULLULANASE CASSETTE

| Strain | Expression Cassette | SEQ ID NO | Relative protein production ± SEM |
|---|---|---|---|
| PamyL-Pulltr. | PamyL-1 pullulanase | SEQ ID NO: 78 | 1.00 ± 0.05 |
| LDN461 | PamyL-2 pullulanase | SEQ ID NO: 79 | 1.78 ± 0.05 |

Likewise, the relative (truncated) pullulanase production for strain LDN463 (PamyL-4 pullulanase cassette; SEQ ID NO: 81) was determined by performance relative to strain LDN462 (PamyL-3 pullulanase cassette; SEQ ID NO: 80), wherein the relative production of the strains are shown below in TABLE 15, which data demonstrate that the LDN463 strain (PamyL-4 pullulanase cassette) produces on average 16% more (truncated) pullulanase than the LDN462 strain (PamyL-3 pullulanase cassette; SEQ ID NO: 80).

TABLE 15

RELATIVE TRUNCATED PULLULANASE PRODUCTION OF STRAINS COMPRISING A SINGLE COPY OF PamyL-3 PULLULANASE CASSETTE OR PamyL-4 PULLULANASE CASSETTE

| Strain | Expression Cassette | SEQ ID NO | Relative protein production ± SEM |
|---|---|---|---|
| LDN462 | PamyL-3 pullulanase | SEQ ID NO: 80 | 1.00 ± 0.03 |

TABLE 15-continued

RELATIVE TRUNCATED PULLULANASE PRODUCTION
OF STRAINS COMPRISING A SINGLE COPY
OF PamyL-3 PULLULANASE CASSETTE OR
PamyL-4 PULLULANASE CASSETTE

| Strain | Expression Cassette | SEQ ID NO | Relative protein production ± SEM |
|---|---|---|---|
| LDN463 | PamyL-4 pullulanase | SEQ ID NO: 81 | 1.16 ± 0.07 |

REFERENCES

International PCT Application No. PCT/US2018/049470
International PCT Publication No. WO2003/083125
International PCT Publication No. WO2003/089604
International PCT Publication No. WO2013/086219
Botstein and Shortie, *Science* 229: 4719, 1985.
Brode et al., "Subtilisin BPN' variants: increased hydrolytic activity on surface-bound substrates via decreased surface activity", *Biochemistry*, 35(10):3162-3169, 1996.
Caspers et al., "Improvement of Sec-dependent secretion of a heterologous model protein in *Bacillus subtilis* by saturation mutagenesis of the N-domain of the AmyE signal peptide", *Appl. Microbiol. Biotechnol.*, 86(6):1877-1885, 2010.
Chang et al., *Mol. Gen. Genet.*, 168:11-115, 1979.
Devereux et al., *Nucl. Acid Res.*, 12: 387-395, 1984.
Earl et al., "Ecology and genomics of *Bacillus subtilis*", *Trends in Microbiology.*, 16(6):269-275, 2008.
Ferrari et al., "*Genetics,*" in Harwood et al. (ed), *Bacillus*, Plenum Publishing Corp., 1989.
Ferrari et al., "*Genetics,*" in Harwood et al. (ed), *Bacillus*, Plenum Publishing Corp., 1989.
Fisher et. al., *Arch. Microbiol.*, 139:213-217, 1981.
Hamoen et al., "Controlling competence in *Bacillus subtilis*: shared used of regulators", *Microbiology*, 149:9-17, 2003.
Hamoen et al., *Genes Dev.* 12:1539-1550, 1998.
Higuchi et al., *Nucleic Acids Research* 16: 7351, 1988.
Ho et al., *Gene* 77: 61, 1989.
Hoch et al., *J. Bacteriol.*, 93:1925-1937, 1967.
Hopwood, *The Isolation of Mutants in Methods in Microbiology* (J. R. Norris and D. W. Ribbons, eds.) pp 363-433, Academic Press, New York, 1970.
Horton et al., *Gene* 77: 61, 1989.
Iglesias and Trautner, *Molecular General Genetics* 189: 73-76, 1983.
Jensen et al., "Cell-associated degradation affects the yield of secreted engineered and heterologous proteins in the *Bacillus subtilis* expression system" *Microbiology*, 146 (Pt 10:2583-2594, 2000.
Liu and Zuber, "A Molecular Switch Controlling Competence and Motility: Competence Regulatory Factors ComS, MecA, and ComK Control Dependent Gene Expression in *Bacillus subtilis*", *J. Bacteriology*, 180(16): 4243-4251, 1998.
Lo et al., *Proceedings of the National Academy of Sciences USA* 81: 2285, 1985.
Mann et al., *Current Microbiol.*, 13:131-135, 1986. Holubova, 1985;
McDonald, *J. Gen. Microbiol.*, 130:203, 1984.
Needleman and Wunsch, *J. Mol. Biol.*, 48: 443, 1970.
Olempska-Beer et al., "Food-processing enzymes from recombinant microorganisms—a review" *Regul. Toxicol. Pharmacol.*, 45(2):144-158, 2006.
Palmeros et al., *Gene* 247:255-264, 2000.
Pearson and Lipman, *Proc. Natl. Acad. Sci. USA* 85: 2444, 1988.
Perego, 1993, In A. L. Sonneshein, J. A. Hoch, and R. Losick, editors, *Bacillus subtilis and Other Gram-Positive Bacteria*, Chapter 42, American Society of Microbiology, Washington, D.C.
Raul et al., "Production and partial purification of alpha amylase from *Bacillus subtilis* (MTCC 121) using solid state fermentation", *Biochemistry Research International*, 2014.
Sarkar and Sommer, *BioTechniques* 8: 404, 1990.
Saunders et al., *J. Bacteriol.*, 157:718-726, 1984.
Shimada, *Meth. Mol. Biol.* 57: 157; 1996.
Smith and Waterman, *Adv. Appl. Math.*, 2: 482, 1981.
Smith et al., *Appl. Env. Microbiol.*, 51:634 1986.
Solberg and Krauss, "Luciferase assay to study the activity of a cloned promoter DNA fragment", *Methods Mol Biol.* 977:65-78, 2013.
Stahl et al, *J. Bacteriol.*, 158:411-418, 1984.
Van Dijl and Hecker, "*Bacillus subtilis*: from soil bacterium to super-secreting cell factory", *Microbial Cell Factories*, 12(3). 2013.
Vorobjeva et al., *FEMS Microbiol. Lett.*, 7:261-263, 1980.
Westers et al., "*Bacillus subtilis* as cell factory for pharmaceutical proteins: a biotechnological approach to optimize the host organism", *Biochimica et Biophysica Acta.*, 1694: 299-310, 2004.
Youngman et al., *Proc. Natl. Acad. Sci. USA* 80: 2305-2309, 1983.

The invention claimed is:

1. A promoter sequence comprising at least 90% sequence identity to SEQ ID NO: 39 and comprising at least one mutation selected from the group consisting of a thymine (T) at nucleotide position 30 of SEQ ID NO: 39, a thymine (T) at nucleotide position 89 of SEQ ID NO: 39, a guanine (G) at nucleotide position 90 of SEQ ID NO: 39 and a thymine (T) at nucleotide position 91 of SEQ ID NO: 39.

2. The promoter of claim 1, comprising two to four mutations selected from the group consisting a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39.

3. The promoter of claim 1, comprising a gene or open reading frame (ORF) encoding a protein of interest (POI) positioned downstream (3') and operably linked to the promoter.

4. The promoter of claim 3, wherein the POI is an enzyme.

5. A modified Bacillus sp. cell comprising a promoter of claim 1.

6. A promoter region nucleic acid sequence comprising an (5') upstream promoter sequence operably linked to a (3') downstream 5'-UTR sequence, wherein the promoter sequence comprises at least 90% sequence identity to SEQ ID NO: 82 and comprises a thymine (T) at nucleotide position 72 of SEQ ID NO: 82, a guanine (G) at nucleotide position 73 of SEQ ID NO: 82 and a thymine (T) at nucleotide position 74 of SEQ ID NO: 82.

7. The promoter region nucleic acid sequence of claim 6, wherein the 5'-UTR sequence is a native amyL 5'-UTR sequence of SEQ ID NO: 84, a variant amyL 5'-UTR sequence thereof, or a native aprE 5'-UTR sequence of SEQ ID NO: 85, or a variant aprE 5'-UTR sequence thereof.

8. A modified B. licheniformis amyL promoter derived from a native B. licheniformis amyL promoter comprising a nucleotide sequence of SEQ ID NO: 82, wherein the modified promoter comprises at least 90% sequence identity to SEQ ID NO: 82 and comprises a thymine (T) at nucleotide position 72 of SEQ ID NO: 82, a guanine (G) at nucleotide position 73 of SEQ ID NO: 82 and a thymine (T) at nucleotide position 74 of SEQ ID NO: 82.

9. A method for enhanced protein production in a modified Bacillus sp. cell comprising:
   (a) introducing an expression cassette into a parental Bacillus sp. cell, wherein the cassette comprises a promoter positioned upstream (5') and operably linked to a gene coding sequence (CDS) encoding a protein of interest (POI), wherein the promoter comprises at least 90% identity to SEQ ID NO: 39 and comprises at least one modification selected from the group consisting of a T at nucleotide position 30 of SEQ ID NO: 39, a T at nucleotide position 89 of SEQ ID NO: 39, a G at nucleotide position 90 of SEQ ID NO: 39 and a T at nucleotide position 91 of SEQ ID NO: 39,
   and
   (b) fermenting the modified cell under suitable conditions for the production of the POI,
wherein the modified cell produces an increased amount of the POI relative to control Bacillus sp. cell comprising a polynucleotide expression cassette comprising a promoter sequence positioned upstream (5') and operably linked to the same gene CDS encoding the same POI, wherein the promoter comprises SEQ ID NO: 39.

* * * * *